United States Patent
Khvorova et al.

(10) Patent No.: US 12,258,566 B2
(45) Date of Patent: Mar. 25, 2025

(54) OLIGONUCLEOTIDES FOR PRNP MODULATION

(71) Applicant: UNIVERSITY OF MASSACHUSETTS, Boston, MA (US)

(72) Inventors: Anastasia Khvorova, Westborough, MA (US); Zachary Kennedy, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 591 days.

(21) Appl. No.: 17/187,129

(22) Filed: Feb. 26, 2021

(65) Prior Publication Data

US 2021/0317460 A1 Oct. 14, 2021

Related U.S. Application Data

(60) Provisional application No. 62/982,941, filed on Feb. 28, 2020.

(51) Int. Cl.
*C12N 15/113* (2010.01)
*C12Q 1/68* (2018.01)

(52) U.S. Cl.
CPC ...... *C12N 15/1138* (2013.01); *C12N 2310/14* (2013.01); *C12N 2310/315* (2013.01); *C12N 2310/3515* (2013.01); *C12N 2320/30* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,328,470 A | 7/1994 | Nabel et al. |
| 5,684,143 A | 11/1997 | Grayaznov et al. |
| 5,814,014 A | 9/1998 | Elsberry et al. |
| 5,858,988 A | 1/1999 | Wang |
| 6,093,180 A | 7/2000 | Elsberry et al. |
| 6,107,094 A | 8/2000 | Crooke |
| 6,168,587 B1 | 1/2001 | Bellhouse et al. |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 7,750,144 B2 | 7/2010 | Zamore et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 2005/0053583 A1 | 3/2005 | Sakaguchi et al. |
| 2005/0220766 A1 | 10/2005 | Amalfitano et al. |
| 2006/0078542 A1 | 4/2006 | Mah et al. |
| 2007/0031844 A1* | 2/2007 | Khvorova ...... C12Y 502/01008 435/6.13 |
| 2007/0259827 A1 | 11/2007 | Aronin et al. |
| 2008/0269149 A1 | 10/2008 | Bowles et al. |
| 2010/0186103 A1 | 7/2010 | Gao et al. |
| 2011/0269818 A1* | 11/2011 | Bennett ............. A61K 31/7125 536/24.5 |
| 2014/0296486 A1 | 10/2014 | Gao et al. |
| 2015/0166984 A1 | 6/2015 | Liu et al. |
| 2017/0096683 A1* | 4/2017 | Scaria ............... A61P 25/00 |
| 2017/0312367 A1* | 11/2017 | Khvorova ............. A61P 43/00 |
| 2018/0023094 A1* | 1/2018 | Gao .................... C12N 7/00 800/13 |
| 2018/0298380 A1* | 10/2018 | Gao ................ C12N 15/113 |
| 2020/0087663 A1 | 3/2020 | Aronin |
| 2022/0025366 A1* | 1/2022 | Freier ............... C12N 15/113 |

FOREIGN PATENT DOCUMENTS

| | | |
|---|---|---|
| EP | 4110913 A2 | 1/2023 |
| WO | WO 2003/029459 A2 | 4/2003 |
| WO | WO 2010/019270 A1 | 2/2010 |
| WO | WO 2011/038575 A1 | 4/2011 |
| WO | WO 2016/161388 A1 | 10/2016 |
| WO | WO 2017/030973 A1 | 2/2017 |
| WO | WO 2017/132669 A1 | 8/2017 |
| WO | WO 2018/031933 A2 | 2/2018 |
| WO | WO 2020/041769 A1 | 2/2020 |
| WO | WO 2021/173984 A2 | 9/2021 |

OTHER PUBLICATIONS

Vickers et al. The Journal of Biological Chemistry vol. 278(9):7108-7118, 2003.*
Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.
Alvarez-Erviti, et al., "Delivery of siRNA to the Mouse Brain By Systemic Injection of Targeted Exosomes", Nature Biotechnology, vol. 29, No. 4, pp. 341-345, Apr. 2011.
Ambros, et al., MicroRNAs and Other Tiny Endogenous RNAs in C. elegans, Current Biology, vol. 13, Issue 10, pp. 807-818, May 13, 2003.
Atwell, et al., Stable Heterodimers From Remodeling the Domain Interface of a Homodimer Using a Phage Display Library, Journal of Molecular Biology, vol. 270, Issue 1, pp. 26-35, Jul. 4, 1997.
Braasch, et al., "RNA Interference in Mammalian Cells by Chemically-Modified RNA", Biochemistry, vol. 42, No. 26, pp. 7967-7975, Jun. 11, 2003.
Brummelkamp, et al., A System for Stable Expression of Short Interfering RNAs in Mammalian Cells, Science, vol. 296, Issue 5567, pp. 550-553, Apr. 19, 2002.
Carter, "Handbook of Parvoviruses", ed., P. Tijsser, CRC Press, pp. 155-168, 1990.

(Continued)

*Primary Examiner* — Sean McGarry
(74) *Attorney, Agent, or Firm* — LATHROP GPM LLP; James H. Velema, Esq.; Michael J. Spellberg, Esq.

(57) ABSTRACT

This disclosure relates to novel PRNP targeting sequences. Novel PRNP targeting oligonucleotides for the treatment of neurodegenerative diseases are also provided.

50 Claims, 11 Drawing Sheets
Specification includes a Sequence Listing.

(56) References Cited

OTHER PUBLICATIONS

Chen, et al., "Gene Therapy for Brain Tumors: Regression of Experimental Gliomas by Adenovirus-Mediated Gene Transfer In Vivo", Proceedings of the National Academy of Sciences, vol. 91, No. 8, pp. 3054-3057, 1994.
Davidson, et al., A Model System for In Vivo Gene Transfer Into the Central Nervous System Using an Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types and Regions in the Mammalian Central Nervous System, Proceedings of the National Academy of Sciences, vol. 97, No. 7, pp. 3428-3432, Mar. 28, 2000.
Doench, et al., siRNAs can Function as miRNAs, Genes & Development, vol. 17, pp. 438-442, 2003.
Ducruix, et al., Crystallization of Nucleic Acids and Proteins: A Practical Approach, Second Edition, 1999, pp. 201-216.
Eckstein, Phosphorothioate Oligodeoxynucleotides: What is Their Origin and What is Unique About Them?, Antisense and Nucleic Acid Drug Development, vol. 10, Issue 2, pp. 117-121, Jan. 30, 2009.
Egusquiaguirre, et al., "Nanoparticle Delivery Systems for Cancer Therapy: Advances in Clinical and Preclinical Research", Clinical and Translational Oncology, vol. 14, pp. 83-93, 2012.
El Andaloussi, et al., "Exosome-Mediated Delivery of siRNA In Vitro and In Vivo", Nature Protocols, vol. 7, No. 12, pp. 2112-2126, Nov. 15, 2012.
El Andaloussi, et al., "Exosomes for Targeted siRNA Delivery Across Biological Barriers", Advanced Drug Delivery Reviews, vol. 65, pp. 391-397, 2013.
El Andaloussi, et al., "Extracellular Vesicles: Biology and Emerging Therapeutic Opportunities", Nature Reviews Drug Discovery, vol. 12, pp. 347-357, May 2013.
Elmen, et al., Locked Nucleic Acid (LNA) Mediated Improvements in siRNA Stability And Functionality, Nucleic Acids Research, vol. 33, Issue 1, pp. 439-447, Jan. 14, 2005.
Fattal, et al., Biodegradable Polyalkylcyanoacrylate Nanoparticles for the Delivery of Oligonucleotides, Journal of Controlled Release, vol. 53, pp. 137-143, May 1998.
Fisher, et al., Transduction With Recombinant Adeno-Associated Virus For Gene Therapy is Limited by Leading-Strand Synthesis, Journal of virology, vol. 70, No. 1, pp. 520-532, Jan. 1996.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Grad, et al., Computational and Experimental Identification of C. elegans microRNAs, Molecular Cell, vol. 11, Issue 5, pp. 1253-1263, May 2003.
Griffiths-Jones, San, The microRNA Registry, Nucleic Acids Research, vol. 32, Issue Supplement 1, pp. D109-D111, Jan. 1, 2004.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.
International Search Report and Written Opinion for PCT International Patent Application No. PCT/US2021/019888, mailed Sep. 1, 2021.
Karlin, et al., Applications and Statistics for Multiple High-Scoring Segments in Molecular Sequences, Proceedings of the National Academy of Sciences of the USA, vol. 90, pp. 5873-5877, Jun. 1993.
Karlin, et al., Methods for Assessing the Statistical Significance of Molecular Sequence Features by Using General Scoring Schemes, Proceedings of the National Academy of science of the USA, vol. 87, No. 6, pp. 2264-2268, Mar. 1990.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse and Human, RNA, vol. 9, No. 2, pp. 175-179, 2003.
Lai, et al., Computational Identification of Drosophila microRNA Genes, Genome Biology, vol. 4, No. 7, pp. 1-20, Jun. 30, 2003.
Lam, et al., "A New Type of Synthetic Peptide Library for Identifying Ligand-Binding Activity", Nature, vol. 354, pp. 82-84, Nov. 7, 1991.
Lambert, et al., "Nanoparticulate Systems for the Delivery of Antisense Oligonucleotides", Advanced Drug Delivery Reviews, vol. 47, pp. 99-112, 2001.
Lau, et al., An Abundant Class of Tiny RNAs with Probable Regulatory Roles in Caenorhabditis elegans, Science, vol. 294, Issue 5543, pp. 858-862, Oct. 26, 2001.
Lee, et al., "Recent Developments in Nanoparticle-Based siRNA Delivery for Cancer Therapy", BioMed Research International, vol. 2013, Article ID 782041, 10 Pages, Jun. 2013.
Lee, et al., An Extensive Class of Small RNAs in Caenorhabditis elegans, Science, vol. 294, Issue 5543, pp. 862-864, Oct. 26, 2001.
Lim, et al., The microRNAs of Caenorhabditis elegans, Genes & Development, vol. 17, No. 8, pp. 991-1008, 2003.
Lim, et al., Vertebrate MicroRNA Genes, Science, vol. 299, Issue 5612, p. 1540, Mar. 7, 2003.
McCaffrey, et al., Gene Expression: RNA Interference in Adult Mice, Nature, vol. 418, No. 6893, pp. 38-39, Jul. 4, 2002.
Miyagishi, et al., U6 promoter-driven siRNAs With Four Uridine 3' Overhangs Efficiently Suppress Targeted Gene Expression in Mammalian Cells, Nature Biotechnology, vol. 20, No. 5, pp. 497-500, May 1, 2002.
Mourelatos, et al., miRNPs: A Novel Class of Ribonucleoproteins Containing Numerous microRNAs, Genes & Development, vol. 16, No. 6, pp. 720-728, 2002.
Nielsen, et al., Sequence-Selective Recognition of DNA by Strand Displacement With a Thymine-Substituted Polyamide, Science, vol. 254, Issue 5037, pp. 1497-1500, Dec. 6, 1991.
Petersen, et al., LNA: A Versatile Tool for Therapeutics and Genomics, Trends in Biotechnology, vol. 21, Issue 2, pp. 74-81, Feb. 2003.
Putnam, David A., Antisense Strategies and Therapeutic Applications, American Journal of Health System Pharmacy, vol. 53, No. 2, pp. 151-160, Jan. 15, 1996.
Reinhart, et al., Small RNAs Correspond to Centromere Heterochromatic Repeats, Science, vol. 297, No. 5588, 1 Page, Sep. 13, 2002.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Schwab, et al., An Approach for New Anticancer Drugs:Oncogene-Targeted Antisense DNA, Annals of Oncology, vol. 5, Issue 4, pp. 55-58, 1994.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wang, et al., Nanoparticle-Based Delivery System for Application of siRNA In Vivo, Current Drug Metabolism, vol. 11, No. 2, pp. 182-196, 2010.
Xia, et al., siRNA-Mediated Gene Silencing in Vitroand In Vivo, Nature Biotechnology, vol. 20, No. 10, pp. 1006-1010, Sep. 16, 2002.
Yuan, et al., Recent Advances of siRNA Delivery by Nanoparticles, Expert Opinion on Drug Delivery vol. 8, Issue 4, pp. 521-536, 2011.

(56) References Cited

OTHER PUBLICATIONS

Zamore, et al., Ancient Pathways Programmed by Small RNAs, Science, May 17, 2002, 296(5571): 1265-1269.

Zeng, et al., Both Natural and Designed Micro RNAs Can Inhibit the Expression of Cognate mRNAs When Expressed in Human Cells, Molecular Cell, vol. 9, pp. 1327-1333, Jun. 2002.

Zeng, et al., Sequence Requirements for Micro RNA Processing and Function in Human Cells, RNA, vol. 9, pp. 112-123, 2003.

Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.

Avino, et al., "Branched RNA: A New Architecture for RNA Interference", Journal of Nucleic Acids, Mar. 6, 2011, 2011(586935): 1-7.

Hu, et al., "Pharmacological Prion Protein Silencing Accelerates Central Nervous System Autoimmune Disease via T Cell Receptor Signalling", Brain, Feb. 2010, 133(2): 375-388.

Kang, et al., "Dual MicroRNA to Cellular Prion Protein Inhibits Propagation of Pathogenic Prion Protein in Cultured Cells", Molecular Neurobiology, Mar. 2018, 55(3): 2384-2396.

Kang, et al., "Establishment and Characterization of Prnp Knockdown Neuroblastoma Cells Using Dual microRNA-mediated RNA Interference", Prion, Apr. 2011, 5(2): 93-102.

Kim, "Utility of RNAi-mediated prnp Gene Silencing in Neuroblastoma Cells Permanently Infected by Prions: Potentials and Limitations", Antiviral Research, Nov. 2009, 84(2): 185-193.

Partial Supplementary European Search Report received in European Patent Application No. 21761310.8, dated Apr. 2, 2024.

Shi, et al., "Prion Protein Participates in the Regulation of Classical and Alternative Activation of BV2 Microglia", Journal of Neurochemistry, Jan. 2013, 124(2): 168-174.

Supplementary European Search Report received in European Patent Application No. 21761310.8, dated Jun. 24, 2024.

Sutou, et al., "Knockdown of the Bovine Prion Gene PRNP by RNA Interference (RNAi) Technology", BMC Biotechnology, Jul. 26, 2007, 7(44): 1-10.

\* cited by examiner

OLIGONUCLEOTIDES FOR PRNP MODULATION

CROSS-REFERENCE TO RELATED APPLICATIONS

This application claims the benefit of U.S. Provisional Application Ser. No. 62/982,941, filed Feb. 28, 2020, the entire disclosure of which is incorporated herein by reference.

FIELD OF THE INVENTION

This disclosure relates to novel PRNP targeting sequences, novel branched oligonucleotides, and novel methods for treating and preventing PRNP-related neurodegeneration.

BACKGROUND

PRNP (prion protein, PrP, CD230) encodes a protein known for its role in the pathogenesis of several neurodegenerative disorders known as prion diseases, which includes Creutzfeldt-Jakob disease (CJD). In pathological conditions, prion protein misfolds and recruits other prion protein molecules to misfold. The misfolded proteins may spread from cell to cell and in some cases, to a new host. Accordingly, there existing a need to efficiently and potently silence PRNP mRNA expression, which the present application addresses.

SUMMARY

In one aspect, the disclosure provides an RNA molecule comprising: about 8 nucleotides to 80 nucleotides in length; and a sequence substantially complementary to a PRNP nucleic acid sequence of any one of SEQ ID NOs: 1-12, 95, 112, 114, 124, 181, or 182 (e.g., a PRNP nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 95, SEQ ID NO: 112, SEQ ID NO: 114, SEQ ID NO: 124, SEQ ID NO: 181, or SEQ ID NO: 182).

In certain embodiments, the RNA molecule comprises a sequence substantially complementary to a PRNP nucleic acid sequence of any one of SEQ ID NOs: 13-38, 217, 234, 236, 246, 303, or 304 (e.g., a PRNP nucleic acid sequence of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 217, SEQ ID NO: 234, SEQ ID NO: 236, SEQ ID NO: 246, SEQ ID NO: 303, or SEQ ID NO: 304).

In certain embodiments, the RNA molecule comprises about 15 nucleotides to 25 nucleotides in length.

In certain embodiments, the RNA molecule comprises single stranded (ss) RNA or double stranded (ds) RNA.

In certain embodiments, the dsRNA comprises a sense strand and an antisense strand, wherein the antisense strand comprises a sequence substantially complementary to a PRNP nucleic acid sequence of any one of SEQ ID NOs: 1-12, 95, 112, 114, 124, 181, or 182 (e.g., a PRNP nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 95, SEQ ID NO: 112, SEQ ID NO: 114, SEQ ID NO: 124, SEQ ID NO: 181, or SEQ ID NO: 182).

In certain embodiments, the dsRNA comprises complementarity to at least 10, 11, 12 or 13 contiguous nucleotides of a PRNP nucleic acid sequence of any one of SEQ ID NOs: 1-12, 95, 112, 114, 124, 181, or 182 (e.g., a PRNP nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 95, SEQ ID NO: 112, SEQ ID NO: 114, SEQ ID NO: 124, SEQ ID NO: 181, or SEQ ID NO: 182).

In certain embodiments, the dsRNA comprises no more than 3 mismatches with a PRNP nucleic acid sequence of any one of SEQ ID NOs: 1-12, 95, 112, 114, 124, 181, or 182 (e.g., a PRNP nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 95, SEQ ID NO: 112, SEQ ID NO: 114, SEQ ID NO: 124, SEQ ID NO: 181, or SEQ ID NO: 182).

In certain embodiments, the dsRNA comprises full complementarity to a PRNP nucleic acid sequence of any one of SEQ ID NOs: 1-12, 95, 112, 114, 124, 181, or 182 (e.g., a PRNP nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 95, SEQ ID NO: 112, SEQ ID NO: 114, SEQ ID NO: 124, SEQ ID NO: 181, or SEQ ID NO: 182).

In certain embodiments, the antisense strand and/or sense strand comprises about 15 nucleotides to 25 nucleotides in length. In certain embodiments, the antisense strand is 20 nucleotides in length. In certain embodiments, the antisense strand is 21 nucleotides in length. In certain embodiments, the antisense strand is 22 nucleotides in length. In certain embodiments, the sense strand is 15 nucleotides in length. In certain embodiments, the sense strand is 16 nucleotides in length. In certain embodiments, the sense strand is 18 nucleotides in length. In certain embodiments, the sense strand is 20 nucleotides in length.

In certain embodiments, the dsRNA comprises a double-stranded region of 15 base pairs to 20 base pairs. In certain embodiments, the dsRNA comprises a double-stranded region of 15 base pairs. In certain embodiments, the dsRNA comprises a double-stranded region of 16 base pairs. In certain embodiments, the dsRNA comprises a double-stranded region of 18 base pairs. In certain embodiments, the dsRNA comprises a double-stranded region of 20 base pairs.

In certain embodiments, the dsRNA comprises a blunt-end. In certain embodiments, the dsRNA comprises at least one single stranded nucleotide overhang. In certain embodiments, the dsRNA comprises about a 2-nucleotide to 5-nucleotide single stranded nucleotide overhang.

In certain embodiments, the dsRNA comprises naturally occurring nucleotides.

In certain embodiments, the dsRNA comprises at least one modified nucleotide.

In certain embodiments, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a mixture thereof.

In certain embodiments, the dsRNA comprises at least one modified internucleotide linkage.

In certain embodiments, the modified internucleotide linkage comprises a phosphorothioate internucleotide linkage. In certain embodiments, the dsRNA comprises 4-16 phosphorothioate internucleotide linkages. In certain embodiments, the dsRNA comprises 8-13 phosphorothioate internucleotide linkages.

In certain embodiments, the dsRNA comprises at least one modified internucleotide linkage of Formula I:

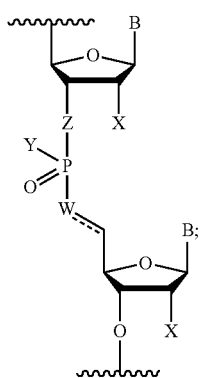

(I)

wherein:
B is a base pairing moiety;
W is selected from the group consisting of O, OCH$_2$, OCH, CH$_2$, and CH;
X is selected from the group consisting of halo, hydroxy, and C$_{1-6}$ alkoxy;
Y is selected from the group consisting of O$^-$, OH, OR, NH$^-$, NH$_2$, S$^-$, and SH;
Z is selected from the group consisting of O and CH$_2$;
R is a protecting group; and
=== is an optional double bond.

In certain embodiments, when W is CH, === is a double bond.

In certain embodiments, when W is selected from the group consisting of O, OCH$_2$, OCH, CH$_2$, === is a single bond.

In certain embodiments, the dsRNA comprises at least 80% chemically modified nucleotides. In certain embodiments, the dsRNA is fully chemically modified. In certain embodiments, the dsRNA comprises at least 70% 2'-O-methyl nucleotide modifications.

In certain embodiments, the antisense strand comprises at least 80% chemically modified nucleotides. In certain embodiments, the antisense strand is fully chemically modified. In certain embodiments, the antisense strand comprises at least 70% 2'-O-methyl nucleotide modifications. In certain embodiments, the antisense strand comprises about 70% to 90% 2'-O-methyl nucleotide modifications.

In certain embodiments, the sense strand comprises at least 80% chemically modified nucleotides. In certain embodiments, the sense strand is fully chemically modified. In certain embodiments, the sense strand comprises at least 70% 2'-O-methyl nucleotide modifications. In certain embodiments, the sense strand comprises 100% 2'-O-methyl nucleotide modifications.

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand.

In certain embodiments, the antisense strand comprises a 5' phosphate, a 5'-alkyl phosphonate, a 5' alkylene phosphonate, or a 5' alkenyl phosphonate.

In certain embodiments, the antisense strand comprises a 5' vinyl phosphonate.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of SEQ ID NOs: 1-12, 95, 112, 114, 124, 181, or 182; (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 70% 2'-O-methyl modifications; (3) the nucleotide at position 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 85% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand is 21 nucleotides in length; (3) the antisense strand comprises at least 85% 2'-O-methyl modifications; (4) the nucleotides at positions 2, 14, and 20 from the 5' end of the antisense strand are not 2'-methoxy-ribonucleotides; (5) the nucleotides at positions 1-2 to 1-7 from the 3' end of the antisense strand are connected to each other via phosphorothioate internucleotide linkages; (6) a portion of the antisense strand is complementary to a portion of the sense strand; (7) the sense strand is 15 or 16 nucleotides in length; (8) the sense strand comprises 100% 2'-O-methyl modifications; and (9) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 6, 14, and 16 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; (7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand is 21 nucleotides in length; (3) the antisense strand comprises at least 75% 2'-O-methyl modifications; (4) the nucleotides at positions 2, 6, 14, 16, and 21 from the 5' end of the antisense strand are not 2'-methoxy-ribonucleotides; (5) the nucleotides at positions 1-2 to 1-7 from the 3' end of the antisense strand are connected to each other via phosphorothioate internucleotide linkages; (6) a portion of the antisense strand is complementary to a portion of the sense strand; (7) the sense strand is 15 or 16 nucleotides in length; (8) the sense strand comprises at least 70% 2'-O-methyl modifications; (9) the nucleotides at positions 7, 9, 10, and 11 from the 3' end of the sense strand are not 2'-methoxy-ribonucleotides; and (10) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 80% 2'-O-methyl modifications; (7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, a functional moiety is linked to the 5' end and/or 3' end of the antisense strand. In certain embodiments, a functional moiety is linked to the 5' end and/or 3' end of the sense strand. In certain embodiments, a functional moiety is linked to the 3' end of the sense strand.

In certain embodiments, the functional moiety comprises a hydrophobic moiety.

In certain embodiments, the hydrophobic moiety is selected from the group consisting of fatty acids, steroids, secosteroids, lipids, gangliosides, nucleoside analogs, endocannabinoids, vitamins, and a mixture thereof.

In certain embodiments, the steroid selected from the group consisting of cholesterol and Lithocholic acid (LCA).

In certain embodiments, the fatty acid selected from the group consisting of Eicosapentaenoic acid (EPA), Docosahexaenoic acid (DHA) and Docosanoic acid (DCA).

In certain embodiments, the vitamin is selected from the group consisting of choline, vitamin A, vitamin E, and derivatives or metabolites thereof.

In certain embodiments, the vitamin is selected from the group consisting of retinoic acid and alpha-tocopheryl succinate.

In certain embodiments, the functional moiety is linked to the antisense strand and/or sense strand by a linker.

In certain embodiments, the linker comprises a divalent or trivalent linker.

In certain embodiments, the divalent or trivalent linker is selected from the group consisting of:

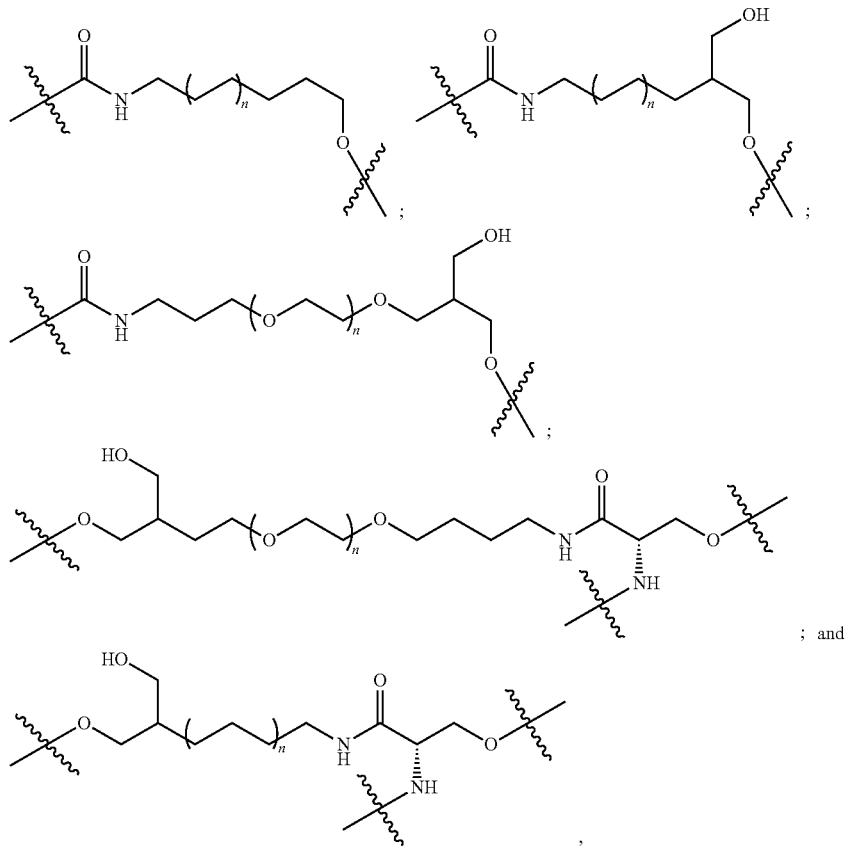

wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, when the linker is a trivalent linker, the linker further links a phosphodiester or phosphodiester derivative.

In certain embodiments, the phosphodiester or phosphodiester derivative is selected from the group consisting of:

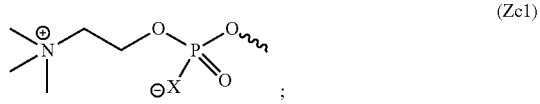
(Zc1)

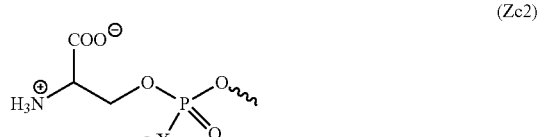
(Zc2)

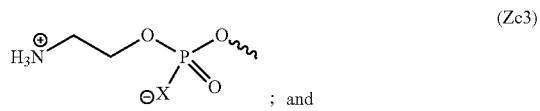
(Zc3)

; and

-continued

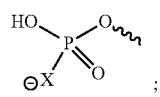
(Zc4)

wherein X is O, S or $BH_3$.

In certain embodiments, the nucleotides at positions 1 and 2 from the 3' end of sense strand, and the nucleotides at positions 1 and 2 from the 5' end of antisense strand, are connected to adjacent ribonucleotides via phosphorothioate linkages.

In one aspect, the disclosure provides a pharmaceutical composition for inhibiting the expression of prion protein (PRNP) gene in an organism, comprising the dsRNA recited above and a pharmaceutically acceptable carrier.

In certain embodiments, the dsRNA inhibits the expression of said PRNP gene by at least 50%. In certain embodiments, the dsRNA inhibits the expression of said PRNP gene by at least 80%.

In one aspect, the disclosure provides a method for inhibiting expression of PRNP gene in a cell, the method comprising: (a) introducing into the cell a double-stranded ribonucleic acid (dsRNA) recited above; and (b) maintaining the cell produced in step (a) for a time sufficient to obtain degradation of the mRNA transcript of the PRNP gene, thereby inhibiting expression of the PRNP gene in the cell.

In one aspect, the disclosure provides a method of treating or managing a neurodegenerative disease comprising administering to a patient in need of such treatment or management a therapeutically effective amount of said dsRNA recited above.

In certain embodiments, the dsRNA is administered to the brain of the patient.

In certain embodiments, the dsRNA is administered by intracerebroventricular (ICV) injection, intrastriatal (IS) injection, intravenous (IV) injection, subcutaneous (SQ) injection or a combination thereof.

In certain embodiments, administering the dsRNA causes a decrease in PRNP gene mRNA in one or more of the hippocampus, striatum, cortex, cerebellum, thalamus, hypothalamus, and spinal cord.

In certain embodiments, the dsRNA inhibits the expression of said PRNP gene by at least 50%. In certain embodiments, the dsRNA inhibits the expression of said PRNP gene by at least 80%.

In one aspect, the disclosure provides a vector comprising a regulatory sequence operably linked to a nucleotide sequence that encodes an RNA molecule substantially complementary to a PRNP nucleic acid sequence of any one of SEQ ID NOs: 1-12, 95, 112, 114, 124, 181, or 182.

In certain embodiments, the RNA molecule inhibits the expression of said PRNP gene by at least 50%. In certain embodiments, the RNA molecule inhibits the expression of said PRNP gene by at least 80%.

In certain embodiments, the RNA molecule comprises ssRNA or dsRNA.

In certain embodiments, the dsRNA comprises a sense strand and an antisense strand, wherein the antisense strand comprises a sequence substantially complementary to a PRNP nucleic acid sequence of any one of SEQ ID NOs: 1-12, 95, 112, 114, 124, 181, or 182.

In one aspect, the disclosure provides a cell comprising the vector recited above.

In one aspect, the disclosure provides a recombinant adeno-associated virus (rAAV) comprising the vector above and an AAV capsid.

In one aspect, the disclosure provides a branched RNA compound comprising: two or more RNA molecules comprising 15 to 35 nucleotides in length, and a sequence substantially complementary to a PRNP mRNA, wherein the two RNA molecules are connected to one another by one or more moieties independently selected from a linker, a spacer and a branching point.

In certain embodiments, the branched RNA compound comprises a sequence substantially complementary to a PRNP nucleic acid sequence of any one of SEQ ID NOs: 1-12, 95, 112, 114, 124, 181, or 182.

In certain embodiments, the branched RNA compound comprises a sequence substantially complementary to one or more of a PRNP nucleic acid sequence of any one of SEQ ID NOs: 13-38, 217, 234, 236, 246, 303, or 304.

In certain embodiments, the RNA molecule comprises one or both of ssRNA and dsRNA.

In certain embodiments, the RNA molecule comprises an antisense oligonucleotide.

In certain embodiments, each RNA molecule comprises 15 to 25 nucleotides in length.

In certain embodiments, each RNA molecule comprises a dsRNA comprising a sense strand and an antisense strand, wherein each antisense strand independently comprises a sequence substantially complementary to a PRNP nucleic acid sequence of any one of SEQ ID NOs: 1-12, 95, 112, 114, 124, 181, or 182.

In certain embodiments, the branched RNA compound comprises complementarity to at least 10, 11, 12 or 13 contiguous nucleotides of a PRNP nucleic acid sequence of SEQ ID NO: 1-1 any one of SEQ ID NOs: 1-12, 95, 112, 114, 124, 181, or 182.

In certain embodiments, each RNA molecule comprises no more than 3 mismatches with a PRNP nucleic acid sequence of any one of SEQ ID NOs: 1-12, 95, 112, 114, 124, 181, or 182.

In certain embodiments, the branched RNA compound comprises full complementary to a PRNP nucleic acid sequence of any one of SEQ ID NOs: 1-12, 95, 112, 114, 124, 181, or 182.

In certain embodiments, the antisense strand and/or sense strand comprises about 15 nucleotides to 25 nucleotides in length. In certain embodiments, the antisense strand is 20 nucleotides in length. In certain embodiments, the antisense strand is 21 nucleotides in length. In certain embodiments, the antisense strand is 22 nucleotides in length. In certain embodiments, the sense strand is 15 nucleotides in length. In certain embodiments, the sense strand is 16 nucleotides in length. In certain embodiments, the sense strand is 18 nucleotides in length. In certain embodiments, the sense strand is 20 nucleotides in length.

In certain embodiments, the dsRNA comprises a double-stranded region of 15 base pairs to 20 base pairs. In certain embodiments, the dsRNA comprises a double-stranded region of 15 base pairs. In certain embodiments, the dsRNA comprises a double-stranded region of 16 base pairs. In certain embodiments, the dsRNA comprises a double-stranded region of 18 base pairs. In certain embodiments, the dsRNA comprises a double-stranded region of 20 base pairs.

In certain embodiments, the dsRNA comprises a blunt-end.

In certain embodiments, the dsRNA comprises at least one single stranded nucleotide overhang. In certain embodiments, the dsRNA comprises between a 2-nucleotide to 5-nucleotide single stranded nucleotide overhang.

In certain embodiments, the dsRNA comprises naturally occurring nucleotides.

In certain embodiments, the dsRNA comprises at least one modified nucleotide.

In certain embodiments, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In certain embodiments, the dsRNA comprises at least one modified internucleotide linkage.

In certain embodiments, the modified internucleotide linkage comprises a phosphorothioate internucleotide linkage. In certain embodiments, the branched RNA compound comprises 4-16 phosphorothioate internucleotide linkages. In certain embodiments, the branched RNA compound comprises 8-13 phosphorothioate internucleotide linkages.

In certain embodiments, the dsRNA comprises at least one modified internucleotide linkage of Formula I:

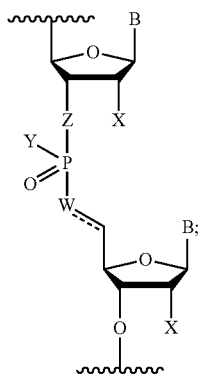

(I)

wherein:
B is a base pairing moiety;
W is selected from the group consisting of O, OCH$_2$, OCH, CH$_2$, and CH;
X is selected from the group consisting of halo, hydroxy, and C$_{1-6}$ alkoxy;
Y is selected from the group consisting of O$^-$, OH, OR, NH$^-$, NH$_2$, S$^-$, and SH;
Z is selected from the group consisting of O and CH$_2$;
R is a protecting group; and
═══ is an optional double bond.

In certain embodiments, when W is CH, ═══ is a double bond.

In certain embodiments, when W is selected from the group consisting of O, OCH$_2$, OCH, CH$_2$, ═══ is a single bond.

In certain embodiments, the dsRNA comprises at least 80% chemically modified nucleotides. In certain embodiments, the dsRNA is fully chemically modified. In certain embodiments, the dsRNA comprises at least 70% 2'-O-methyl nucleotide modifications.

In certain embodiments, the antisense strand comprises at least 80% chemically modified nucleotides. In certain embodiments, the antisense strand is fully chemically modified. In certain embodiments, the antisense strand comprises at least 70% 2'-O-methyl nucleotide modifications. In certain embodiments, the antisense strand comprises about 70% to 90% 2'-O-methyl nucleotide modifications.

In certain embodiments, the sense strand comprises at least 80% chemically modified nucleotides. In certain embodiments, the sense strand is fully chemically modified. In certain embodiments, the sense strand comprises at least 70% 2'-O-methyl nucleotide modifications. In certain embodiments, the sense strand comprises 100% 2'-O-methyl nucleotide modifications.

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand.

In certain embodiments, the antisense strand comprises a 5' phosphate, a 5'-alkyl phosphonate, a 5' alkylene phosphonate, a 5' alkenyl phosphonate, or a mixture thereof.

In certain embodiments, the antisense strand comprises a 5' vinyl phosphonate.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 70% 2'-O-methyl modifications; (3) the nucleotide at position 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 85% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 6, 14, and 16 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; (7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a PRNP nucleic acid sequence of any one of SEQ ID NOs: 1-12, 95, 112, 114, 124, 181, or 182; (2) the antisense strand comprises at least 75% 2'-O-methyl modifications; (3) the nucleotides at positions 2, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 80% 2'-O-methyl modifications; (7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, a functional moiety is linked to the 5' end and/or 3' end of the antisense strand. In certain embodiments, a functional moiety is linked to the 5' end and/or 3' end of the sense strand. In certain embodiments, a functional moiety is linked to the 3' end of the sense strand.

In certain embodiments, the functional moiety comprises a hydrophobic moiety.

In certain embodiments, the hydrophobic moiety is selected from the group consisting of fatty acids, steroids, secosteroids, lipids, gangliosides and nucleoside analogs, endocannabinoids, vitamins, and a mixture thereof.

In certain embodiments, the steroid selected from the group consisting of cholesterol and Lithocholic acid (LCA).

In certain embodiments, the fatty acid selected from the group consisting of Eicosapentaenoic acid (EPA), Docosahexaenoic acid (DHA) and Docosanoic acid (DCA).

In certain embodiments, the vitamin selected from the group consisting of choline, vitamin A, vitamin E, and derivatives or metabolites thereof.

In certain embodiments, the vitamin is selected from the group consisting of retinoic acid and alpha-tocopheryl succinate.

In certain embodiments, the functional moiety is linked to the antisense strand and/or sense strand by a linker.

In certain embodiments, the linker comprises a divalent or trivalent linker.

In certain embodiments, the divalent or trivalent linker is selected from the group consisting of:

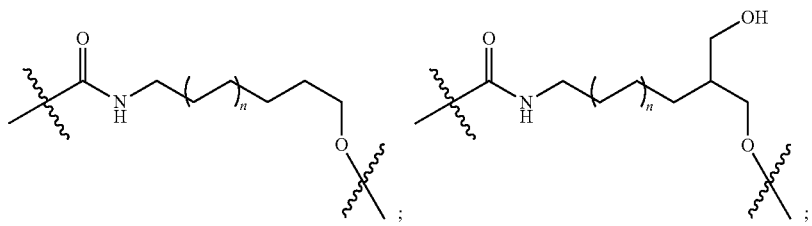

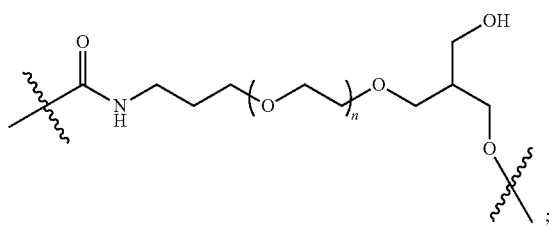

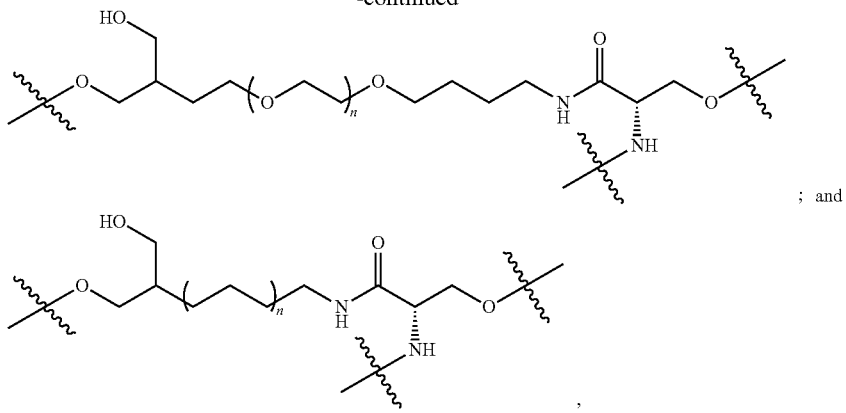

; and wherein n is 1, 2, 3, 4, or 5.

In certain embodiments, the linker comprises an ethylene glycol chain, an alkyl chain, a peptide, RNA, DNA, a phosphodiester, a phosphorothioate, a phosphoramidate, an amide, a carbamate, or a combination thereof.

In certain embodiments, when the linker is a trivalent linker, the linker further links a phosphodiester or phosphodiester derivative.

In certain embodiments, the phosphodiester or phosphodiester derivative is selected from the group consisting of:

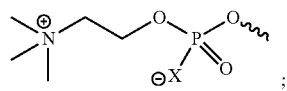 (Zc1)

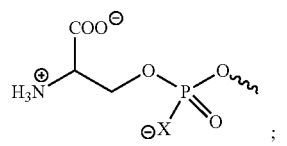 (Zc2)

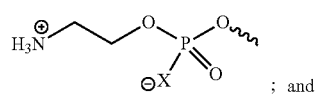 (Zc3)

; and

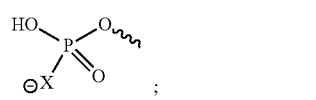 (Zc4)

;

wherein X is O, S or $BH_3$.

In certain embodiments, the nucleotides at positions 1 and 2 from the 3' end of sense strand, and the nucleotides at positions 1 and 2 from the 5' end of antisense strand, are connected to adjacent ribonucleotides via phosphorothioate linkages.

In one aspect, the disclosure provides a compound of formula (I):

L-(N)$_n$     (I)

wherein

L comprises an ethylene glycol chain, an alkyl chain, a peptide, an RNA, a DNA, a phosphate, a phosphonate, a phosphoramidate, an ester, an amide, a triazole, or combinations thereof, wherein formula (I) optionally further comprises one or more branch point B, and one or more spacer S, wherein B is independently for each occurrence a polyvalent organic species or derivative thereof;

S comprises independently for each occurrence an ethylene glycol chain, an alkyl chain, a peptide, RNA, DNA, a phosphate, a phosphonate, a phosphoramidate, an ester, an amide, a triazole, or combinations thereof; and N is a double stranded nucleic acid comprising 15 to 35 bases in length comprising a sense strand and an antisense strand; wherein the antisense strand comprises a sequence substantially complementary to a PRNP nucleic acid sequence of any one of SEQ ID NOs: 1-12, 95, 112, 114, 124, 181, or 182;

the sense strand and antisense strand each independently comprise one or more chemical modifications; and n is 2, 3, 4, 5, 6, 7 or 8.

In certain embodiments, the compound comprises a structure selected from formulas (I-1)-(I-9):

N—L—N     (I-1)

N—S—L—S—N     (I-2)

$$\begin{array}{c} \text{N} \\ | \\ \text{L} \\ | \\ \text{N—L—B—L—N} \end{array}$$ (I-3)

$$\begin{array}{c} \text{N} \\ | \\ \text{L} \\ | \\ \text{N—L—B—L—N} \\ | \\ \text{L} \\ | \\ \text{N} \end{array}$$ (I-4)

$$\begin{array}{cc} \text{N} & \text{N} \\ | & | \\ \text{S} & \text{S} \\ | & | \\ \text{N—S—B—L—B—S—N} \end{array}$$ (I-5)

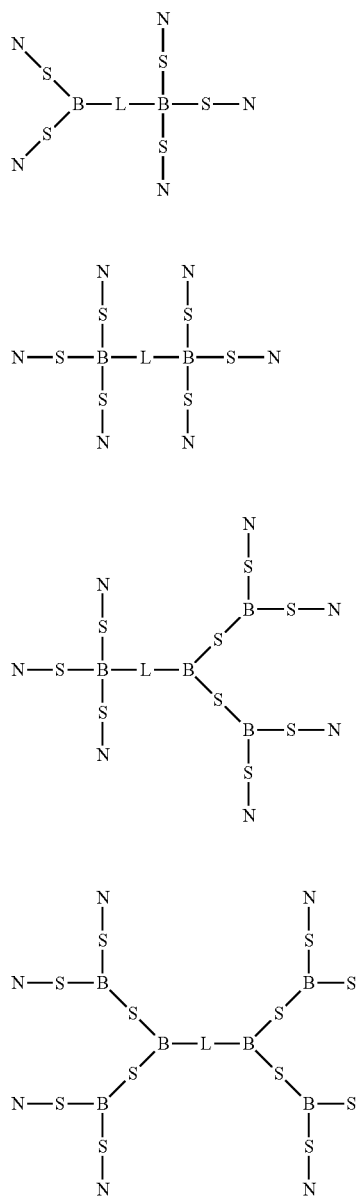
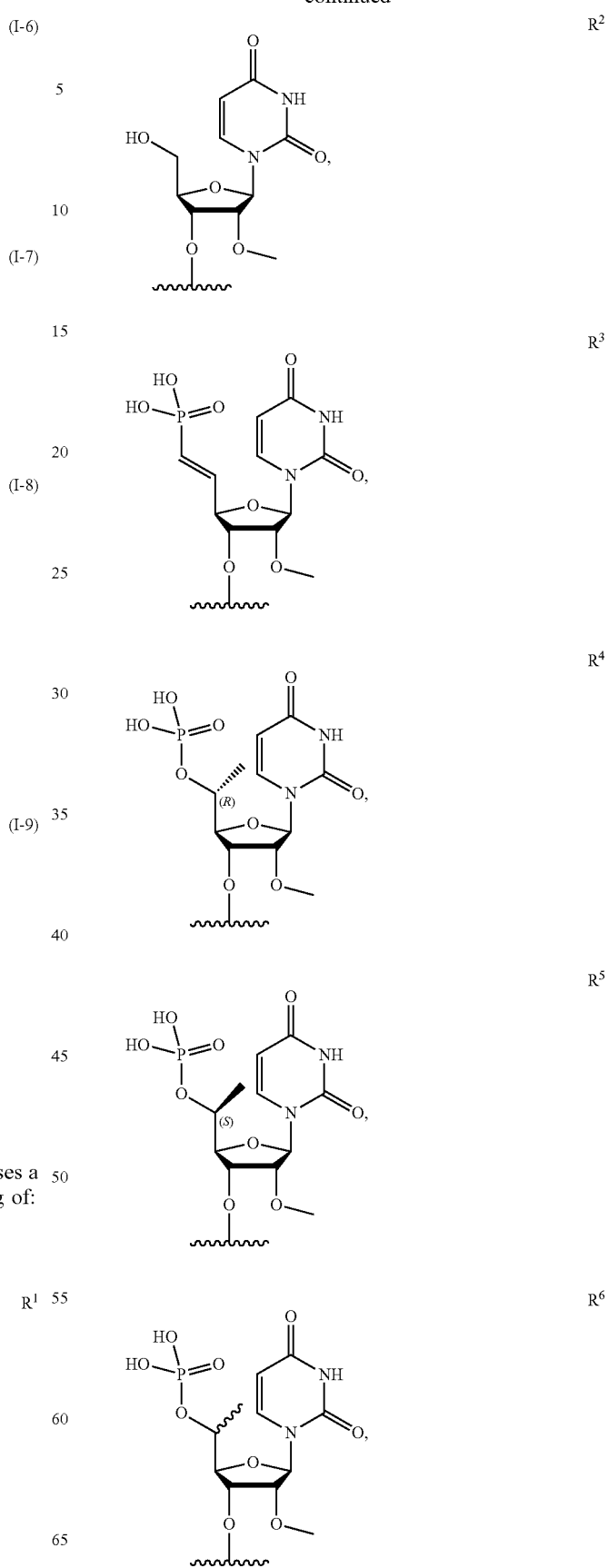
In certain embodiments, the antisense strand comprises a 5' terminal group R selected from the group consisting of:
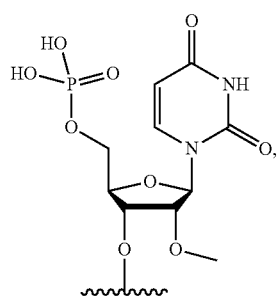
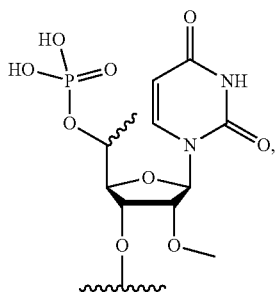

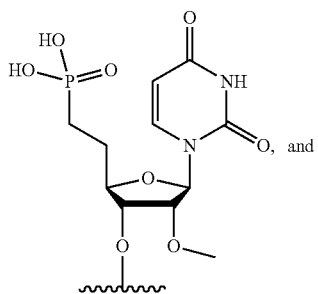

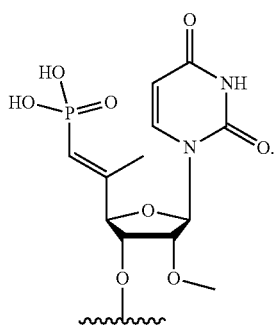

In certain embodiments, the compound comprises the structure of formula (II):

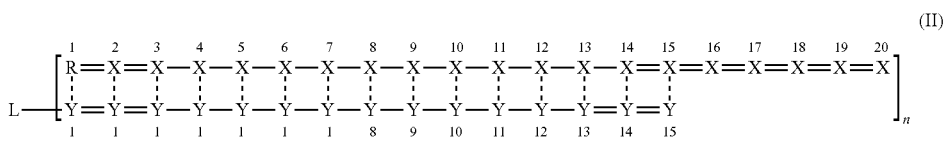

(II)

wherein
- X, for each occurrence, independently, is selected from adenosine, guanosine, uridine, cytidine, and chemically-modified derivatives thereof;
- Y, for each occurrence, independently, is selected from adenosine, guanosine, uridine, cytidine, and chemically-modified derivatives thereof;
- - represents a phosphodiester internucleoside linkage;
- = represents a phosphorothioate internucleoside linkage; and
- --- represents, individually for each occurrence, a base-pairing interaction or a mismatch.

In certain embodiments, the compound comprises the structure of formula (IV):

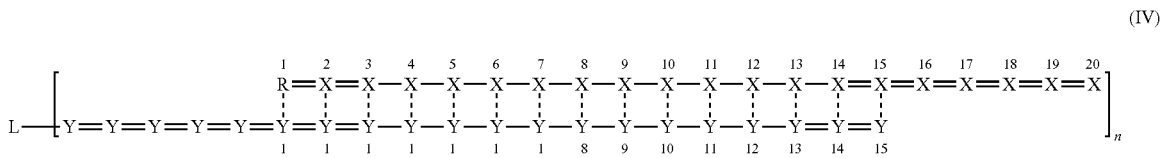

(IV)

wherein
- X, for each occurrence, independently, is selected from adenosine, guanosine, uridine, cytidine, and chemically-modified derivatives thereof;
- Y, for each occurrence, independently, is selected from adenosine, guanosine, uridine, cytidine, and chemically-modified derivatives thereof;
- - represents a phosphodiester internucleoside linkage;
- = represents a phosphorothioate internucleoside linkage; and
- --- represents, individually for each occurrence, a base-pairing interaction or a mismatch.

In certain embodiments, L is of structure L1:

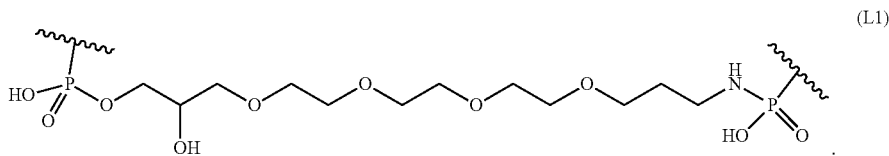 [SMILES: *P(=O)(O)NCCCOCCOCCOCCOCC(O)COP(*)(=O)O]
(L1)

In certain embodiments, R is $R^3$ and n is 2.
In certain embodiments, L is of structure L2:

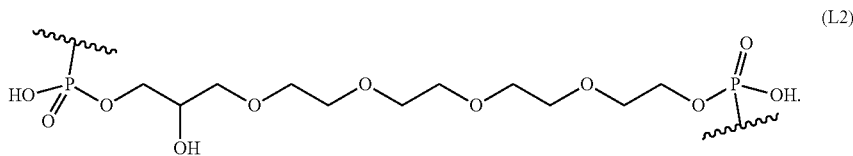 [SMILES: *P(=O)(O)OCCOCCOCCOCCOCC(O)COP(*)(=O)O]
(L2)

In certain embodiments, R is $R^3$ and n is 2.

In one aspect, the disclosure provides a delivery system for therapeutic nucleic acids having the structure of Formula (VI):

L-(cNA)$_n$  (VI)

wherein

L comprises an ethylene glycol chain, an alkyl chain, a peptide, an RNA, a DNA, a phosphate, a phosphonate, a phosphoramidate, an ester, an amide, a triazole, or combinations thereof, wherein formula (VI) optionally further comprises one or more branch point B, and one or more spacer S, wherein B comprises independently for each occurrence a polyvalent organic species or derivative thereof;

S comprises independently for each occurrence an ethylene glycol chain, an alkyl chain, a peptide, RNA, DNA, a phosphate, a phosphonate, a phosphoramidate, an ester, an amide, a triazole, or combinations thereof;

each cNA, independently, is a carrier nucleic acid comprising one or more chemical modifications;

each cNA, independently, comprises at least 15 contiguous nucleotides of a PRNP nucleic acid sequence of any one of SEQ ID NOs: 1-12, 95, 112, 114, 124, 181, or 182; and n is 2, 3, 4, 5, 6, 7 or 8.

In certain embodiments, the delivery system comprises a structure selected from formulas (VI-1)-(VI-9):

ANc—L—cNA  (VI-1)

ANc—S—L—S—cNA  (VI-2)

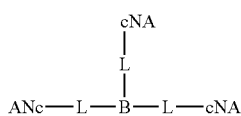
(VI-3)

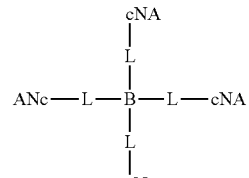
(VI-4)

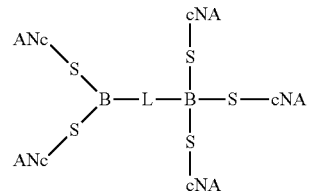
(VI-5)

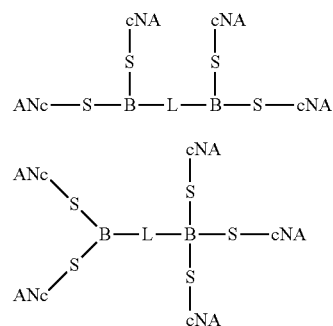
(VI-6)

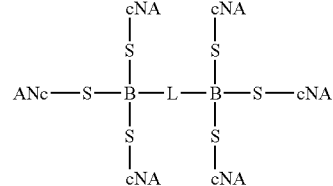
(VI-7)

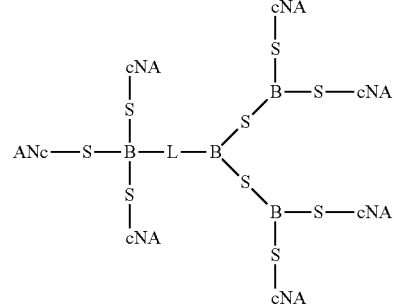
(VI-8)

(VI-9)

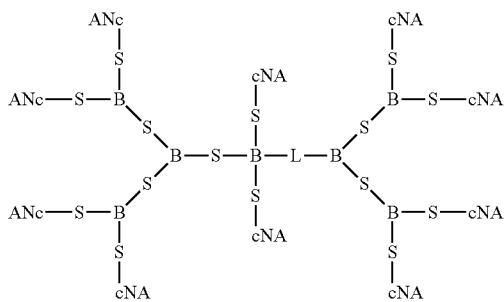

In certain embodiments, each cNA independently comprises chemically-modified nucleotides.

In certain embodiments, delivery system further comprises n therapeutic nucleic acids (NA), wherein each NA is hybridized to at least one cNA.

In certain embodiments, each NA independently comprises at least 16 contiguous nucleotides.

In certain embodiments, each NA independently comprises 16-20 contiguous nucleotides.

In certain embodiments, each NA comprises an unpaired overhang of at least 2 nucleotides.

In certain embodiments, the nucleotides of the overhang are connected via phosphorothioate linkages.

In certain embodiments, each NA, independently, is selected from the group consisting of DNA, siRNAs, antagomiRs, miRNAs, gapmers, mixmers, and guide RNAs.

In certain embodiments, each NA is substantially complementary to a PRNP nucleic acid sequence of any one of SEQ ID NOs: 1-12, 95, 112, 114, 124, 181, or 182.

In one aspect, the disclosure provides a pharmaceutical composition for inhibiting the expression of PRNP gene in an organism, comprising a compound recited above or a system recited above, and a pharmaceutically acceptable carrier.

In certain embodiments, the compound or system inhibits the expression of the PRNP gene by at least 50%. In certain embodiments, the compound or system inhibits the expression of the PRNP gene by at least 80%.

In one aspect, the disclosure provides a method for inhibiting expression of PRNP gene in a cell, the method comprising: (a) introducing into the cell a compound recited above or a system recited above; and (b) maintaining the cell produced in step (a) for a time sufficient to obtain degradation of the mRNA transcript of the PRNP gene, thereby inhibiting expression of the PRNP gene in the cell.

In one aspect, the disclosure provides a method of treating or managing a neurodegenerative disease comprising administering to a patient in need of such treatment or management a therapeutically effective amount of a compound recited above or a system recited above.

In certain embodiments, the dsRNA is administered to the brain of the patient.

In certain embodiments, the dsRNA is administered by intracerebroventricular (ICV) injection, intrastriatal (IS) injection, intravenous (IV) injection, subcutaneous (SQ) injection, or a combination thereof.

In certain embodiments, administering the dsRNA causes a decrease in PRNP gene mRNA in one or more of the hippocampus, striatum, cortex, cerebellum, thalamus, hypothalamus, and spinal cord.

In certain embodiments, the dsRNA inhibits the expression of said PRNP gene by at least 50%. In certain embodiments, the dsRNA inhibits the expression of said PRNP gene by at least 80%.

BRIEF DESCRIPTION OF THE DRAWINGS

The foregoing and other features and advantages of the present disclosure will be more fully understood from the following detailed description of illustrative embodiments taken in conjunction with the accompanying drawings.

DETAILED DESCRIPTION

Figure 1:
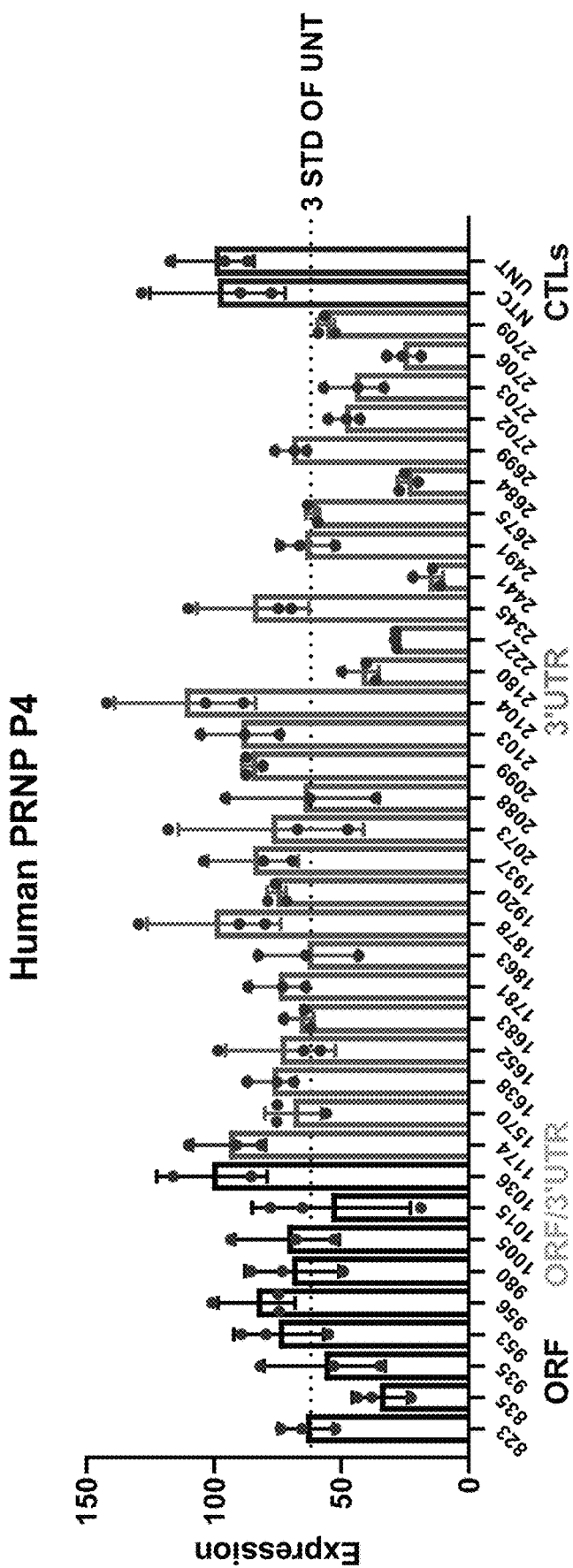
FIG. 1 depicts a screen of siRNAs targeting sequences of human PRNP mRNA in A549 human carcinoma cells.

Novel PRNP target sequences are provided. Also provided are novel siRNAs that target the novel PRNP target sequences of the disclosure.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N2,N2-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs), which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include: the 5 position, e.g., 5-(2-amino)propyl uridine, 5-bromo uridine, 5-propyne uridine, 5-propenyl uridine, etc.; the 6 position, e.g., 6-(2-amino)propyl uridine; and the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs, such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function, such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a short polymer of nucleotides and/or nucleotide analogs.

The term "RNA analog" refers to a polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. As discussed above, the oligonucleotides may be linked with linkages, which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Some RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand, which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) and causes or contributes to a disease or disorder. The gain-of-function mutation can be a deletion, addition, or substitution of a nucleotide or nucleotides in the gene, which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In certain embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In certain embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In certain embodiments, the sample population may comprise individuals, which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of consecutive glutamine residues linked to peptide bonds. In one embodiment the consecutive region includes at least 5 glutamine residues.

The term "expanded polyglutamine domain" or "expanded polyglutamine segment," as used herein, refers to a segment or domain of a protein that includes at least 35 consecutive glutamine residues linked by peptide bonds. Such expanded segments are found in subjects afflicted with a polyglutamine disorder, as described herein, whether or not the subject manifests symptoms.

The term "trinucleotide repeat" or "trinucleotide repeat region" as used herein, refers to a segment of a nucleic acid sequence that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to Huntington's disease (HD), spino-cerebellar ataxia type 12 spino-cerebellar ataxia type 8, fragile X syndrome, fragile XE mental retardation, Friedreich's ataxia and myotonic dystrophy. Exemplary trinucleotide repeat diseases for treatment according to the present invention are those characterized or caused by an expanded trinucleotide repeat region at the 5' end of the coding region of a gene, the gene encoding a mutant protein, which causes or is causative of the disease or disorder. Certain trinucleotide diseases, for example, fragile X syndrome, where the mutation is not associated with a coding region, may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The phrase "examining the function of a gene in a cell or organism" refers to examining or studying the expression, activity, function or phenotype arising therefrom.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small noncoding RNAs can be generated. Exemplary RNA silencing agents include siRNAs, miRNAs, siRNA-like duplexes, antisense oligonucleotides, GAPMER molecules, and dual-function oligonucleotides, as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also known in the art as "small temporal RNAs" ("stRNAs"), refers to a small (10-50 nucleotide) RNA, which are genetically encoded (e.g., by viral, mammalian, or plant genomes) and are capable of directing or mediating RNA silencing. An "miRNA disorder" shall refer to a disease or disorder characterized by an aberrant expression or activity of a miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA).

As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like, between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety), which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the invention are described in further detail in the following subsections.

I. Novel Target Sequences

In certain exemplary embodiments, RNA silencing agents of the invention are capable of targeting a PRNP nucleic acid sequence of any one of SEQ ID NOs: 1-12, 95, 112, 114, 124, 181, or 182, as recited in Table 4, Table 5, and Table 9. In certain exemplary embodiments, RNA silencing agents of the invention are capable of targeting one or more of a PRNP nucleic acid sequence selected from the group consisting of any one of SEQ ID NOs: 13-38, 217, 234, 236, 246, 303, or 304, as recited in Tables 6-8 and 10.

Genomic sequence for each target sequence can be found in, for example, the publicly available database maintained by the NCBI.

II. siRNA Design

In some embodiments, siRNAs are designed as follows. First, a portion of the target gene (e.g., the PRNP gene), e.g., one or more of the target sequences set forth in Tables 4-6 is selected. Cleavage of mRNA at these sites should eliminate translation of corresponding protein. Antisense strands were designed based on the target sequence and sense strands were designed to be complementary to the antisense strand. Hybridization of the antisense and sense strands forms the siRNA duplex. The antisense strand includes about 19 to 25 nucleotides, e.g., 19, 20, 21, 22, 23, 24 or 25 nucleotides. In other embodiments, the antisense strand includes 20, 21, 22 or 23 nucleotides. The sense strand includes about 14 to 25 nucleotides, e.g., 14, 15, 16, 17, 18, 19, 20, 21, 22, 23, 24 or 25 nucleotides. In other embodiments, the sense strand is 15 nucleotides. In other embodiments, the sense strand is 18 nucleotides. In other embodiments, the sense strand is 20 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention, provided that they retain the ability to mediate RNAi. Longer RNAi agents have been demonstrated to elicit an interferon or PKR response in certain mammalian cells, which may be undesirable. In certain embodiments, the RNAi agents of the invention do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence can be designed such that the target sequence is essentially in the middle of the strand. Moving the target sequence to an off-center position can, in some instances, reduce efficiency of cleavage by the siRNA. Such compositions, i.e., less efficient compositions, may be desirable for use if off-silencing of the wild-type mRNA is detected.

The antisense strand can be the same length as the sense strand and includes complementary nucleotides. In one embodiment, the strands are fully complementary, i.e., the strands are blunt-ended when aligned or annealed. In another embodiment, the strands align or anneal such that 1-, 2-, 3-, 4-, 5-, 6-, 7-, or 8-nucleotide overhangs are generated, i.e., the 3' end of the sense strand extends 1, 2, 3, 4, 5, 6, 7, or 8 nucleotides further than the 5' end of the antisense strand and/or the 3' end of the antisense strand extends 1, 2, 3, 4, 5, 6, 7, or 8 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the PRNP target sequences set forth in Tables 4-6 is described in detail below. siRNAs can be designed according to the above exemplary teachings for any other target sequences found in the PRNP gene. Moreover, the technology is applicable to targeting any other target sequences, e.g., non-disease-causing target sequences.

To validate the effectiveness by which siRNAs destroy mRNAs (e.g., PRNP mRNA), the siRNA can be incubated with cDNA (e.g., PRNP cDNA) in a *Drosophila*-based in vitro mRNA expression system. Radiolabeled with $^{32}P$, newly synthesized mRNAs (e.g., PRNP mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

III. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katand-in.cshl.org:9331/RNAi/docs/Web_version_of_PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems, such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., PRNP genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding PRNP, targeting the same gene or multiple genes, and can be driven, for example, by separate PolIII promoter sites.

Animal cells express a range of noncoding RNAs of approximately 22 nucleotides termed micro RNA (miR-NAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative, as compared to the corresponding siRNA, and are useful for tracing the siRNA derivative in the cell, or improving the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA, which will be targeted by the siRNA generated from the engineered RNA precursor, and will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis), generated (e.g., enzymatically generated), or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, such as about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-PRNP RNA Silencing Agents

In one embodiment, the present invention provides novel anti-PRNP RNA silencing agents (e.g., siRNA, shRNA, and antisense oligonucleotides), methods of making said RNA silencing agents, and methods (e.g., research and/or therapeutic methods) for using said improved RNA silencing agents (or portions thereof) for RNA silencing of PRNP protein. The RNA silencing agents comprise an antisense strand (or portions thereof), wherein the antisense strand has sufficient complementary to a target PRNP mRNA to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-20 base pair duplexes; (4) greater than 50% 2'-methoxy modifications, such as 70%-100% 2'-methoxy modifications, although an alternating pattern of chemically-modified nucleotides (e.g., 2'-fluoro and 2'-methoxy modifications), are also contemplated; and (5) single-stranded, fully phosphorothioated tails of 5-8 bases. In certain embodiments, the number of phosphorothioate modifications is varied from 4 to 16 total. In certain embodiments, the number of phosphorothioate modifications is varied from 8 to 13 total.

In certain embodiments, the siRNA compounds described herein can be conjugated to a variety of targeting agents, including, but not limited to, cholesterol, docosahexaenoic acid (DHA), phenyltropanes, cortisol, vitamin A, vitamin D, N-acetylgalactosamine (GalNac), and gangliosides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

The compounds of the invention can be described in the following aspects and embodiments.

In a first aspect, provided herein is a double stranded RNA (dsRNA) comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises alternating 2'-methoxy-ribonucleotides and 2'-fluoro-ribonucleotides;
(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises alternating 2'-methoxy-ribonucleotides and 2'-fluoro-ribonucleotides; and
(7) the nucleotides at positions 1-2 from the 5' end of the sense strand are connected to each other via phosphorothioate internucleotide linkages.

In a second aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 70% 2'-O-methyl modifications;
(3) the nucleotide at position 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 70% 2'-O-methyl modifications; and
(7) the nucleotides at positions 1-2 from the 5' end of the sense strand are connected to each other via phosphorothioate internucleotide linkages.

In a third aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 85% 2'-O-methyl modifications;
(3) the nucleotides at positions 2 and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a fourth aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 75% 2'-O-methyl modifications;
(3) the nucleotides at positions 4, 5, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a fifth aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 75% 2'-O-methyl modifications;
(3) the nucleotides at positions 2, 4, 5, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a sixth aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 75% 2'-O-methyl modifications;
(3) the nucleotides at positions 2, 6, 14, and 16 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 70% 2'-O-methyl modifications;
(7) the nucleotides at positions 7, 9, 10, and 11 from the 3' end of the sense strand are not 2'-methoxy-ribonucleotides; and
(8) the nucleotides at positions 1-2 from the 5' end of the sense strand are connected to each other via phosphorothioate internucleotide linkages.

In a seventh aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a PRNP nucleic acid sequence of any one of SEQ ID NOs: 1-12, 95, 112, 114, 124, 181, or 182;
(2) the antisense strand comprises at least 75% 2'-O-methyl modifications;
(3) the nucleotides at positions 2, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 80% 2'-O-methyl modifications;
(7) the nucleotides at positions 7, 10, and 11 from the 3' end of the sense strand are not 2'-methoxy-ribonucleotides; and
(8) the nucleotides at positions 1-2 from the 5' end of the sense strand are connected to each other via phosphorothioate internucleotide linkages.

a) Design of Anti-PRNP siRNA Molecules

An siRNA molecule of the application is a duplex made of a sense strand and complementary antisense strand, the antisense strand having sufficient complementarity to a PRNP mRNA to mediate RNAi. In certain embodiments, the siRNA molecule has a length from about 10-50 or more nucleotides, i.e., each strand comprises 10-50 nucleotides (or nucleotide analogs). In other embodiments, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In certain embodiments, the strands are aligned such that there are at least 1, 2, 3, 4, 5, 6, 7, 8, 9, or 10 bases at the end of the strands, which do not align (i.e., for which no complementary bases occur in the opposing strand), such that an overhang of 1, 2, 3, 4, 5, 6, 7, 8, 9, or 10 residues occurs at one or both ends of the duplex when strands are annealed.

Usually, siRNAs can be designed by using any method known in the art, for instance, by using the following protocol:

1. The siRNA should be specific for a target sequence, e.g., a target sequence set forth in the Examples. The first strand should be complementary to the target sequence, and the other strand is substantially complementary to the first strand. (See Examples for exemplary sense and antisense strands.) Exemplary target sequences are selected from any region of the target gene that leads to potent gene silencing. Regions of the target gene include, but are not limited to, the 5' untranslated region (5'-UTR) of a target gene, the 3' untranslated region (3'-UTR) of a target gene, an exon of a target gene, or an intron of a target gene. Cleavage of mRNA at these sites should eliminate translation of corresponding PRNP protein. Target sequences from other regions of the PRNP gene are also suitable for targeting. A sense strand is designed based on the target sequence.

2. The sense strand of the siRNA is designed based on the sequence of the selected target site. In certain embodiments, the sense strand includes about 15 to 25 nucleotides, e.g., 15, 16, 17, 18, 19, 20, 21, 22, 23, 24 or 25 nucleotides. In certain embodiments, the sense strand includes 15, 16, 17, 18, 19, or 20 nucleotides. In certain embodiments, the sense strand is 15 nucleotides in length. In certain embodiments, the sense strand is 18 nucleotides in length. In certain embodiments, the sense strand is 20 nucleotides in length. The skilled artisan will appreciate, however, that siRNAs having a length of less than 15 nucleotides or greater than 25 nucleotides can also function to mediate RNAi. Accordingly, siRNAs of such length are also within the scope of the instant invention, provided that they retain the ability to mediate RNAi. Longer RNA silencing agents have been demonstrated to elicit an interferon or Protein Kinase R (PKR) response in certain mammalian cells which may be undesirable. In certain embodiments, the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently complementary to a target sequence portion of the target gene to effect RISC-mediated cleavage of the target gene are contemplated. Accordingly, in a certain embodiment, the antisense strand of the siRNA is designed to have a sequence sufficiently complementary to a portion of the target. For example, the antisense strand may have 100% complementarity to the target site. However, 100% complementarity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% complementarity, between the antisense strand and the target RNA sequence is contemplated. The present application has the advantage of being able to tolerate certain sequence variations to enhance efficiency and specificity of RNAi. In one embodiment, the antisense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and the percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6 (\log 10[Na+])+0.41(\% G+C)-(600/N)$, where N is the number of bases in the hybrid, and [Na+] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant PRNP mRNA), the siRNA may be incubated with target cDNA (e.g., PRNP cDNA) in a *Drosophila*-based in vitro mRNA expression system. Radiolabeled with $^{32}P$, newly synthesized target mRNAs (e.g., PRNP mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-PRNP siRNAs may be designed to target any of the target sequences described supra. Said siRNAs comprise an antisense strand, which is sufficiently complementary with the target sequence to mediate silencing of the target sequence. In certain embodiments, the RNA silencing agent is a siRNA.

In certain embodiments, the siRNA comprises a sense strand comprising a sequence set forth in Table 7 and Table 8, and an antisense strand comprising a sequence set forth in Table 7 and Table 8.

Sites of siRNA-mRNA complementation are selected, which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of an PRNP mRNA to direct gene silencing either by RNAi or translational repression. siRNA-like molecules are designed in the same way as siRNA molecules, but the degree of sequence identity between the sense strand and target RNA approximates that observed between a miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an PRNP target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides, which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the present application are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the PRNP target sequence. In certain embodiments, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are about 15 to about 50 nucleotides in length. In certain embodiments, the two stem portions are about 18 or 19 to about 21, 22, 23, 24, 25, 30, 35, 37, 38, 39, or 40 or more nucleotides in length. In certain embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. In certain embodiments, a loop consists of or comprises a "tetraloop" sequence. Exemplary tetraloop sequences include, but are not limited to, the sequences GNRA, where N is any nucleotide and R is a purine nucleotide, GGGG, and UUUU.

In certain embodiments, shRNAs of the present application include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., PRNP mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include, in the duplex stem, the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between a miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In certain embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), a miRNA, to mediate RNA silencing. Accordingly, the methods described herein obviate the need to introduce foreign molecules (e.g., siRNAs) to mediate RNA silencing. Second, the RNA-silencing agents and the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In certain embodiments, the tethers have the formula T-L-μ, wherein T is an mRNA targeting moiety, L is a linking moiety, and μ is a miRNA recruiting moiety. Any one or more moiety may be double stranded. In certain embodiments, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly, depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a certain embodiment, the targeting moiety is about 15 to about 25 nucleotides in length.

The miRNA recruiting moiety, as described above, is capable of associating with a miRNA. According to the present application, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties can be oligonucleotide moieties comprising a sufficient number of nucleotides, such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., PRNP gene expression) can be modulated using oligonucleotide-based compounds comprising two or more single stranded antisense oligonucleotides that are linked through their 5'-ends that allow the presence of two or more accessible 3'-ends to effectively inhibit or decrease PRNP gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2'hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of a gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula $HO-(CH_2)_o-CH(OH)-(CH_2)_p-OH$, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula $HO-(CH_2)m-C(O)NH-CH_2-CH(OH)-CH_2-NHC(O)-(CH_2)_m-OH$, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods, such as phosphoramidate or H-phosphonate chemistry, which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate, carboxymethyl ester, or a combination of these and other internucleotide linkages between the 5' end of one nucleotide and the 3' end of another nucleotide, in which the 5' nucleotide phosphodiester linkage has been replaced with any number of chemical groups.

V. Modified Anti-PRNP RNA Silencing Agents

In certain aspects of the invention, an RNA silencing agent (or any portion thereof) of the present application, as described supra, may be modified, such that the activity of the agent is further improved. For example, the RNA silencing agents described in Section II supra, may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the present application may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is contemplated because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In certain embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In certain embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In certain embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S'5) of said RNA silencing agent.

In one embodiment, the asymmetry of an RNA silencing agent of the present application may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In certain embodiments, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In certain embodiments, the base pair is selected from the group consisting of an I:A, I:U and I:C. In yet another embodiment, the asymmetry of an RNA silencing agent of the invention may be enhanced such that there is at least one base pair comprising a modified nucleotide. In certain embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. In order to enhance the stability, the 3'-residues may be stabilized against degradation, e.g., they may be selected such that they consist of purine nucleotides, such as adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified. In certain embodiments, the RNA silencing agents may be fully chemically modified, i.e., 100% of the nucleotides are chemically modified. In another aspect, the present application features RNA silencing agents comprising 2'-OH ribose groups that are at least 80% chemically modified. In certain embodiments, the RNA silencing agents comprise 2'-OH ribose groups that are about 80%, 85%, 90%, 95%, or 100% chemically modified.

In certain embodiments, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Moreover, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In certain embodiments, the modifications are 2'-fluoro, 2'-amino and/or 2'-thio modifications. Modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a certain embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a certain embodiment, the 2' moiety is a methyl group such that the linking moiety is a 2'-O-methyl oligonucleotide.

In a certain embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone, which is highly resistant to nuclease digestion and imparts improved binding specificity to the molecule (Nielsen, et al., Science, (2001), 254: 1497-1500).

Also contemplated are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes can be located on the sense strand and not the antisense strand in certain embodiments); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' 0 Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications. In certain embodiments, the RNA silencing agent is a dsRNA comprising an antisense strand and sense strand. In certain embodiments, the antisense strand comprises at least about 70% 2'-O-methyl nucleotide modifications. In certain embodiments, the antisense strand comprises between about 70% and about 90% 2'-O-methyl nucleotide modifications. In certain embodiments, the sense strand comprises at least about 70% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications.

2'-O-methyl rich RNA silencing agents and specific chemical modification patterns are further described in U.S. Ser. No. 16/550,076 (filed Aug. 23, 2019) and U.S. Ser. No. 62/891,185 (filed Aug. 23, 2019), each of which is incorporated herein by reference.

Internucleotide Linkage Modifications

In certain embodiments, at least one internucleotide linkage, intersubunit linkage, or nucleotide backbone is modified in the RNA silencing agent. In certain embodiments, all of the internucleotide linkages in the RNA silencing agent are modified. In certain embodiments, the modified internucleotide linkage comprises a phosphorothioate internucleotide linkage. In certain embodiments, the RNA silencing agent comprise 1, 2, 3, 4, 5, 6, 7, 8, 9, 10, 11, 12, 13, 14, 15, 16, 17, 18, 19, 20, 21, 22, 23, 24, or 25 phosphorothioate internucleotide linkages. In certain embodiments, the RNA silencing agent comprises 4-16 phosphorothioate internucleotide linkages. In certain embodiments, the RNA silencing agent comprises 8-13 phosphorothioate internucleotide linkages. In certain embodiments, the RNA silencing agent is a dsRNA comprising an antisense strand and a sense strand, each comprising a 5' end and a 3' end. In certain embodiments, the nucleotides at positions 1 and 2 from the 5' end of sense strand are connected to adjacent ribonucleotides via phosphorothioate internucleotide linkages. In certain embodiments, the nucleotides at positions 1 and 2 from the 3' end of sense strand are connected to adjacent ribonucleotides via phosphorothioate internucleotide linkages. In certain embodiments, the nucleotides at positions 1 and 2 from the 5' end of antisense strand are connected to adjacent ribonucleotides via phosphorothioate internucleotide linkages. In certain embodiments, the nucleotides at positions 1-2 to 1-8 from the 3' end of antisense strand are connected to adjacent ribonucleotides via phosphorothioate internucleotide linkages. In certain embodiments, the nucleotides at positions 1-2, 1-3, 1-4, 1-5, 1-6, 1-7, or 1-8 from the 3' end of antisense strand are connected to adjacent ribonucleotides via phosphorothioate internucleotide linkages. In certain embodiments, the nucleotides at positions 1-2 to 1-7 from the 3' end of antisense strand are connected to adjacent ribonucleotides via phosphorothioate internucleotide linkages.

In one aspect, the disclosure provides a modified oligonucleotide, said oligonucleotide having a 5' end, a 3' end, that is complementary to a target, wherein the oligonucleotide comprises a sense and antisense strand, and at least one modified intersubunit linkage of Formula (I):

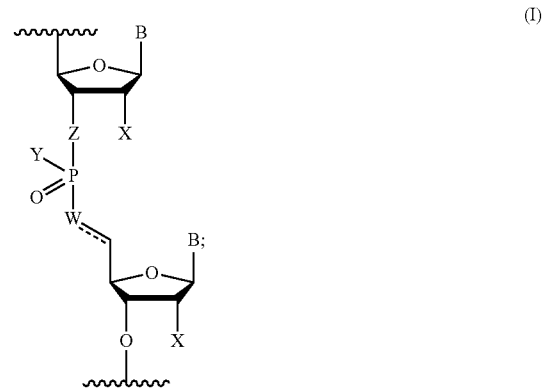

wherein:
  B is a base pairing moiety;
  W is selected from the group consisting of O, $OCH_2$, OCH, $CH_2$, and CH;
  X is selected from the group consisting of halo, hydroxy, and $C_{1-6}$ alkoxy;
  Y is selected from the group consisting of $O^-$, OH, OR, $NH^-$, $NH_2$, $S^-$, and SH;
  Z is selected from the group consisting of O and $CH_2$;
  R is a protecting group; and
  === is an optional double bond.

In certain embodiments, when W is CH, === is a double bond.

In certain embodiments, when W is selected from the group consisting of O, $OCH_2$, OCH, $CH_2$, === is a single bond.

In an embodiment of Formula (I), when Y is $O^-$, either Z or W is not O.

In an embodiment of Formula (I), Z is $CH_2$ and W is $CH_2$. In another embodiment, the modified intersubunit linkage of Formula (I) is a modified intersubunit linkage of Formula (II):

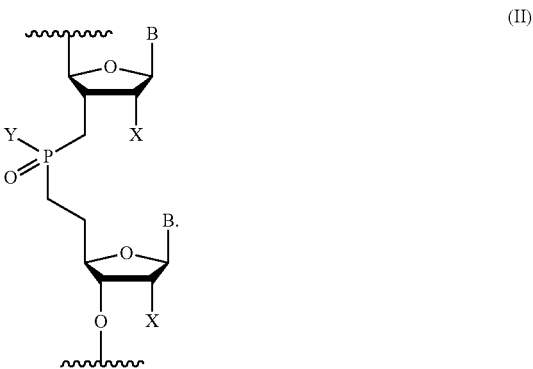

In an embodiment of Formula (I), Z is CH$_2$ and W is O. In another embodiment, wherein the modified intersubunit linkage of Formula (I) is a modified intersubunit linkage of Formula (III):

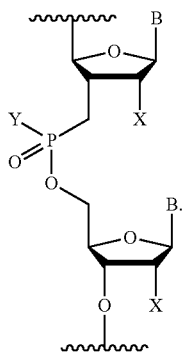

(III)

In an embodiment of Formula (I), Z is O and W is CH$_2$. In another embodiment, the modified intersubunit linkage of Formula (I) is a modified intersubunit linkage of Formula (IV):

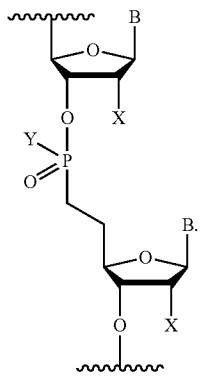

(IV)

In an embodiment of Formula (I), Z is O and W is CH. In another embodiment, the modified intersubunit linkage of Formula (I) is a modified intersubunit linkage of Formula V:

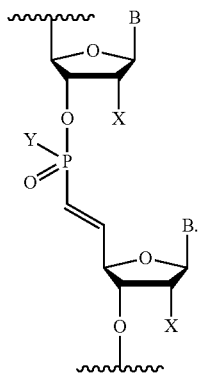

(V)

In an embodiment of Formula (I), Z is O and W is OCH$_2$. In another embodiment, the modified intersubunit linkage of Formula (I) is a modified intersubunit linkage of Formula VI:

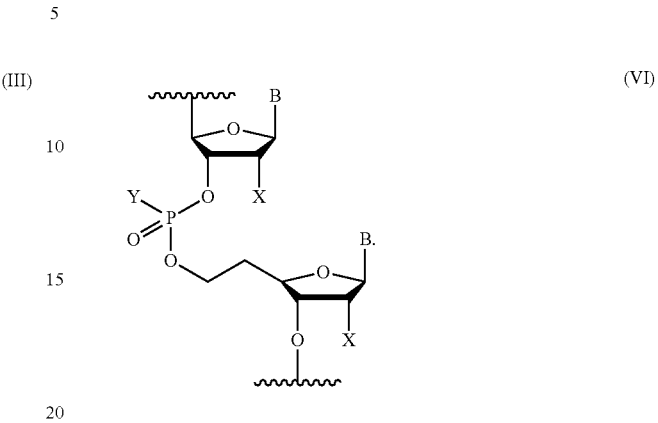

(VI)

In an embodiment of Formula (I), Z is CH$_2$ and W is CH. In another embodiment, the modified intersubunit linkage of Formula (I) is a modified intersubunit linkage of Formula VII:

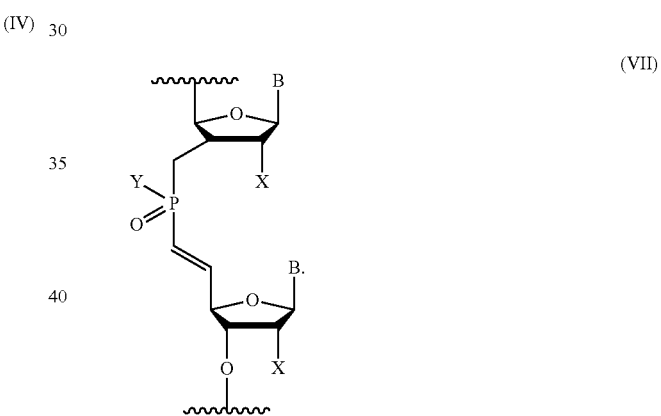

(VII)

In an embodiment of Formula (I), the base pairing moiety B is selected from the group consisting of adenine, guanine, cytosine, and uracil.

In an embodiment, the modified oligonucleotide is incorporated into siRNA, said modified siRNA having a 5' end, a 3' end, that is complementary to a target, wherein the siRNA comprises a sense and antisense strand, and at least one modified intersubunit linkage of any one or more of Formula (I), Formula (II), Formula (III), Formula (IV), Formula (V), Formula (VI), or Formula (VII).

In an embodiment, the modified oligonucleotide is incorporated into siRNA, said modified siRNA having a 5' end, a 3' end, that is complementary to a target and comprises a sense and antisense strand, wherein the siRNA comprises at least one modified intersubunit linkage is of Formula VIII:

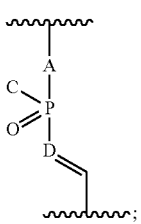

(VIII)

wherein:
D is selected from the group consisting of O, OCH$_2$, OCH, CH$_2$, and CH;
C is selected from the group consisting of O$^-$, OH, OR$^1$, NW, NH$_2$, S$^-$, and SH;
A is selected from the group consisting of O and CH$_2$;
R$^1$ is a protecting group;
=== is an optional double bond; and
the intersubunit is bridging two optionally modified nucleosides.

In an embodiment, when C is O$^-$, either A or D is not O.
In an embodiment, D is CH$_2$. In another embodiment, the modified intersubunit linkage of Formula VIII is a modified intersubunit linkage of Formula (IX):

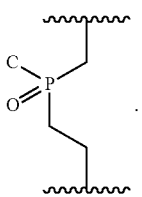

(IX)

In an embodiment, D is O. In another embodiment, the modified intersubunit linkage of Formula VIII is a modified intersubunit linkage of Formula (X):

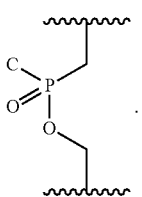

(X)

In an embodiment, D is CH$_2$. In another embodiment, the modified intersubunit linkage of Formula (VIII) is a modified intersubunit linkage of Formula (XI):

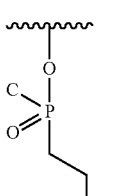

(XI)

In an embodiment, D is CH. In another embodiment, the modified intersubunit linkage of Formula VIII is a modified intersubunit linkage of Formula (XII):

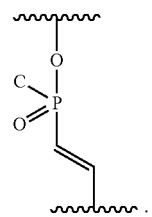

(XII)

In another embodiment, the modified intersubunit linkage of Formula (VII) is a modified intersubunit linkage of Formula (XIV):

(XIV)

In an embodiment, D is OCH$_2$. In another embodiment, the modified intersubunit linkage of Formula (VII) is a modified intersubunit linkage of Formula (XIII):

(XIII)

In another embodiment, the modified intersubunit linkage of Formula (VII) is a modified intersubunit linkage of Formula (XXa):

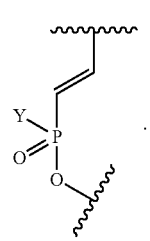

(XXa)

In an embodiment of the modified siRNA linkage, each optionally modified nucleoside is independently, at each occurrence, selected from the group consisting of adenosine, guanosine, cytidine, and uridine.

In certain exemplary embodiments of Formula (I), W is O. In another embodiment, W is $CH_2$. In yet another embodiment, W is CH.

In certain exemplary embodiments of Formula (I), X is OH. In another embodiment, X is $OCH_3$. In yet another embodiment, X is halo.

In a certain embodiment of Formula (I), the modified siRNA does not comprise a 2'-fluoro substituent.

In an embodiment of Formula (I), Y is $O^-$. In another embodiment, Y is OH. In yet another embodiment, Y is OR. In still another embodiment, Y is $NH^-$. In an embodiment, Y is $NH_2$. In another embodiment, Y is S. In yet another embodiment, Y is SH.

In an embodiment of Formula (I), Z is O. In another embodiment, Z is $CH_2$.

In an embodiment, the modified intersubunit linkage is inserted on position 1-2 of the antisense strand. In another embodiment, the modified intersubunit linkage is inserted on position 6-7 of the antisense strand. In yet another embodiment, the modified intersubunit linkage is inserted on position 10-11 of the antisense strand. In still another embodiment, the modified intersubunit linkage is inserted on position 19-20 of the antisense strand. In an embodiment, the modified intersubunit linkage is inserted on positions 5-6 and 18-19 of the antisense strand.

In an exemplary embodiment of the modified siRNA linkage of Formula (VIII), C is $O^-$. In another embodiment, C is OH. In yet another embodiment, C is OR'. In still another embodiment, C is $NH^-$. In an embodiment, C is $NH_2$. In another embodiment, C is S. In yet another embodiment, C is SH.

In an exemplary embodiment of the modified siRNA linkage of Formula (VIII), A is O. In another embodiment, A is $CH_2$. In yet another embodiment, C is OR'. In still another embodiment, C is $NH^-$. In an embodiment, C is $NH_2$. In another embodiment, C is $S^-$. In yet another embodiment, C is SH.

In a certain embodiment of the modified siRNA linkage of Formula (VIII), the optionally modified nucleoside is adenosine. In another embodiment of the modified siRNA linkage of Formula (VIII), the optionally modified nucleoside is guanosine. In another embodiment of the modified siRNA linkage of Formula (VIII), the optionally modified nucleoside is cytidine. In another embodiment of the modified siRNA linkage of Formula (VIII), the optionally modified nucleoside is uridine.

In an embodiment of the modified siRNA linkage, wherein the linkage is inserted on position 1-2 of the antisense strand. In another embodiment, the linkage is inserted on position 6-7 of the antisense strand. In yet another embodiment, the linkage is inserted on position 10-11 of the antisense strand. In still another embodiment, the linkage is inserted on position 19-20 of the antisense strand. In an embodiment, the linkage is inserted on positions 5-6 and 18-19 of the antisense strand.

In certain embodiments of Formula (I), the base pairing moiety B is adenine. In certain embodiments of Formula (I), the base pairing moiety B is guanine. In certain embodiments of Formula (I), the base pairing moiety B is cytosine. In certain embodiments of Formula (I), the base pairing moiety B is uracil.

In an embodiment of Formula (I), W is O. In an embodiment of Formula (I), W is $CH_2$. In an embodiment of Formula (I), W is CH.

In an embodiment of Formula (I), X is OH. In an embodiment of Formula (I), X is $OCH_3$. In an embodiment of Formula (I), X is halo.

In an exemplary embodiment of Formula (I), the modified oligonucleotide does not comprise a 2'-fluoro substituent.

In an embodiment of Formula (I), Y is $O^-$. In an embodiment of Formula (I), Y is OH. In an embodiment of Formula (I), Y is OR. In an embodiment of Formula (I), Y is $NH^-$. In an embodiment of Formula (I), Y is $NH_2$. In an embodiment of Formula (I), Y is $S^-$. In an embodiment of Formula (I), Y is SH.

In an embodiment of Formula (I), Z is O. In an embodiment of Formula (I), Z is $CH_2$.

In an embodiment of the Formula (I), the linkage is inserted on position 1-2 of the antisense strand. In another embodiment of Formula (I), the linkage is inserted on position 6-7 of the antisense strand. In yet another embodiment of Formula (I), the linkage is inserted on position 10-11 of the antisense strand. In still another embodiment of Formula (I), the linkage is inserted on position 19-20 of the antisense strand. In an embodiment of Formula (I), the linkage is inserted on positions 5-6 and 18-19 of the antisense strand.

Modified intersubunit linkages are further described in U.S. Ser. No. 62/824,136 (filed Mar. 26, 2019), U.S. Ser. No. 62/826,454 (filed Mar. 29, 2019), and U.S. Ser. No. 62/864,792 (filed Jun. 21, 2019), each of which is incorporated herein by reference.

4) Conjugated Functional Moieties

In other embodiments, RNA silencing agents may be modified with one or more functional moieties. A functional moiety is a molecule that confers one or more additional activities to the RNA silencing agent. In certain embodiments, the functional moieties enhance cellular uptake by target cells (e.g., neuronal cells). Thus, the invention includes RNA silencing agents which are conjugated or unconjugated (e.g., at its 5' and/or 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a certain embodiment, the functional moiety is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, a a cationic dye (e.g., Cy3). In an exemplary embodiment, the lipophilic moiety is cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

In certain embodiments, the functional moieties may comprise one or more ligands tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These can be located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or a metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine, has an increased affinity for the HIV Rev-response element (RRE). In some embodiments, the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, either directly or indirectly, via an intervening tether, to a ligand-conjugated carrier. In certain embodiments, the coupling is through a covalent bond. In certain embodiments, the ligand is attached to the carrier via an intervening tether. In certain embodiments, a ligand alters the distribution, targeting or lifetime of an RNA silencing agent into which it is incorporated. In certain embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNAc) or derivatives thereof, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP. In certain embodiments, the ligand is GalNAc or a derivative thereof.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-kB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF□), interleukin-1 beta, or gamma interferon. In one aspect, the ligand is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a certain embodiment, the lipid based ligand binds HSA. A lipid-based ligand can bind HSA with a sufficient affinity such that the conjugate will be distributed to a non-kidney tissue. However, it is contemplated that the affinity not be so strong that the HSA-ligand binding cannot be reversed. In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These can be useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In certain embodiments, the agent is amphipathic. An exemplary agent is a peptide such as that or antennopedia. If the agent is a peptide, it can be modified, including a peptidylmimetic, invertomers, non-peptide or pseudo-peptide linkages, and use of D-amino acids. The helical agent can be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

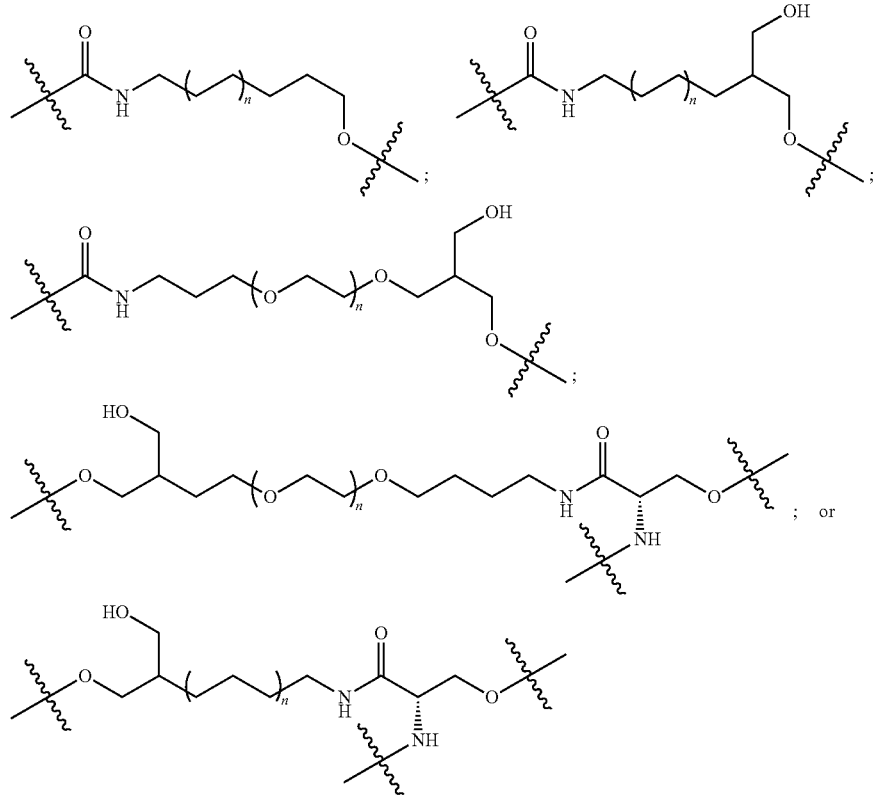

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of:

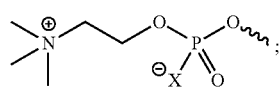 (Zc1)

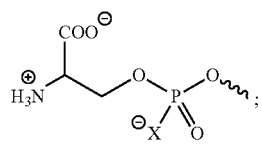 (Zc2)

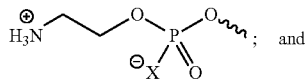 (Zc3)

and

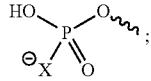 (Zc4)

wherein X is O, S or $BH_3$.

The various functional moieties of the disclosure and means to conjugate them to RNA silencing agents are described in further detail in WO2017/030973A1 and WO2018/031933A2, incorporated herein by reference.

VI. Branched Oligonucleotides

Two or more RNA silencing agents as disclosed supra, for example oligonucleotide constructs such as anti-PRNP siRNAs, may be connected to one another by one or more moieties independently selected from a linker, a spacer and a branching point, to form a branched oligonucleotide RNA silencing agent. In certain embodiments, the branched oligonucleotide RNA silencing agent consists of two siRNAs to form a di-branched siRNA ("di-siRNA") scaffolding for delivering two siRNAs. In representative embodiments, the nucleic acids of the branched oligonucleotide each comprise an antisense strand (or portions thereof), wherein the antisense strand has sufficient complementarity to a target mRNA (e.g., PRNP mRNA) to mediate an RNA-mediated silencing mechanism (e.g. RNAi).

In exemplary embodiments, the branched oligonucleotides may have two to eight RNA silencing agents attached through a linker. The linker may be hydrophobic. In an embodiment, branched oligonucleotides of the present application have two to three oligonucleotides. In an embodiment, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has two to ten nucleotides.

In certain embodiments, branched oligonucleotides are characterized by three properties: (1) a branched structure, (2) full metabolic stabilization, and (3) the presence of a single-stranded tail comprising phosphorothioate linkers. In certain embodiments, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. In some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm~37° C.) for fast dissociation upon internalization of the branched structure into the cell.

The Di-siRNA branched oligonucleotides may comprise chemically diverse conjugates, such as the functional moieties described above. Conjugated bioactive ligands may be used to enhance cellular specificity and to promote membrane association, internalization, and serum protein binding. Examples of bioactive moieties to be used for conjugation include DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including siRNAs, ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

VII. Compound of Formula (I)

In another aspect, provided herein is a branched oligonucleotide compound of formula (I):

$$L\text{-}(N)_n \tag{I}$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof.

Moiety N is an RNA duplex comprising a sense strand and an antisense strand; and n is 2, 3, 4, 5, 6, 7 or 8. In an embodiment, the antisense strand of N comprises a sequence substantially complementary to a PRNP nucleic acid sequence of any one of SEQ ID NOs: 1-12, 95, 112, 114, 124, 181, or 182, as recited in Table 4, Table 5, and Table 9. In further embodiments, N includes strands that are capable of targeting one or more of a PRNP nucleic acid sequence selected from the group consisting of any one of SEQ ID NOs: 13-38, 217, 234, 236, 246, 303, or 304, as recited in Tables 6-8, and 10. The sense strand and antisense strand may each independently comprise one or more chemical modifications.

In an embodiment, the compound of formula (I) has a structure selected from formulas (I-1)-(I-9) of Table 1.

TABLE 1

| | |
|---|---|
| N—L—N | (I-1) |
| N—S—L—S—N | (I-2) |

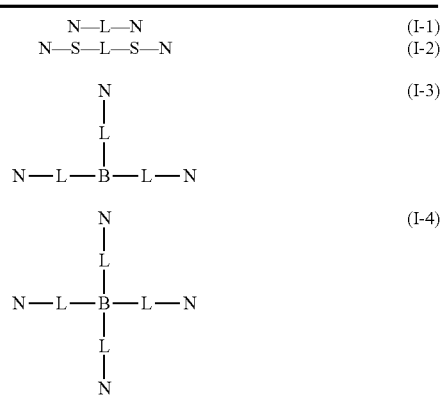

TABLE 1-continued

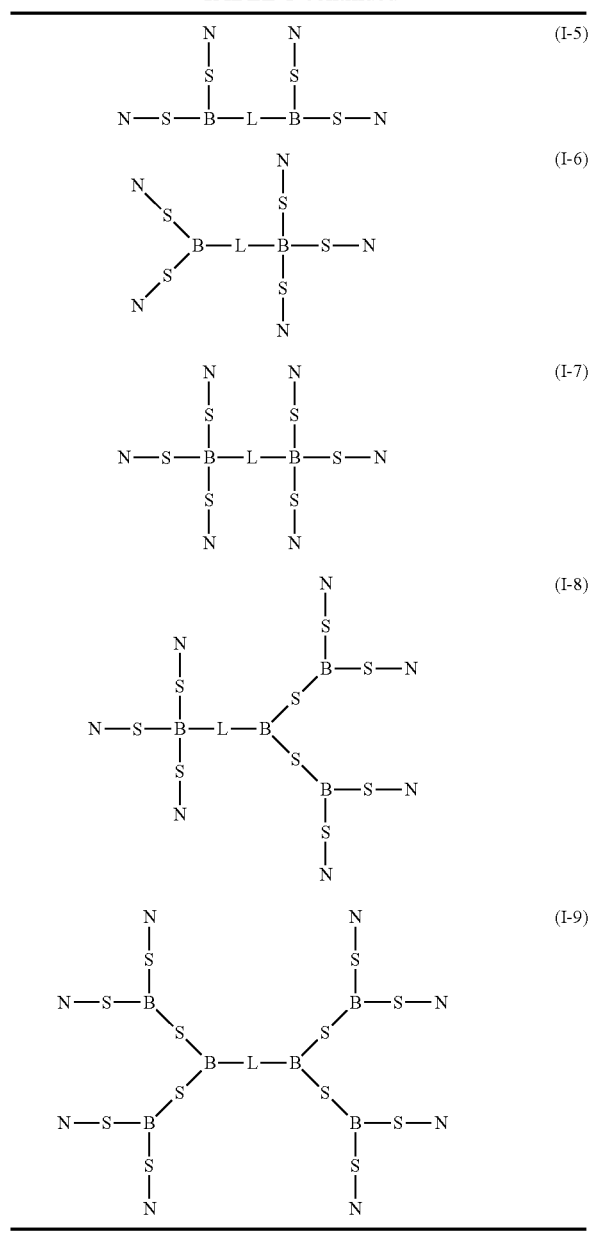

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of:

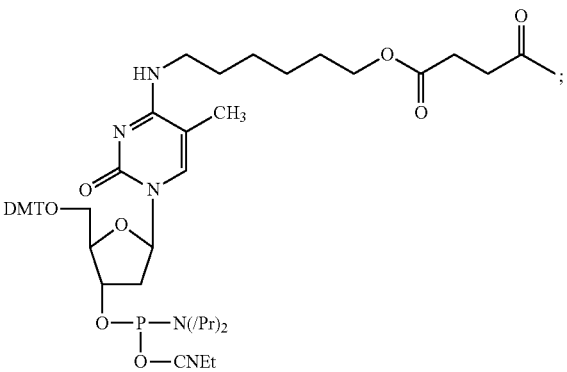

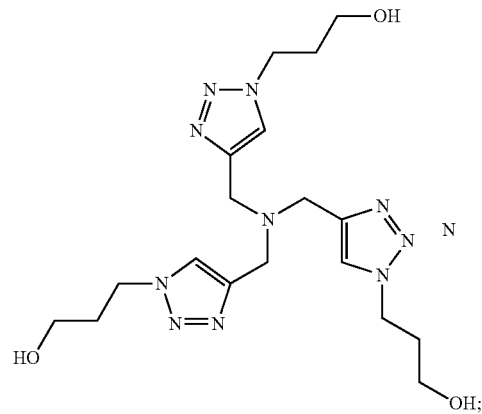

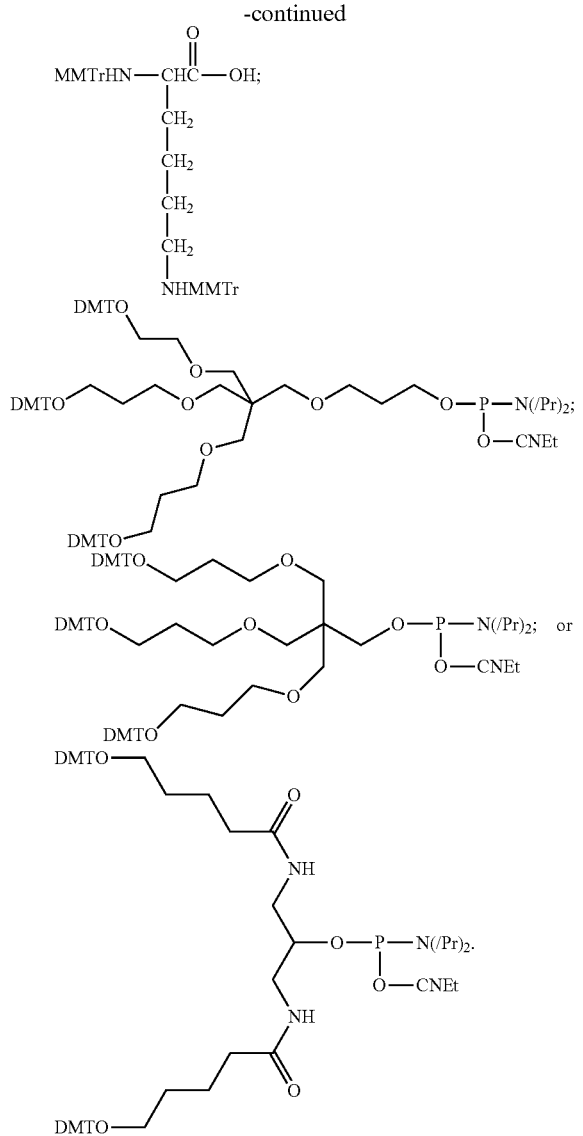

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

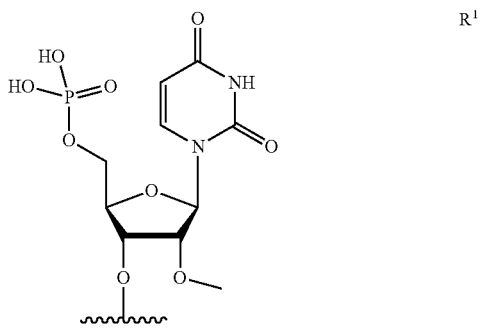

$R^1$

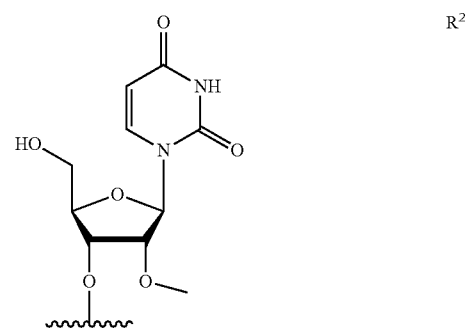

$R^2$

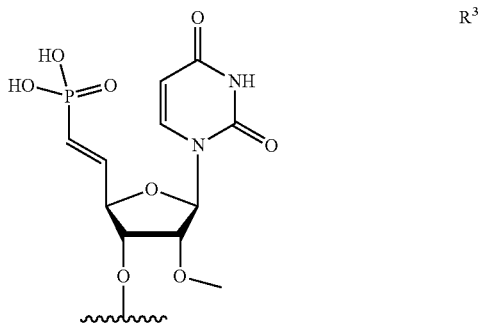

$R^3$

TABLE 2-continued

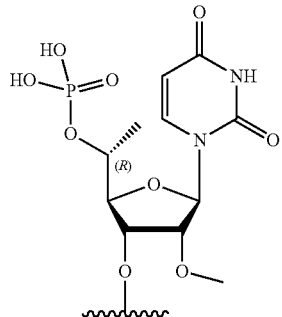

R⁴

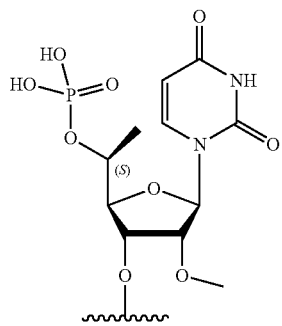

R⁵

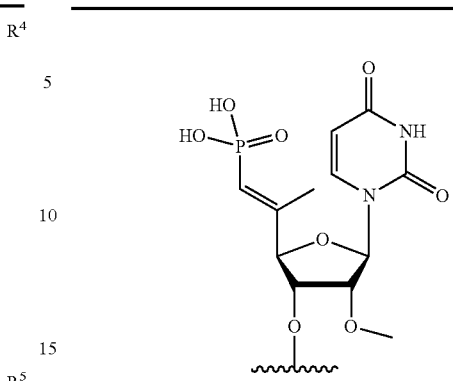

R⁸

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) has the structure of formula

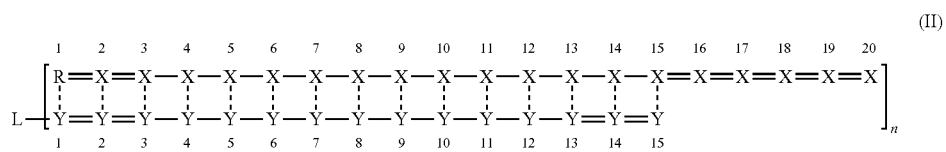

(II)

TABLE 2-continued

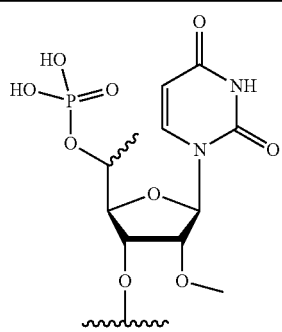

R⁶

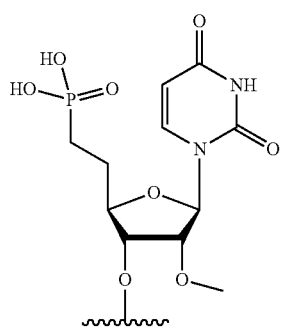

R⁷ wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; = represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula

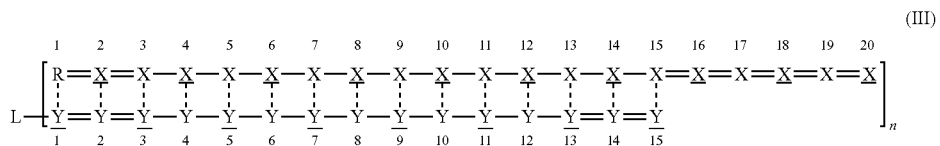

(III)

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

(IV)

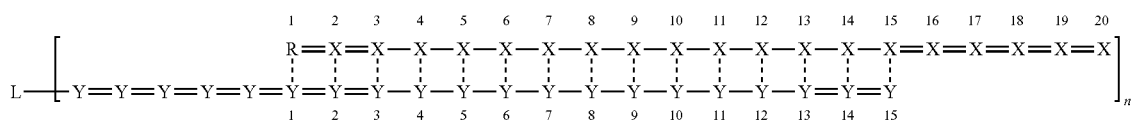

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; = represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (IV) are chemically-modified nucleotides. In other embodiments, >95%, >90%, >85%, >80%, >75%, >70%, >65%, >60%, >55% or >50% of X's of the structure of formula (IV) are chemically-modified nucleotides.

Structure of Formula (V)

In an embodiment, the compound of formula (I) has the structure of formula (V):

(V)

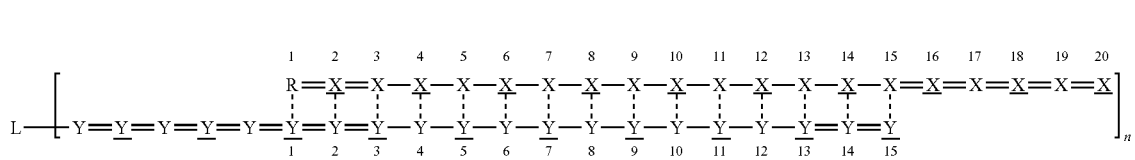

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

formula (VI), L has the structure of L2. In an embodiment of the structure of formula (VI), L has the structure of L2.

Delivery System

In a third aspect, provided herein is a delivery system for therapeutic nucleic acids having the structure of formula (VI):

$$L\text{-}(cNA)_n \qquad (VI)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of

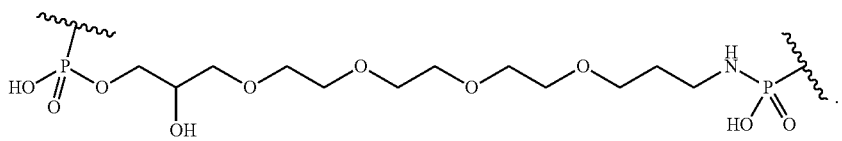

(L1)

In an embodiment of L1, R is R³ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a

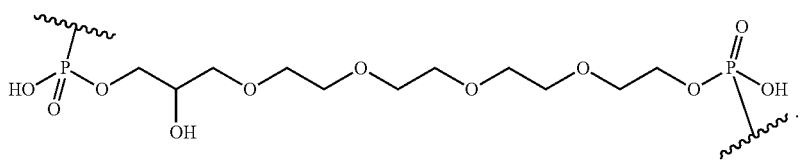

(L2)

In an embodiment of L2, R is R3 and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VI) has a structure selected from formulas (VI-1)-(VI-9) of Table 3:

TABLE 3

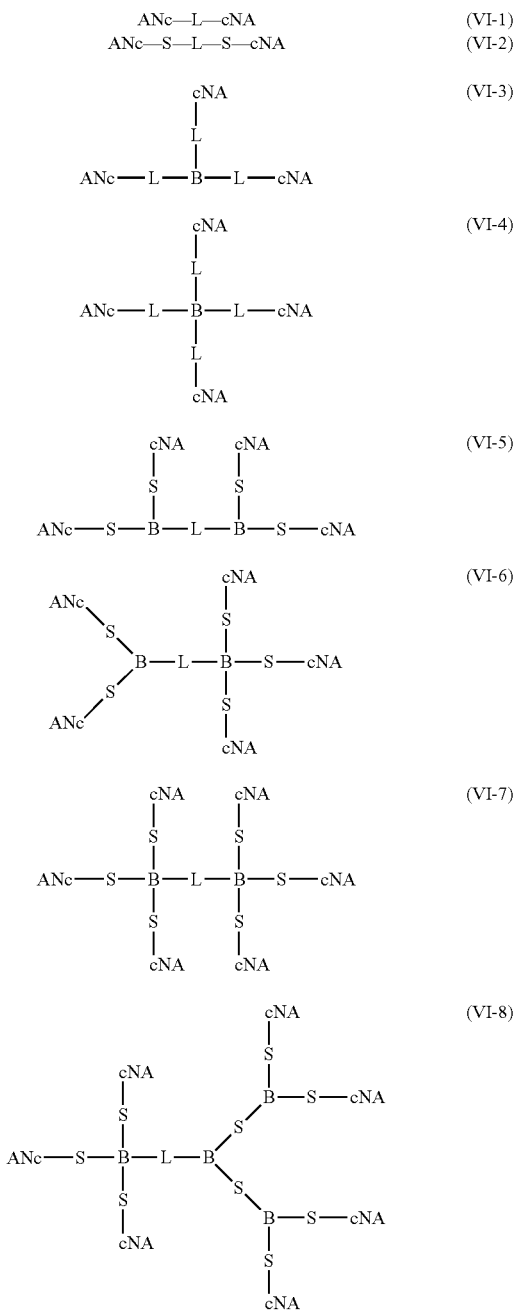

TABLE 3-continued

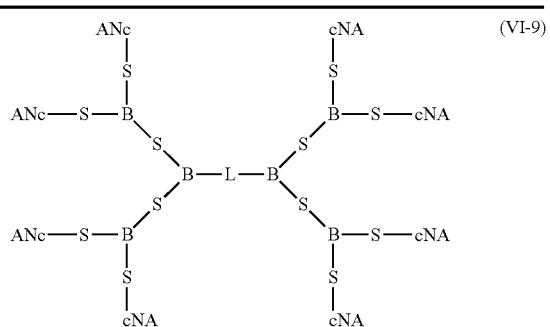

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a sequence substantially complementary to a PRNP nucleic acid sequence of any one of SEQ ID NOs: 1-12, 95, 112, 114, 124, 181, or 182, as recited in Table 4 and Table 5. In further embodiments, NA includes strands that are capable of targeting one or more of a PRNP nucleic acid sequence selected from the group consisting of any one of SEQ ID NOs: 13-38, 217, 234, 236, 246, 303, or 304, as recited in Tables 6-8, 10.

Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 15 contiguous nucleotides. In an embodiment, each NA independently comprises 15-25 contiguous nucleotides. In an embodiment, each NA independently comprises 15 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides. In an embodiment, each NA independently comprises 21 contiguous nucleotides. In an embodiment, each NA independently comprises 22 contiguous nucleotides. In an embodiment, each NA independently comprises 23 contiguous nucleotides. In an embodiment, each NA independently comprises 24 contiguous nucleotides. In an embodiment, each NA independently comprises 25 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR.

In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is $R^3$ and n is 2. In another embodiment, the delivery system has a structure selected from formulas (I), (II), (III), (IV), (V), (VI), further comprising a linker of structure L1 wherein R is $R^3$ and n is 2. In another embodiment, the delivery system has a structure selected from formulas (I), (II), (III), (IV), (V), (VI), further comprising a linker of structure L2 wherein R is $R^3$ and n is 2.

In an embodiment of the delivery system, the target of delivery is selected from the group consisting of: brain, liver, skin, kidney, spleen, pancreas, colon, fat, lung, muscle, and thymus. In one embodiment, the target of delivery is the brain. In another embodiment, the target of delivery is the striatum of the brain. In another embodiment, the target of delivery is the cortex of the brain. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery is the lung. In one embodiment, the target of delivery is the muscle. In one embodiment, the target of delivery is the thymus. In one embodiment, the target of delivery is the spinal cord.

In certain embodiments, compounds of the invention are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phosorothioated single oligonucleotides containing at least 3, phosphorothioated bonds. In certain embodiments, the phoshorothioated single oligonucleotides contain 4-20 phosphorothioated bonds.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Branched oligonucleotides, including synthesis and methods of use, are described in greater detail in WO2017/132669, incorporated herein by reference.

Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an PRNP target sequence) is tested for its ability to specifically degrade mutant mRNA (e.g., PRNP mRNA and/or the production of PRNP protein) in cells, such as cells in the central nervous system. In certain embodiments, cells in the central nervous system include, but are not limited to, neurons (e.g., striatal or cortical neuronal clonal lines and/or primary neurons), glial cells, and astrocytes. Also suitable for cell-based validation assays are other readily transfectable cells, for example, HeLa cells or COS cells. Cells are transfected with human wild type or mutant cDNAs (e.g., human wild type or mutant PRNP cDNA). Standard siRNA, modified siRNA or vectors able to produce siRNA from U-looped mRNA are co-transfected. Selective reduction in target mRNA (e.g., PRNP mRNA) and/or target protein (e.g., PRNP protein) is measured. Reduction of target mRNA or protein can be compared to levels of target mRNA or protein in the absence of an RNAi agent or in the presence of an RNAi agent that does not target PRNP mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In certain embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VIII. Methods of Treatment

In one aspect, the present invention provides for both prophylactic and therapeutic methods of treating a subject at risk of (or susceptible to) a disease or disorder caused, in whole or in part, by trinucleotide repeats. In one embodiment, the disease or disorder is such that PRNP levels in the central nervous system (CNS) have been found to be predictive of neurodegeneration progression. In another embodiment, the disease or disorder is a polyglutamine disorder. In a certain embodiment, the disease or disorder one in which reduction of PRNP in the CNS reduces clinical manifestations seen in neurodegenerative diseases such as Huntington's disease.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a CNS cell expressing PRNP with a therapeutic agent (e.g., a RNAi agent or vector or transgene encoding same) that is specific for a target sequence within the gene (e.g., PRNP target sequences of Tables 4-6), such that sequence specific interference with the gene is achieved. These methods can be performed in vitro (e.g., by culturing the cell with the agent) or, alternatively, in vivo (e.g., by administering the agent to a subject).

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

In embodiments of this aspect, the prophylactic and therapeutic methods are directed to treating or managing neurodegenerative diseases or disorders in which reduction of PRNP in the CNS reduces abnormal amyloid accumulation. In a non-limiting example, the RNA silencing agent is a branched oligonucleotide as described in sections VI and VII herein, which is administered to a patient diagnosed as having or at risk for developing Huntington's disease or an amyloid-related neurodegenerative disease or disorder such as Alzheimer's disease, cerebral amyloid angiopathy, or mild-to-moderate cognitive impairment. The patient can be treated following diagnosis, at varying stage of the disease, or as a prophylactic measure in instances where genetic traits, family history, or other factors put the patient at risk for the neurodegenerative disease or disorder. Successful dosage amounts and schedules may be established and monitored by metrics indicative of effective treatment, for example the extent of inhibition, delay, prevention or reduction of symptoms such as cognitive decline, beta-amyloid plaque formation in the brain, and neurodegeneration which are detected following the initiation of treatment.

In one embodiment, the patient is diagnosed as having or at risk for developing Huntington's disease, and the patient is otherwise in good health. Treatment is carried out by administering a Di-siRNA$^{PRNP}$, i.e., a branched oligonucleotide including two nucleic acids each between 15 and 35 bases in length. Each nucleic acid features a sequence substantially complementary to a portion of PRNP mRNA, e.g., one or more of the target sequences set forth in Tables 4-6. The two nucleic acids are connected to one another by, for example, a linker, spacer, or branching point. Each of the nucleic acids may independently be single stranded (ss) RNA or double stranded (ds) RNA. For example, each of the nucleic acids may independently be an antisense molecule or a GAPMER.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. In certain embodiments, dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. In another embodiment, the dosage can be in the order of about 10 mg to about 50 mg per organ, or about 20 mg to about 30 mg per organ. The dosage can be an amount effective to treat or prevent a neurodegenerative disease or disorder, e.g., AD or ALS. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 10 mg/kg of body weight per day, e.g., 10, 1, 0.1, 0.01, 0.001, or 0.00001 mg per kg of bodyweight per day. In certain embodiments, the maintenance doses are administered no more than once every 5, 10, or 30 days, although more frequent dosing may be required. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

IX. Pharmaceutical Compositions and Methods of Administration

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain embodiments, isotonic agents, for example, sugars, polyalcohols such as mannitol, sorbitol, sodium chloride, may be included in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, some methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are contemplated. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds can lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 jag to 1000 mg may be administered; in some embodiments, 10, 30, 100 or 1000 µg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), Supra.

Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection. One route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-PRNP RNA silencing agent of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the invention can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mager I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mager I, Wood M J. (2013). Exosomes for targeted siRNA delivery across biological barriers. Adv Drug Deliv Rev. 2013 March; 65(3): 391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. In certain embodiments, compositions for intrathecal or intraventricular administration do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are contemplated. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are useful include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A contemplated group of carbohydrates includes lactose, trehalose, raffinose maltodextrins, and mannitol. Suitable polypeptides include aspartame. Amino acids include alanine and glycine.

Suitable pH adjusters or buffers include organic salts prepared from organic acids and bases, such as sodium citrate, sodium ascorbate, and the like.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

X. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. In Vitro Identification of PRNP Targeting Sequences

The PRNP gene was used as a target for mRNA knockdown. A panel of siRNAs targeting several different sequences of the human and mouse PRNP mRNA was developed and screened in A549 human carcinoma cells or N2A mouse cells in vitro and compared to untreated control cells. SiRNAs were designed to target the open reading frame (ORF) and 3' untranslated region (3'UTR). The siRNAs were each tested at a concentration of 1.5 µM and the mRNA was evaluated with the QuantiGene gene expression assay (ThermoFisher, Waltham, MA) at the 72 hours timepoint. FIG. 1 reports the results of the screen against human PRNP mRNA and FIG. 2 reports the results of the screen against mouse PRNP mRNA. Of the panel of siRNA target sites tested, 12 were identified that yielded potent and efficacious silencing of PRNP mRNA relative to % untreated control.

Figure 2:
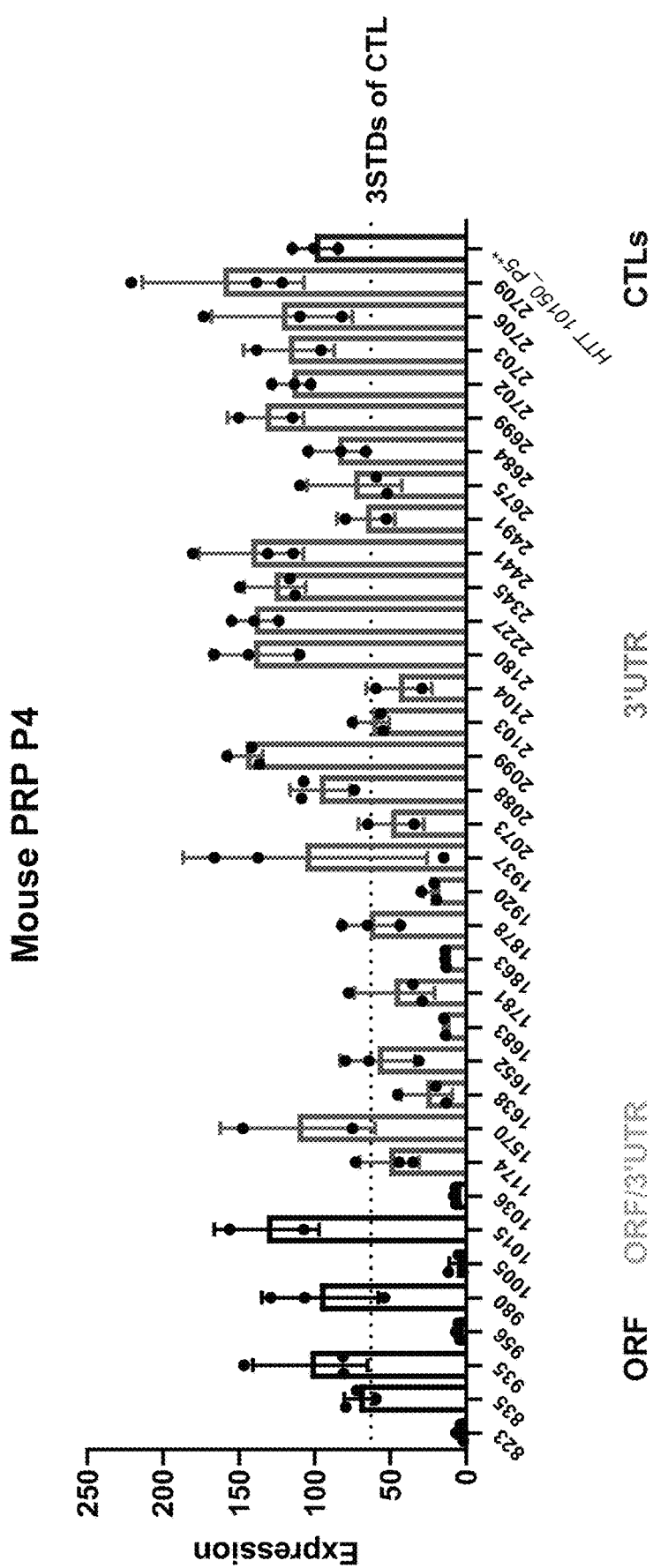
FIG. 2 depicts a screen of siRNAs targeting sequences of mouse PRNP mRNA in N2A mouse cells.

Table 4 and Table 6 below recites the human PRNP target sequences that demonstrated reduced PRNP mRNA expression relative to % untreated control. Table 5 below recites the cross-species and mouse PRNP target sequences that demonstrated reduced PRNP mRNA expression relative to % untreated control. The cross-species targets are found in both the human and mouse PRNP mRNA and may be useful in comparative in vivo studies. Table 7 below recites the antisense and sense strands of the 12 siRNAs that resulted in potent and efficacious silencing of PRNP mRNA. The antisense strands contain a 5' uracil to enhance loading into RISC. In certain instances, the corresponding complementary adenosine in the PRNP target is not present, leading to a 5' mismatch between the antisense strand and target. As shown in the data of FIG. 1 and FIG. 2, this did not negatively impact silencing efficacy. Furthermore, several of the antisense strands contain a 3' end mismatch with the PRNP target to further enhance RISC loading, which also did not negatively impact silencing efficacy. Table 8 below recites additional antisense and sense strands with perfect complementarity to PRNP mRNA.

TABLE 4

Human PRNP mRNA targets sequences.

| ID | Targeting sequence (45 nucleotides) |
|---|---|
| Hs_835 | GGAAGUGCCAUGAGCAGGCCCAUCAUACAUUUCGGCAG UGACUAU (SEQ ID NO: 1) |
| Hs_2227 | UCAAAAACCAGAAUUAGGUCAAGUUCAUAGUUUCUGUA AUUGGCU (SEQ ID NO: 2) |
| Hs_2441 | AUGUUAUUAUUGGCUUGCACUUUGUGAGUAUUCUAUGU AAAAAUA (SEQ ID NO: 3) |
| Hs_2684 | AGGUCUUUGAAAUAUGCAUGUACUUUAUAUUUUCUAUA UUUGUAA (SEQ ID NO: 4) |
| Hs_2706 | CUUUAUAUUUUCUAUAUUUGUAACUUUGCAUGUUCUUG UUUUGUU (SEQ ID NO: 5) |

TABLE 5

Cross-species and mouse PRNP mRNA targets sequences.

| ID | Targeting sequence (45 nucleotides) |
|---|---|
| Cross_823 | GGCUACAUGCUGGGAAGUGCCAUGAGCAGGCCCAUCAU ACAUUUC (SEQ ID NO: 6) |
| Cross_956 | ACCAGAACAACUUUGUGCACGACUGCGUCAAUAUCACA AUCAAGC (SEQ ID NO: 7) |
| Cross_1005 | CACGGUCACCACAACCACCAAGGGGGAGAACUUCACCG AGACCGA (SEQ ID NO: 8) |
| Cross_1036 | UUCACCGAGACCGACGUUAAGAUGAUGGAGCGCGUGGU UGAGCAG (SEQ ID NO: 9) |
| Ms_1683 | GCUAGAAUUAGCUUCUGCCCUAUGUUUCUGUACUUCUA UUUGAAC (SEQ ID NO: 10) |
| Ms_1863 | CCAGCAGACAUAAACUGCGAUAGCUUCAGCUUGCACUG UGGAUUU (SEQ ID NO: 11) |
| Ms_1920 | AUAUAAAACAUAACUUCAAGCUUAUGUCUUCUUUUUAA AACAUCU (SEQ ID NO: 12) |

TABLE 6

Human PRNP mRNA targets sequences (20 nucleotide).

| ID | Targeting sequence (20 nucleotides) |
|---|---|
| Hs_835-20 | AGGCCCAUCAUACAUUUCGG (SEQ ID NO: 13) |
| Hs_2227-20 | AGGUCAAGUUCAUAGUUUCU (SEQ ID NO: 14) |
| Hs_2441-20 | UGCACUUUGUGAGUAUUCUA (SEQ ID NO: 15) |
| Hs_2684-20 | GCAUGUACUUUAUAUUUUCU (SEQ ID NO: 16) |
| Hs_2706-20 | AUUUGUAACUUUGCAUGUUC (SEQ ID NO: 17) |

TABLE 7

PRNP antisense and sense strand siRNA sequences used in screens of FIG. 1 and FIG. 2.

| ID | Antisense Sequence (5' - 3') | Sense Sequence (5' - 3') |
|---|---|---|
| Hs_835 | UCGAAAUGUAUGAUGGGCCUC (SEQ ID NO: 39) | CCAUCAUACAUUUCGA (SEQ ID NO: 18) |
| Hs_2227 | UGAAACUAUGAACUUGACCUU (SEQ ID NO: 40) | CAAGUUCAUAGUUUCA (SEQ ID NO: 19) |
| Hs_2441 | UAGAAUACUCACAAAGUGCAU (SEQ ID NO: 41) | CUUUGUGAGUAUUCUA (SEQ ID NO: 20) |
| Hs_2684 | UGAAAAUAUAAAGUACAUGCU (SEQ ID NO: 42) | GUACUUUAUAUUUUCA (SEQ ID NO: 21) |
| Hs_2706 | UAACAUGCAAAGUUACAAAUU (SEQ ID NO: 43) | GUAACUUUGCAUGUUA (SEQ ID NO: 22) |
| Cross_823 | UUGGGCCUGCUCAUGGCACUA (SEQ ID NO: 44) | CCAUGAGCAGGCCCAA (SEQ ID NO: 23) |
| Cross_956 | UAUAUUGACGCAGUCGUGCAG (SEQ ID NO: 45) | CGACUGCGUCAAUAUA (SEQ ID NO: 24) |
| Cross_1005 | UGAAGUUCUCCCCCUUGGUGC (SEQ ID NO: 46) | AAGGGGGAGAACUUCA (SEQ ID NO: 25) |

TABLE 7-continued

PRNP antisense and sense strand siRNA
sequences used in screens of FIG. 1 and FIG. 2.

| ID | Antisense Sequence (5' - 3') | Sense Sequence (5' - 3') |
|---|---|---|
| Cross_1036 | UCGCGCUCCAUCAUCUUAACC (SEQ ID NO: 47) | AGAUGAUGGAGCGCGA (SEQ ID NO: 26) |
| Ms_1683 | UAGUACAGAAACAUAGGGCAC (SEQ ID NO: 48) | CUAUGUUUCUGUACUA (SEQ ID NO: 27) |
| Ms_1863 | UGCAAGCUGAAGCUAUCGCAC (SEQ ID NO: 49) | AUAGCUUCAGCUUGCA (SEQ ID NO: 28) |
| Ms_1920 | UAAAGAAGACAUAAGCUUGAU (SEQ ID NO: 50) | GCUUAUGUCUUCUUUA (SEQ ID NO: 29) |

TABLE 8

PRNP antisense and sense strand siRNA
sequences - additional embodiments.

| ID | Antisense Sequence (5' - 3') | Sense Sequence (5' - 3') |
|---|---|---|
| Hs_835 | CCGAAAUGUAUGAUGGGCCUG (SEQ ID NO: 51) | CCAUCAUACAUUUCGG (SEQ ID NO: 30) |
| Hs_2227 | AGAAACUAUGAACUUGACCUA (SEQ ID NO: 52) | CAAGUUCAUAGUUUCU (SEQ ID NO: 31) |
| Hs_2441 | UAGAAUACUCACAAAGUGCAA (SEQ ID NO: 53) | CUUUGUGAGUAUUCUA (SEQ ID NO: 20) |
| Hs_2684 | AGAAAAUAUAAAGUACAUGCA (SEQ ID NO: 54) | GUACUUUAUAUUUUCU (SEQ ID NO: 32) |
| Hs_2706 | GAACAUGCAAAGUUACAAAUA (SEQ ID NO: 55) | GUAACUUUGCAUGUUC (SEQ ID NO: 33) |
| Cross_823 | AUGGGCCUGCUCAUGGCACUU (SEQ ID NO: 56) | CCAUGAGCAGGCCCAU (SEQ ID NO: 34) |
| Cross_956 | GAUAUUGACGCAGUCGUGCAC (SEQ ID NO: 57) | CGACUGCGUCAAUAUC (SEQ ID NO: 35) |
| Cross_1005 | UGAAGUUCUCCCCCUUGGUGG (SEQ ID NO: 58) | AAGGGGGAGAACUUCA (SEQ ID NO: 25) |
| Cross_1036 | ACGCGCUCCAUCAUCUUAACG (SEQ ID NO: 59) | AGAUGAUGGAGCGCGU (SEQ ID NO: 36) |
| Ms_1683 | AAGUACAGAAACAUAGGGCAG (SEQ ID NO: 60) | CUAUGUUUCUGUACUU (SEQ ID NO: 37) |
| Ms_1863 | UGCAAGCUGAAGCUAUCGCAG (SEQ ID NO: 61) | AUAGCUUCAGCUUGCA (SEQ ID NO: 28) |
| Ms_1920 | AAAAGAAGACAUAAGCUUGAA (SEQ ID NO: 62) | GCUUAUGUCUUCUUUU (SEQ ID NO: 38) |

Example 2. Expanded In Vitro Screen of PRNP Targeting Sequences

An additional screen was performed to identify further target regions of the PRNP mRNA that are efficacious for silencing PRNP gene expression.

A panel of siRNAs targeting several different sequences of the human and mouse PRNP mRNA were developed and screened in A549 human carcinoma cells or N2A mouse cells in vitro and compared to untreated control cells. The siRNAs were each tested at a concentration of 1.5 µM and the mRNA was evaluated with the QuantiGene gene expression assay (ThermoFisher, Waltham, MA) at the 72 hours timepoint. The level of Prnp expression was normalized to a housekeeping gene (Hprt). Two different siRNA chemical modification patterns were employed in the screen.

Figure 3A:
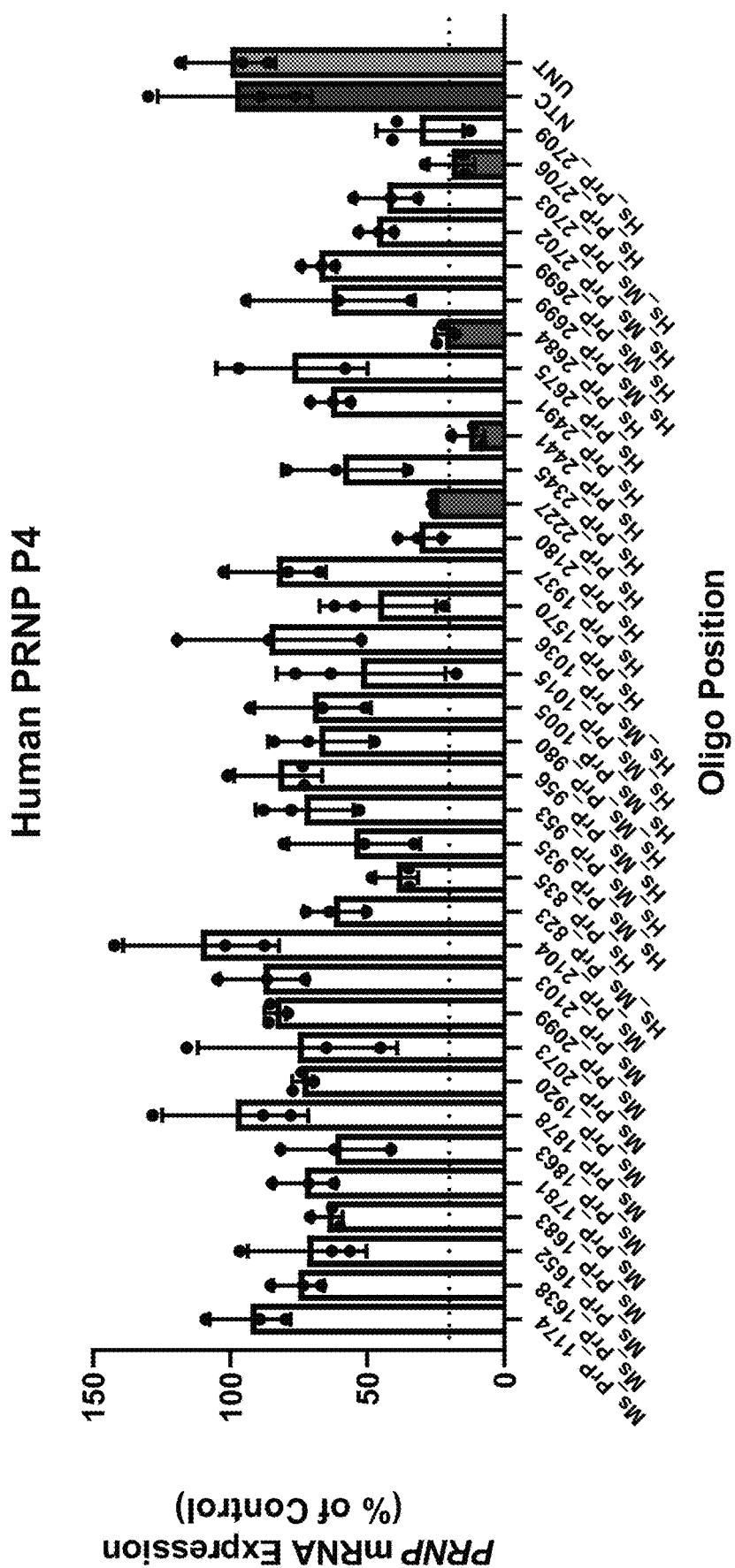
FIG. 3A-FIG. 3B depict screens of siRNAs targeting sequences of human PRNP mRNA in A549 human carcinoma cells (FIG. 3A) and mouse PRNP mRNA in N2A mouse cells (FIG. 3B), each in a P4 chemical modification pattern.
Figure 3B:
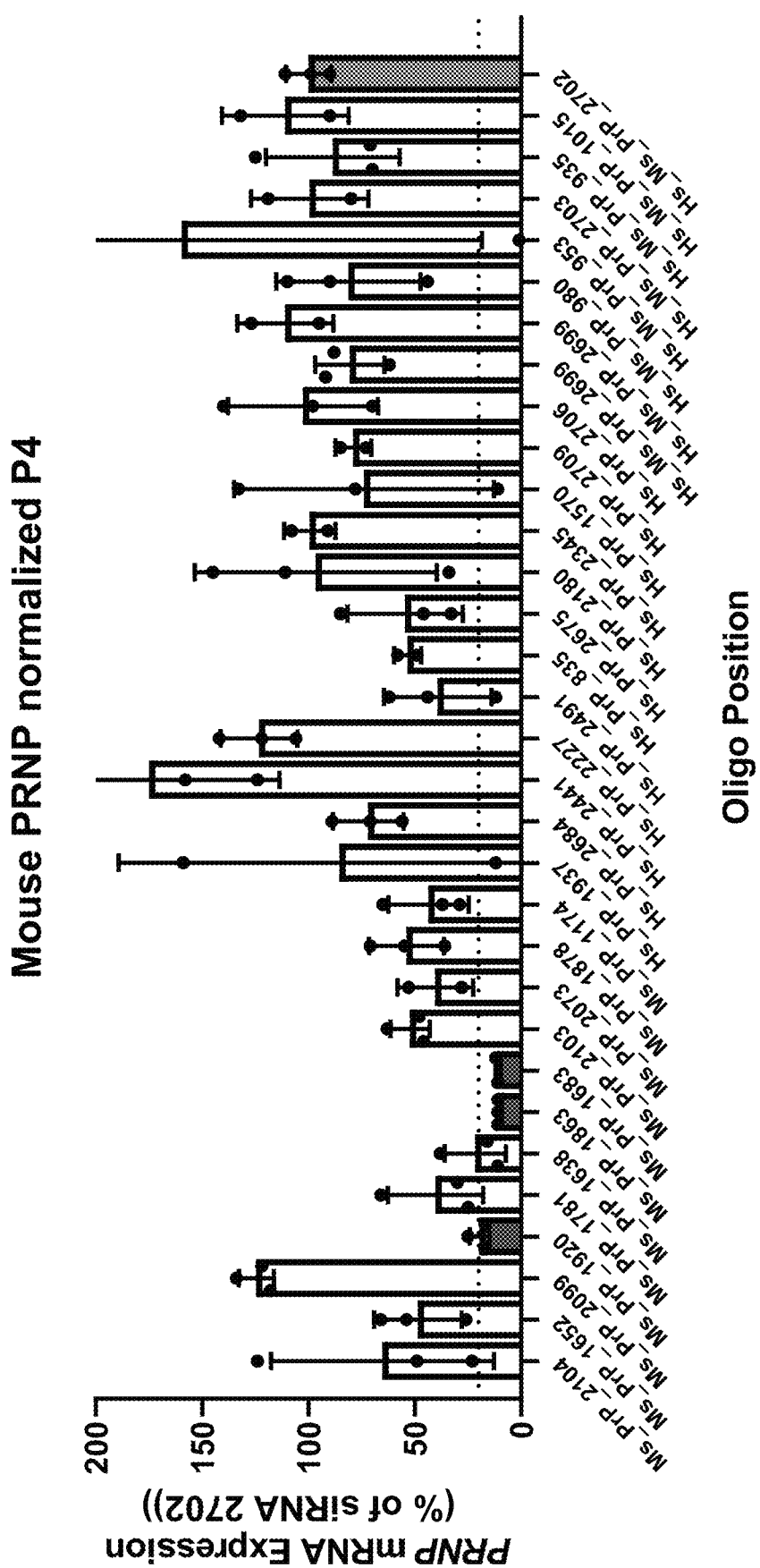

The data of FIG. 3A (A549 human carcinoma cells) and FIG. 3B (N2A mouse cells) was generated with siRNAs in the "P4" recited below:

Antisense Strand (AS), depicted from 5' to 3':
(mX)#(fX)#(mX)(mX)(mX)(mX)(mX)(mX)(mX)(mX)(mX)(mX)

(mX)(a)#(mX)#(mX)#(mX)#(mX)#(mX)#(fX)#(mX)

Sense Strand (AS), depicted from 5' to 3':
(mX)#(mX)#(mX)(mX)(mX)(mX)(mX)(mX)(mX)(mX)(mX)

(mX)#(mX)#(mX)-TegChol

Figure 4A:
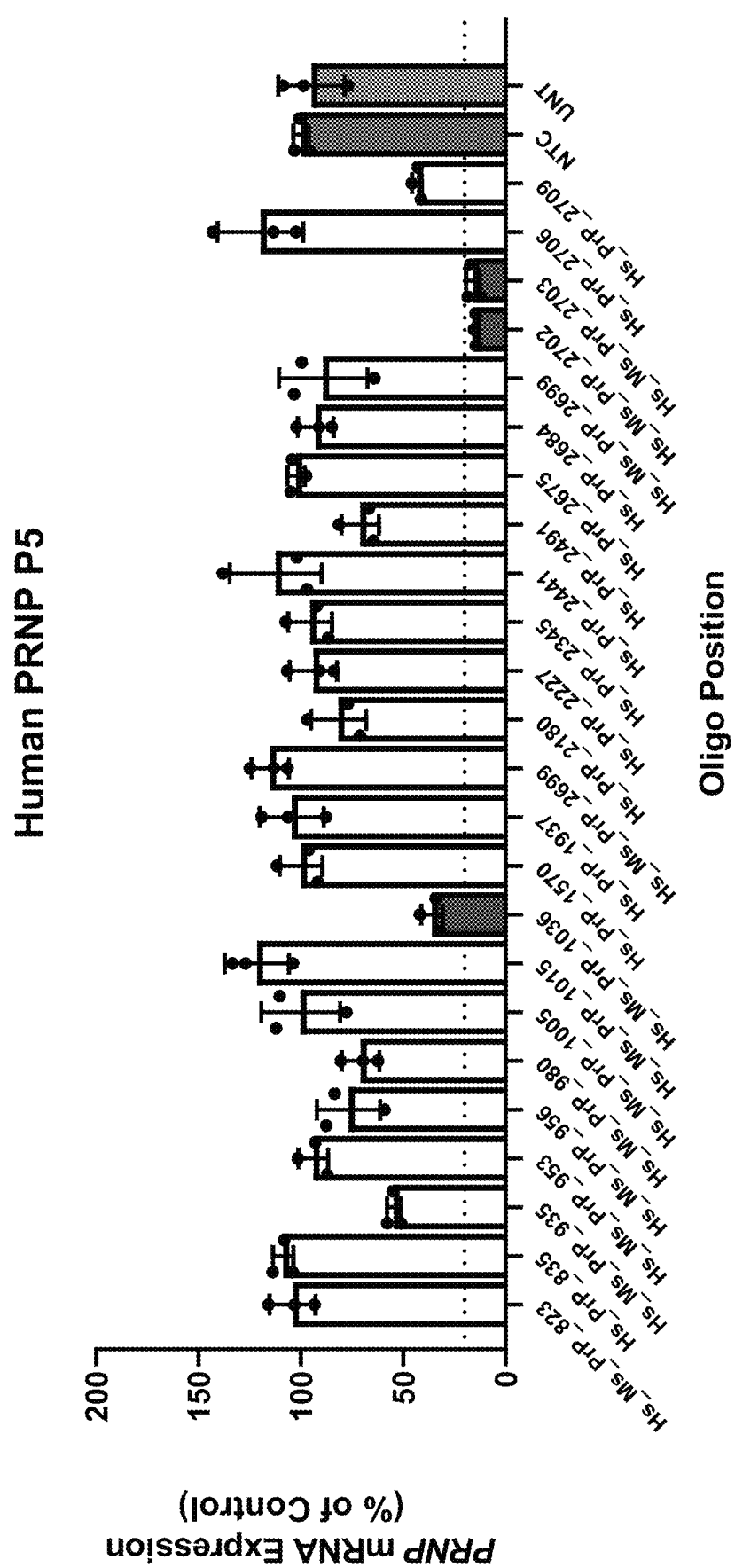
FIG. 4A-FIG. 4B depict screens of siRNAs targeting sequences of human PRNP mRNA in A549 human carcinoma cells (FIG. 4A) and mouse PRNP mRNA in N2A mouse cells (FIG. 4B), each in a P5 chemical modification pattern.
Figure 4B:
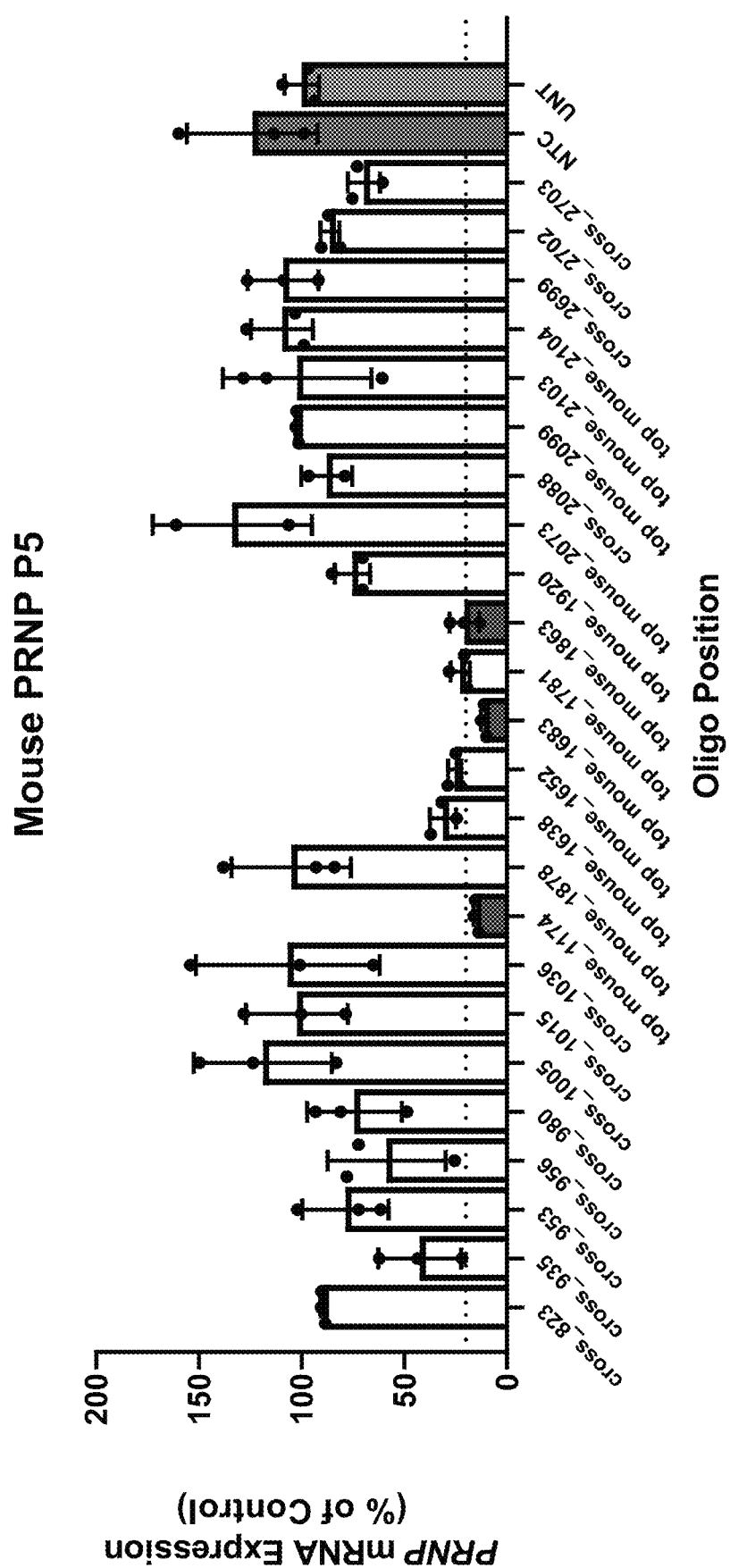

The data of FIG. 4A (A549 human carcinoma cells) and FIG. 4B (N2A mouse cells) was generated with siRNAs in the "P5" recited below:

Antisense Strand (AS), depicted from 5' to 3':
(mX)#(fX)#(mX)(mX)(mX)(fX)(mX)(mX)(mX)(mX)(mX)(mX)

(mX)(fX)#(mX)#(fX)#(mX)#(mX)#(mX)#(fX)#(mX)

Sense Strand (AS), depicted from 5' to 3':
(mX)#(mX)#(mX)(mX)(mX)(fX)(fX)(fX)(mX)(fX)(mX)(mX)

(mX)(mX)#(mX)#(mX)-TegChol

In the P4 and P5 pattern recited above, "m" corresponds to a 2'-O-methyl modified nucleotide, "f" corresponds to a 2'-fluoro modified nucleotide, "X" corresponds to any of nucleotides A, U, G, or C, "#" corresponds to a phosphorothioate internucleotide linkage, and "TegChol" corresponds to a cholesterol conjugated moiety.

Moreover, the P4 or P5 pattern can further comprise a 5' phosphate or a 5' vinyl phosphate.

Figure 5:
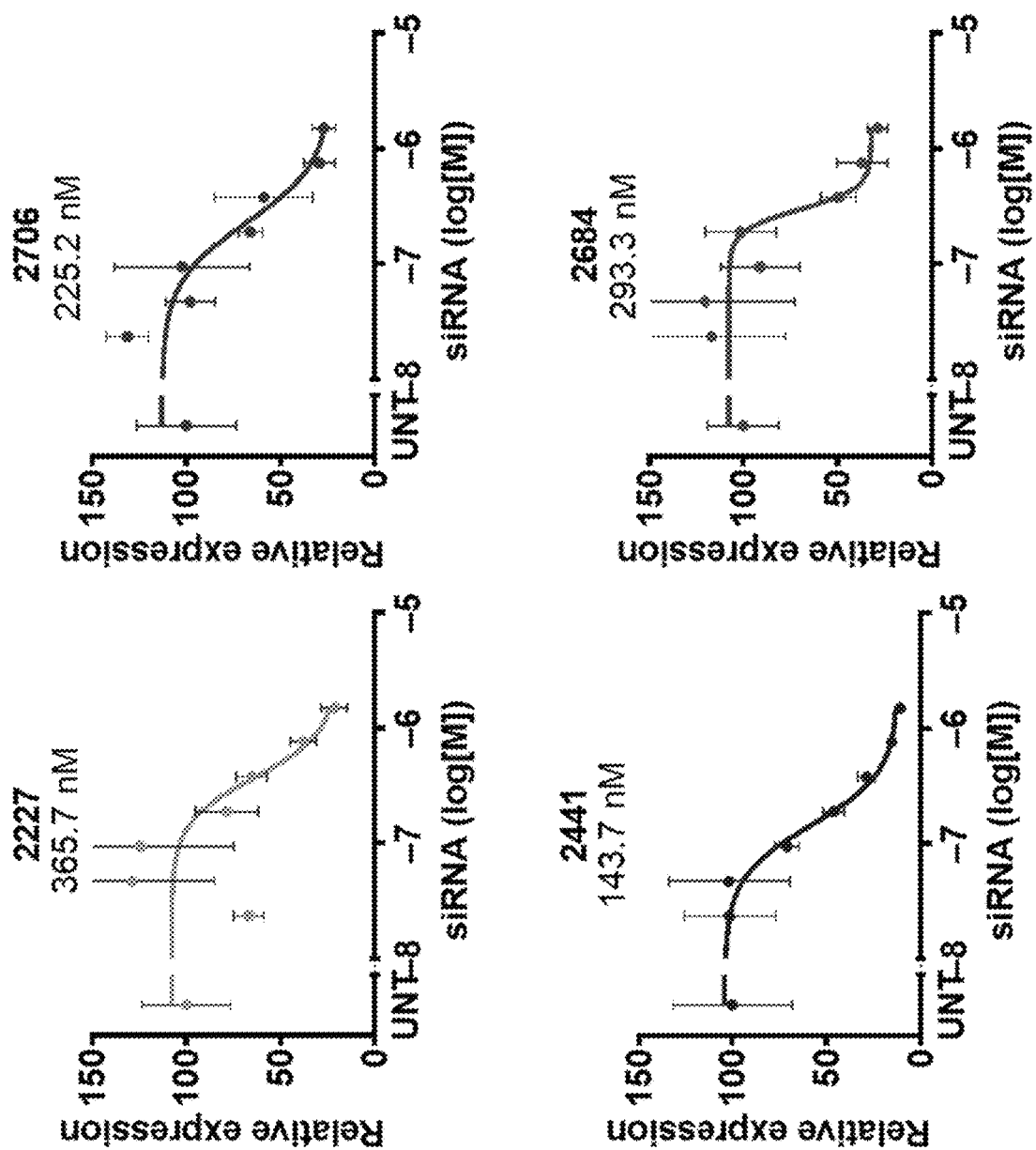
FIG. 5 depicts dose response curves for siRNAs 2227, 2706, 2441, and 2684 in A549 human carcinoma cells.
Figure 6:
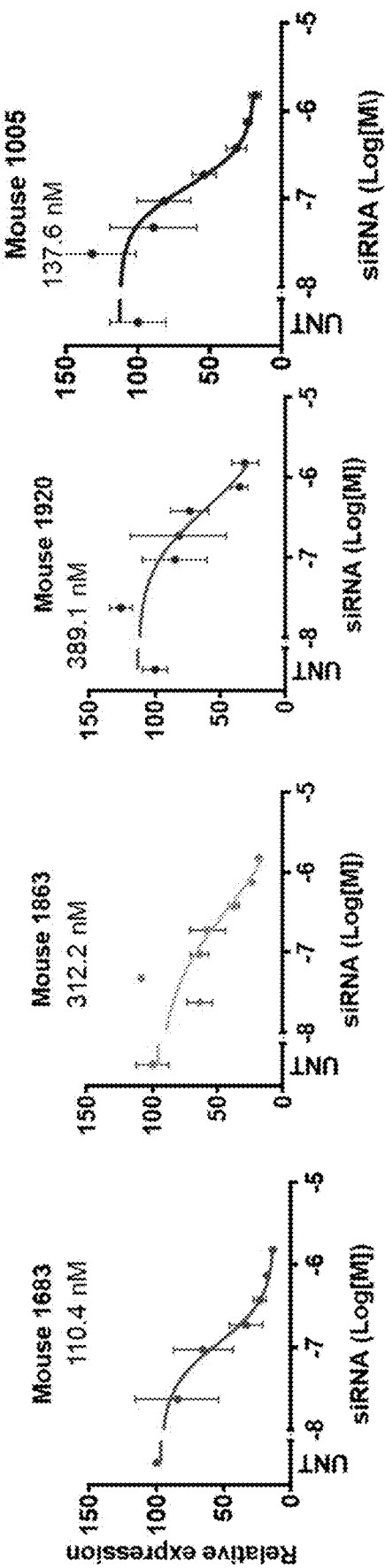
FIG. 6 depicts dose response curves for siRNAs 1683, 1863, 1920, and 1005 in N2A mouse cells.

Following the initial screen, a dose response was performed with select P4 pattern siRNAs that displayed efficacious silencing of PRNP mRNA. Cells were incubated with oligonucleotides, in serial dilution from 1.5-0.02304. The assay was performed in triplicate. Three days post treatment, cells where lysed and the level of PRNP expression was evaluated using QuantiGene2 Assay (Affymetrics). The level of PRNP expression was normalized to a housekeeping gene (HPRT). Both A549 human carcinoma cells (FIG. 5) and N2A mouse cells (FIG. 6) were used.

Figure 7:
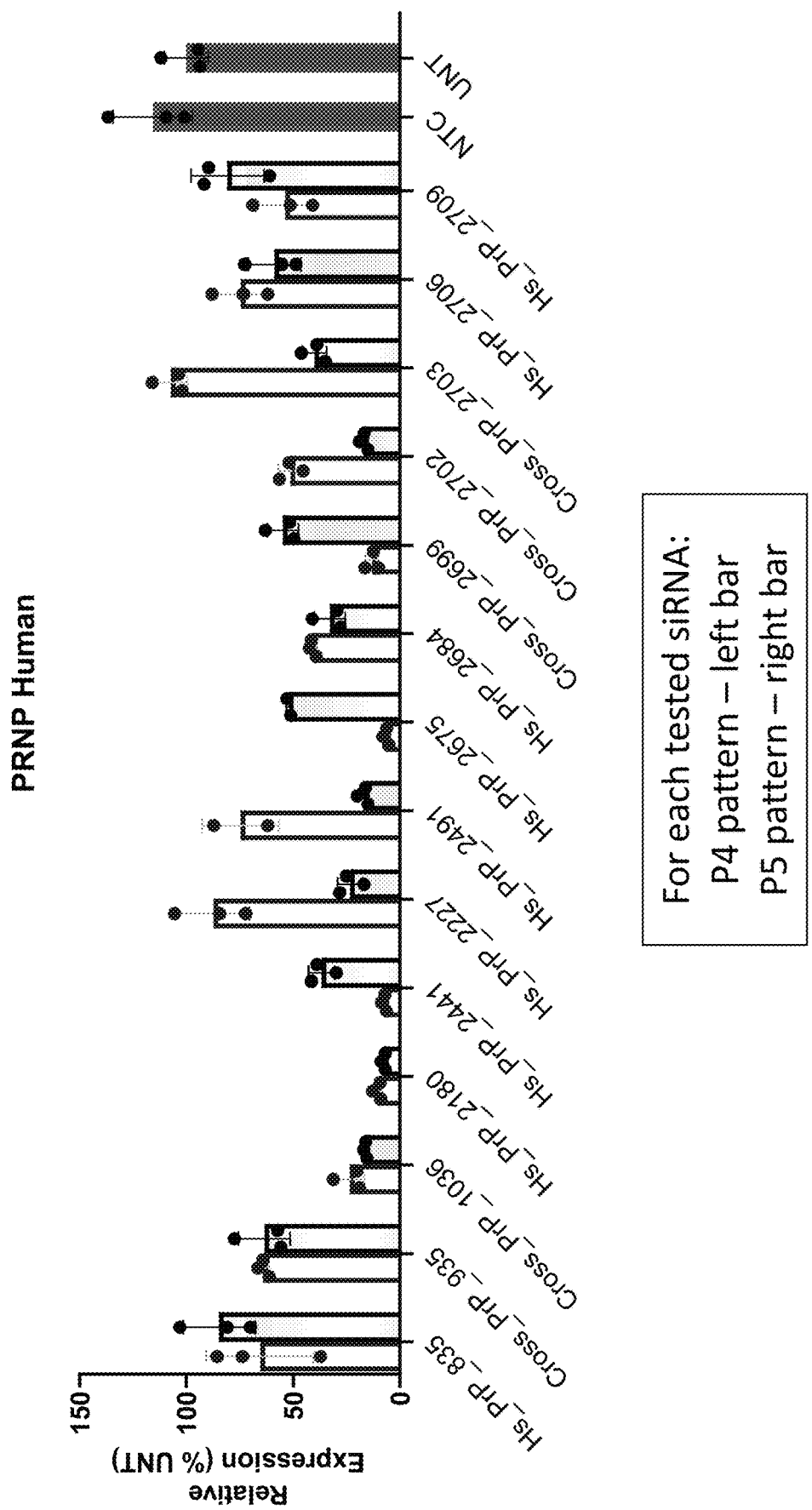
FIG. 7 depicts a comparison of siRNA silencing efficacy between siRNAs in a P4 pattern and P5 pattern.
Figure 8:
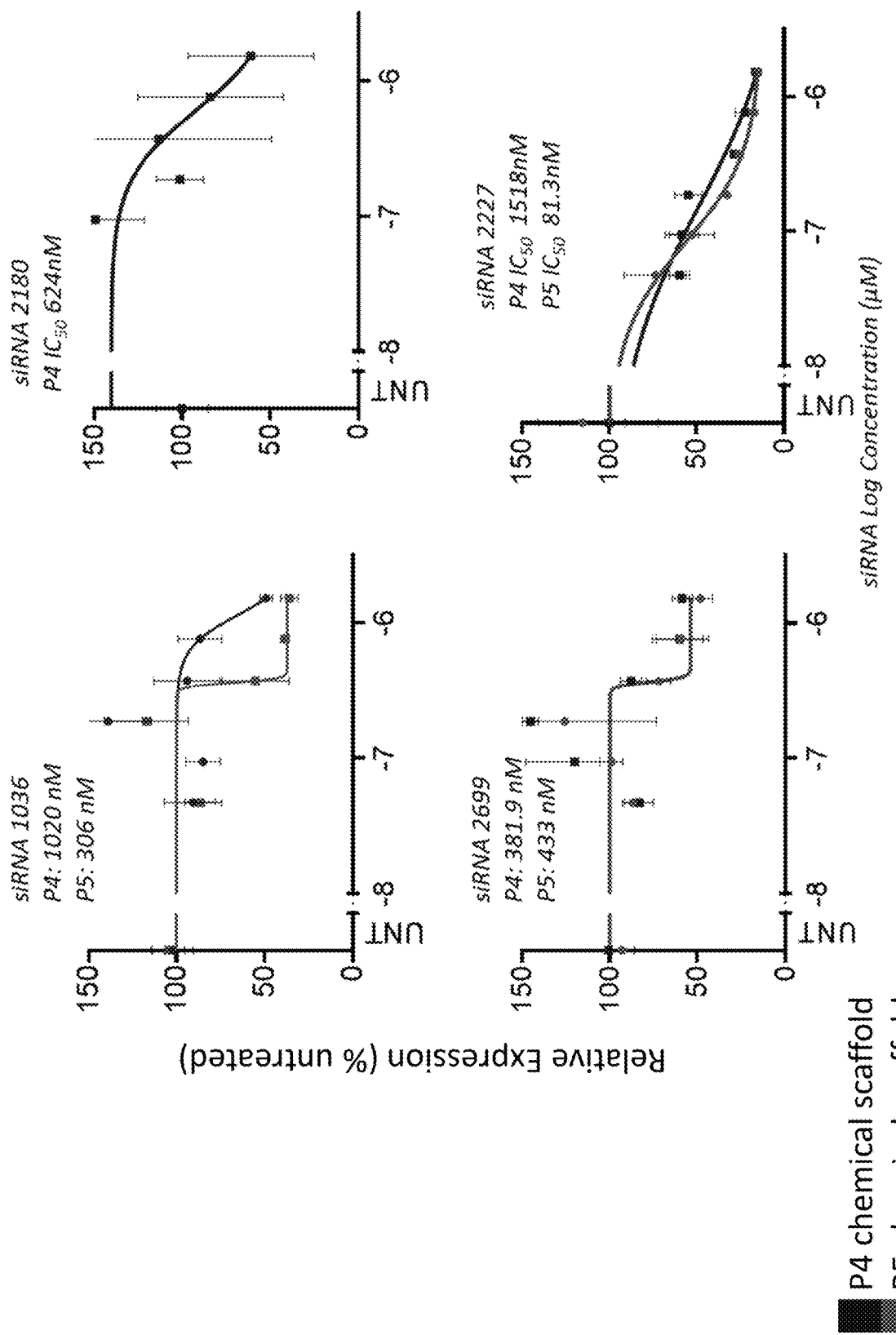
FIG. 8 depicts a comparison of siRNAs 1036, 2180, 2227, and 2699 in the dose response between siRNAs in a P4 pattern and P5 pattern.
Figure 9:
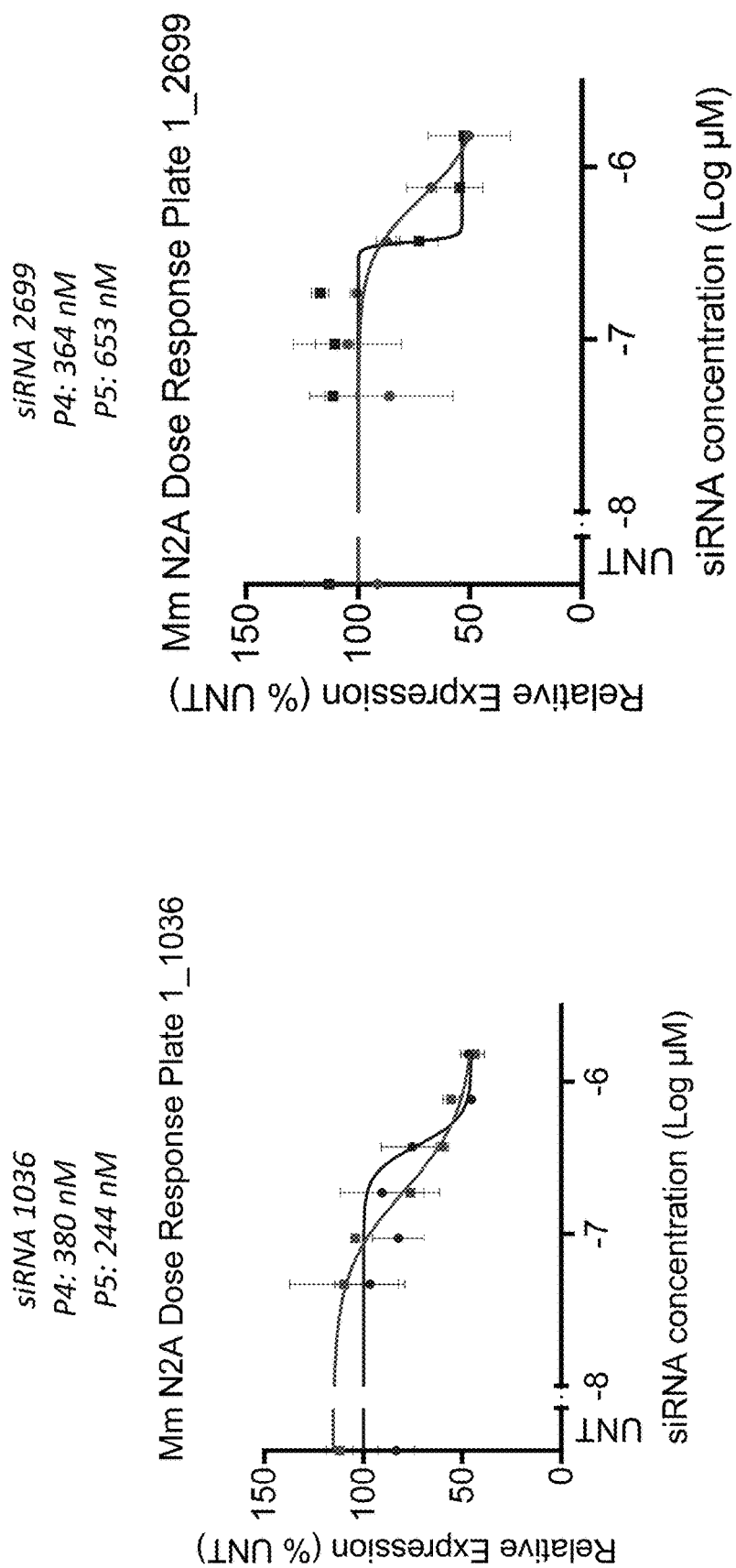
FIG. 9 depicts a comparison of siRNAs 1036 and 2699 in the dose response in mouse cells between siRNAs in a P4 pattern and P5 pattern.

The two siRNA chemical modification patterns were compared to each other. As shown in FIG. 7, there were variations in silencing efficacy for select siRNAs depending on the pattern used. FIG. 8 (A549 human carcinoma cells) and FIG. 9 (N2A mouse cells) provide a comparison between the P4 and P5 pattern for the dose response data.

The target sequences interrogated in the above screen are recited below in Table 9 and Table 10.

TABLE 9

PRNP mRNA Targets Sequences (45-nucleotide)

| PNRP ID | SEQ ID NO | Target Region (45-nucleotide) |
|---|---|---|
| 461 | 63 | GGCUACAUGCUGGGAAGUGCCAUGAGCAGGCCCAUCAUACAUUUC |
| 473 | 64 | GGAAGUGCCAUGAGCAGGCCCAUCAUACAUUUCGGCAGUGACUAU |
| 488 | 65 | AGGCCCAUCAUACAUUUCGGCAGUGACUAUGAGGACCGUUACUAU |
| 494 | 66 | AUCAUACAUUUCGGCAGUGACUAUGAGGACCGUUACUAUCGUGAA |
| 539 | 67 | UGCAUGUACUUUAUAUUUCUAUAUUUGUAACUUUGCAUGUUCUU |
| 540 | 68 | UGUACUUUAUAUUUCUAUAUUUGUAACUUUGCAUGUUCUUGUUU |
| 543 | 69 | GGCCCAUGGAUGAGUACAGCAACCAGAACAACUUUGUGCACGACU |
| 570 | 70 | ACAACCACCAAGGGGGAGAACUUCACCGAGACCGACGUUAAGAUG |
| 594 | 71 | UUCACCGAGACCGACGUUAAGAUGAUGGAGCGCGUGGUUGAGCAG |
| 597 | 72 | UACAGGCCCAUGGAUGAGUACAGCAACCAGAACAACUUUGUGCAC |
| 643 | 73 | CACGGUCACCACAACCACCAAGGGGGAGAACUUCACCGAGACCGA |
| 653 | 74 | AUGUACUUUAUAUUUCUAUAUUUGUAACUUUGCAUGUUCUUGUU |
| 654 | 75 | ACCGAGACCGACGUUAAGAUGAUGGAGCGCGUGGUUGAGCAGAUG |
| 674 | 76 | GCAACCAGAACAACUUUGUGCACGACUGCGUCAAUAUCACAAUCA |
| 675 | 77 | ACCAGAACAACUUUGUGCACGACUGCGUCAAUAUCACAAUCAAGC |
| 732 | 78 | GCGUCAAUAUCACCAUCAAGCAGCACACGGUCACCACCACCACCA |
| 755 | 79 | UAUUACCAGAGAGGAUCGAGCAUGGUCCUCUUCUCCUCUCCACCU |
| 822 | 80 | UCAUCUUCCUGAUAGUGGGAUGAGGAAGGUCUUCCUGUUUUCACC |
| 823 | 81 | GGCUACAUGCUGGGAAGUGCCAUGAGCAGGCCCAUCAUACAUUUC |
| 835 | 82 | GGAAGUGCCAUGAGCAGGCCCAUCAUACAUUUCGGCAGUGACUAU |
| 846 | 83 | GAAGGUCUUCCUGUUUUCACCAUCUUUCUAAUCUUUUUCCAGCUU |
| 915 | 84 | GGCCCAUGGAUGAGUACAGCAACCAGAACAACUUUGUGCACGACU |
| 953 | 85 | GCAACCAGAACAACUUUGUGCACGACUGCGUCAAUAUCACAAUCA |
| 956 | 86 | ACCAGAACAACUUUGUGCACGACUGCGUCAAUAUCACAAUCAAGC |
| 980 | 87 | GCGUCAAUAUCACAAUCAAGCAGCACACGGUCACCACAACCACCA |
| 1005 | 88 | CACGGUCACCACAACCACCAAGGGGGAGAACUUCACCGAGACCGA |
| 1015 | 89 | ACAACCACCAAGGGGGAGAACUUCACCGAGACCGACGUUAAGAUG |
| 1036 | 90 | UUCACCGAGACCGACGUUAAGAUGAUGGAGCGCGUGGUUGAGCAG |
| 1065 | 91 | UAAUGCCAGGCCAGUAAAAGUAUAACAGCAAAUAACCAUUGGUUA |
| 1074 | 92 | GCCAGUAAAAGUAUAACAGCAAAUAACCAUUGGUUAAUCUGGACU |
| 1088 | 93 | AACAGCAAAUAACCAUUGGUUAAUCUGGACUUAUUUUUGGACUUA |
| 1129 | 94 | CUUAGUGCAACAGGUUGAGGCUAAAACAAAUCUCAGAACAGUCUG |
| 1174 | 95 | GCCAGUGCUAACACCGGGCCAAUAAGAAUAUAACACCAAAUAACU |
| 1208 | 96 | GCAGCUAGAGCUCAGUAUACUAAUGCCCUAUCUUAGUAGAGAUUU |
| 1228 | 97 | UAAUGCCCUAUCUUAGUAGAGAUUUCAUAGCUAUUUAGAGAUAUU |
| 1230 | 98 | AUGCCCUAUCUUAGUAGAGAUUUCAUAGCUAUUUAGAGAUAUUUU |
| 1239 | 99 | CUUAGUAGAGAUUUCAUAGCUAUUUAGAGAUAUUUUCCAUUUUAA |
| 1241 | 100 | UAGUAGAGAUUUCAUAGCUAUUUAGAGAUAUUUUCCAUUUUAAGA |

TABLE 9-continued

PRNP mRNA Targets Sequences (45-nucleotide)

| PNRP ID | SEQ ID NO | Target Region (45-nucleotide) |
|---|---|---|
| 1249 | 101 | AUUUCAUAGCUAUUUAGAGAUAUUUUCCAUUUUAAGAAAACCCGA |
| 1447 | 102 | GCUACACAGCAGCUGUUCAACAAGAGUAAAUAUUGUCACAACACU |
| 1482 | 103 | UCACAACACUGAACCUCUGGCUAGAGGACAUAUUCACAGUGAACA |
| 1483 | 104 | CACAACACUGAACCUCUGGCUAGAGGACAUAUUCACAGUGAACAU |
| 1498 | 105 | CUGGCUAGAGGACAUAUUCACAGUGAACAUAACUGUAACAUAUAU |
| 1500 | 106 | GGCUAGAGGACAUAUUCACAGUGAACAUAACUGUAACAUAUAUGA |
| 1520 | 107 | GUGAACAUAACUGUAACAUAUAUGAAAGGCUUCUGGGACUUGAAA |
| 1537 | 108 | AUAUAUGAAAGGCUUCUGGGACUUGAAAUCAAAUGUUUGGGAAUG |
| 1570 | 109 | GCAGCUAGAGCUCAGUAUACUAAUGCCCUAUCUUAGUAGAGAUUU |
| 1575 | 110 | GGGAAUGGUGCCCUUGGAGGCAACCUCCCAUUUUAGAUGUUUAAA |
| 1583 | 111 | UGCCCUUGGAGGCAACCUCCCAUUUUAGAUGUUUAAAGGACCCUA |
| 1638 | 112 | GCUAGAAACUUGAGUUUCUUCAUUUCUGUCUCACAAUUAUCAAAA |
| 1647 | 113 | UAAACUAUAGGUAAUUAAGGCAGCUGAAAAGUAAAUUGCCUUCUA |
| 1652 | 114 | UUUCUUCAUUUCUGUCUCACAAUUAUCAAAAGCUAGAAUUAGCUU |
| 1653 | 115 | AUAGGUAAUUAAGGCAGCUGAAAAGUAAAUUGCCUUCUAGACACU |
| 1683 | 116 | GCUAGAAUUAGCUUCUGCCCUAUGUUUCUGUACUUCUAUUUGAAC |
| 1683 | 117 | UGCCUUCUAGACACUGAAGGCAAAUCUCCUUUGUCCAUUUACCUG |
| 1698 | 118 | GAAGGCAAAUCUCCUUUGUCCAUUUACCUGGAAACCAGAAUGAUU |
| 1727 | 119 | GGAAACCAGAAUGAUUUUGACAUACAGGAGAGCUGCAGUUGUGAA |
| 1757 | 120 | AGCUGCAGUUGUGAAAGCACCAUCAUCAUAGAGGAUGAUGUAAUU |
| 1760 | 121 | UGCAGUUGUGAAAGCACCAUCAUCAUAGAGGAUGAUGUAAUUAAA |
| 1763 | 122 | AGUUGUGAAAGCACCAUCAUCAUAGAGGAUGAUGUAAUUAAAAAA |
| 1765 | 123 | UUGUGAAAGCACCAUCAUCAUAGAGGAUGAUGUAAUUAAAAAAUG |
| 1781 | 124 | AGGCUCCAUUCCAAAGUGGGAAAGAAAUUCUGCUAGCAUUGUUUA |
| 1802 | 125 | AAAAAAUGGUCAGUGUGCAAAGAAAAGAACUGCUUGCAUUUCUUU |
| 1818 | 126 | GCAAAGAAAAGAACUGCUUGCAUUUCUUUAUUUCUGUCUCAUAAU |
| 1819 | 127 | CAAAGAAAAGAACUGCUUGCAUUUCUUUAUUUCUGUCUCAUAAUU |
| 1826 | 128 | AAGAACUGCUUGCAUUUCUUUAUUUCUGUCUCAUAAUUGUCAAAA |
| 1863 | 129 | CCAGCAGACAUAAACUGCGAUAGCUUCAGCUUGCACUGUGGAUUU |
| 1865 | 130 | UCAAAACCAGAAUUAGGUCAAGUUCAUAGUUUCUGUAAUUGGCU |
| 1873 | 131 | CAGAAUUAGGUCAAGUUCAUAGUUUCUGUAAUUGGCUUUUGAAUC |
| 1878 | 132 | UGCGAUAGCUUCAGCUUGCACUGUGGAUUUUCUGUAUAGAAUAUA |
| 1878 | 133 | UUAGGUCAAGUUCAUAGUUUCUGUAAUUGGCUUUUGAAUCAAAGA |
| 1920 | 134 | AUAUAAAACAUAACUUCAAGCUUAUGUCUUCUUUUUAAAACAUCU |
| 1937 | 135 | GGGAAUGGUGCCCUUGGAGGCAACCUCCCAUUUUAGAUGUUUAAA |
| 1938 | 136 | AAAAAUAUCUUAGGUUGGAGAUGACAGAAAUAUGAUUGAUUUGA |
| 1983 | 137 | AGUGGAAAAGAAAUUCUGUUAAUGUUAAUUAAAGUAAAAUUAUU |

TABLE 9-continued

PRNP mRNA Targets Sequences (45-nucleotide)

| PNRP ID | SEQ ID NO | Target Region (45-nucleotide) |
|---|---|---|
| 2010 | 138 | AAUUAAAGUAAAAUUAUUCCCUGAAUUGUUUGAUAUUGUCACCUA |
| 2023 | 139 | UUAUUCCCUGAAUUGUUUGAUAUUGUCACCUAGCAGAUAUGUAUU |
| 2050 | 140 | ACCUAGCAGAUAUGUAUUACUUUUCUGCAAUGUUAUUAUGGCUU |
| 2058 | 141 | GAUAUGUAUUACUUUUCUGCAAUGUUAUUAUGGCUUGCACUUUG |
| 2063 | 142 | GUAUUACUUUUCUGCAAUGUUAUUAUGGCUUGCACUUUGUGAGU |
| 2073 | 143 | CUGGUCUUUGAAUCUGCAUGUACUUCACGUUUUCUAUAUUUGUAA |
| 2079 | 144 | AUGUUAUUAUUGGCUUGCACUUUGUGAGUAUUCUAUGUAAAAUA |
| 2088 | 145 | GCAUGUACUUCACGUUUUCUAUAUUUGUAACUUUGCAUGUAUUUU |
| 2092 | 146 | GUACUUCACGUUUUCUAUAUUUGUAACUUUGCAUGUAUUUUGUUU |
| 2099 | 147 | ACGUUUUCUAUAUUUGUAACUUUGCAUGUAUUUGUUUUGUCAUA |
| 2103 | 148 | UUUCUAUAUUUGUAACUUUGCAUGUAUUUUGUUUUGUCAUAUAAA |
| 2104 | 149 | UUCUAUAUUUGUAACUUUGCAUGUAUUUUGUUUUGUCAUAUAAAA |
| 2129 | 150 | GUAUAUAAAAUAUAUUGCAUAGGACAGACUUAGGAGUUUUGUU |
| 2130 | 151 | UAUAUAAAAUAUAUUGCAUAGGACAGACUUAGGAGUUUUGUUU |
| 2136 | 152 | AAAUAUAUUGCAUAGGACAGACUUAGGAGUUUUGUUUAGAGCA |
| 2159 | 153 | CUUAGGAGUUUGUUUAGAGCAGUUAACAUCUGAAGUGUCUAAUG |
| 2168 | 154 | UUUGUUUAGAGCAGUUAACAUCUGAAGUGUCUAAUGCAUUAACUU |
| 2180 | 155 | GCAAAGAAAAGAACUGCUUGCAUUUCUUUAUUUCUGUCUCAUAAU |
| 2185 | 156 | ACAUCUGAAGUGUCUAAUGCAUUAACUUUUGUAAGGUACUGAAUA |
| 2192 | 157 | AAGUGUCUAAUGCAUUAACUUUUGUAAGGUACUGAAUACUUAAUA |
| 2201 | 158 | AUGCAUUAACUUUUGUAAGGUACUGAAUACUUAAUAUGUGGGAAA |
| 2227 | 159 | UCAAAAACCAGAAUUAGGUCAAGUUCAUAGUUUCUGUAAUUGGCU |
| 2295 | 160 | UAAGAAUCCAAAGUGGACACCAUUAACAGGUCUUUGAAAUAUGCA |
| 2296 | 161 | AAGAAUCCAAAGUGGACACCAUUAACAGGUCUUUGAAAUAUGCAU |
| 2313 | 162 | ACCAUUAACAGGUCUUUGAAAUAUGCAUGUACUUUAUAUUUUCUA |
| 2322 | 163 | AGGUCUUUGAAAUAUGCAUGUACUUUAUAUUUUCUAUAUUUGUAA |
| 2325 | 164 | UCUUUGAAAUAUGCAUGUACUUUAUAUUUUCUAUAUUUGUAACUU |
| 2330 | 165 | GAAAUAUGCAUGUACUUUAUAUUUUCUAUAUUUGUAACUUUGCAU |
| 2344 | 166 | CUUUAUAUUUUCUAUAUUUGUAACUUUGCAUGUUCUUGUUUUGUU |
| 2345 | 167 | AGUGGAAAAGAAAUUCUGUUAAUGUUAAUUAAAGUAAAAUUAUU |
| 2347 | 168 | UAUAUUUUCUAUAUUUGUAACUUUGCAUGUUCUUGUUUUGUUAUA |
| 2348 | 169 | AUAUUUUCUAUAUUUGUAACUUUGCAUGUUCUUGUUUUGUUAUAU |
| 2353 | 170 | UUCUAUAUUUGUAACUUUGCAUGUUCUUGUUUUGUUAUAUAAAAA |
| 2354 | 171 | UCUAUAUUUGUAACUUUGCAUGUUCUUGUUUUGUUAUAUAAAAAA |
| 2384 | 172 | UUGUUAUAUAAAAAAUUGUAAAUGUUUAAUAUCUGACUGAAAUU |
| 2385 | 173 | UGUUAUAUAAAAAAUUGUAAAUGUUUAAUAUCUGACUGAAAUUA |
| 2386 | 174 | GUUAUAUAAAAAAUUGUAAAUGUUUAAUAUCUGACUGAAAUUAA |
| 2387 | 175 | UUAUAUAAAAAAUUGUAAAUGUUUAAUAUCUGACUGAAAUUAAA |

TABLE 9-continued

PRNP mRNA Targets Sequences (45-nucleotide)

| PNRP ID | SEQ ID NO | Target Region (45-nucleotide) |
|---|---|---|
| 2441 | 176 | AUGUUAUUAUUGGCUUGCACUUUGUGAGUAUUCUAUGUAAAAAUA |
| 2491 | 177 | GUAUAUAAAAUAUAUAUUGCAUAGGACAGACUUAGGAGUUUUGUU |
| 2675 | 178 | ACCAUUAACAGGUCUUUGAAAUAUGCAUGUACUUUAUAUUUUCUA |
| 2684 | 179 | AGGUCUUUGAAAUAUGCAUGUACUUUAUAUUUUCUAUAUUUGUAA |
| 2699 | 180 | GCAUGUACUUUAUAUUUUCUAUAUUUGUAACUUUGCAUGUUCUUG |
| 2702 | 181 | UGUACUUUAUAUUUUCUAUAUUUGUAACUUUGCAUGUUCUUGUUU |
| 2703 | 182 | GUACUUUAUAUUUUCUAUAUUUGUAACUUUGCAUGUUCUUGUUUU |
| 2706 | 183 | CUUUAUAUUUUCUAUAUUUGUAACUUUGCAUGUUCUUGUUUUGUU |
| 2709 | 184 | UAUAUUUUCUAUAUUUGUAACUUUGCAUGUUCUUGUUUUGUUAUA |

TABLE 10

PRNP mRNA Targets Sequences (20-nucleotide)

| PRNP ID | SEQ ID NO | Sequence |
|---|---|---|
| 461 | 185 | AGUGCCAUGAGCAGGCCCAU |
| 473 | 186 | AGGCCCAUCAUACAUUUCGG |
| 488 | 187 | UUCGGCAGUGACUAUGAGGA |
| 494 | 188 | AGUGACUAUGAGGACCGUUA |
| 539 | 189 | UUUUCUAUAUUUGUAACUUU |
| 540 | 190 | CUAUAUUUGUAACUUUGCAU |
| 543 | 191 | ACAGCAACCAGAACAACUUU |
| 570 | 192 | GAGAACUUCACCGAGACCGA |
| 594 | 193 | GUUAAGAUGAUGGAGCGCGU |
| 597 | 194 | GAGUACAGCAACCAGAACAA |
| 643 | 195 | CACCAAGGGGAGAACUUCA |
| 653 | 196 | UCUAUAUUUGUAACUUUGCA |
| 654 | 197 | AAGAUGAUGGAGCGCGUGGU |
| 674 | 198 | UUGUGCACGACUGCGUCAAU |
| 675 | 199 | UGCACGACUGCGUCAAUAUC |
| 732 | 200 | UCAAGCAGCACACGGUCACC |
| 755 | 201 | UCGAGCAUGGUCCUCUUCUC |
| 822 | 202 | UGGGAUGAGGAAGGUCUUCC |
| 823 | 203 | AGUGCCAUGAGCAGGCCCAU |
| 835 | 204 | AGGCCCAUCAUACAUUUCGG |
| 846 | 205 | UUCACCAUCUUUCUAAUCUU |
| 935 | 206 | ACAGCAACCAGAACAACUUU |
| 953 | 207 | UUGUGCACGACUGCGUCAAU |

TABLE 10-continued

PRNP mRNA Targets Sequences (20-nucleotide)

| PRNP ID | SEQ ID NO | Sequence |
|---|---|---|
| 956 | 208 | UGCACGACUGCGUCAAUAUC |
| 980 | 209 | UCAAGCAGCACACGGUCACC |
| 1005 | 210 | CACCAAGGGGAGAACUUCA |
| 1015 | 211 | GAGAACUUCACCGAGACCGA |
| 1036 | 212 | GUUAAGAUGAUGGAGCGCGU |
| 1065 | 213 | AAAAGUAUAACAGCAAAUAA |
| 1074 | 214 | ACAGCAAAUAACCAUUGGUU |
| 1088 | 215 | UUGGUUAAUCUGGACUUAUU |
| 1129 | 216 | UGAGGCUAAAACAAAUCUCA |
| 1174 | 217 | GGGCCAAUAAGAAUAUAACA |
| 1208 | 218 | UAUACUAAUGCCCUAUCUUA |
| 1228 | 219 | GUAGAGAUUUCAUAGCUAUU |
| 1230 | 220 | AGAGAUUUCAUAGCUAUUUA |
| 1239 | 221 | AUAGCUAUUUAGAGAUAUUU |
| 1241 | 222 | AGCUAUUUAGAGAUAUUUUC |
| 1249 | 223 | AGAGAUAUUUUCCAUUUUAA |
| 1447 | 224 | UUCAACAAGAGUAAAUAUUG |
| 1482 | 225 | UCUGGCUAGAGGACAUAUUC |
| 1483 | 226 | CUGGCUAGAGGACAUAUUCA |
| 1498 | 227 | AUUCACAGUGAACAUAACUG |
| 1500 | 228 | UCACAGUGAACAUAACUGUA |
| 1520 | 229 | ACAUAUGAAAGGCUUCUG |
| 1537 | 230 | CUGGGACUUGAAAUCAAAUG |

TABLE 10-continued

PRNP mRNA Targets Sequences (20-nucleotide)

| PRNP ID | SEQ ID NO | Sequence |
|---|---|---|
| 1570 | 231 | UAUACUAAUGCCCUAUCUUA |
| 1575 | 232 | GGAGGCAACCUCCCAUUUUA |
| 1583 | 233 | CCUCCCAUUUUAGAUGUUUA |
| 1638 | 234 | UUCUUCAUUUCUGUCUCACA |
| 1647 | 235 | UAAGGCAGCUGAAAAGUAAA |
| 1652 | 236 | CUCACAAUUAUCAAAGCUA |
| 1653 | 237 | AGCUGAAAAGUAAAUUGCCU |
| 1683 | 238 | UGCCCUAUGUUUCUGUACUU |
| 1683 | 239 | GAAGGCAAAUCUCCUUUGUC |
| 1698 | 240 | UUGUCCAUUUACCUGGAAAC |
| 1727 | 241 | UUUGACAUACAGGAGAGCUG |
| 1757 | 242 | AGCACCAUCAUCAUAGAGGA |
| 1760 | 243 | ACCAUCAUCAUAGAGGAUGA |
| 1763 | 244 | AUCAUCAUAGAGGAUGAUGU |
| 1765 | 245 | CAUCAUAGAGGAUGAUGUAA |
| 1781 | 246 | GUGGGAAAGAAAUUCUGCUA |
| 1802 | 247 | UGCAAAGAAAAGAACUGCUU |
| 1818 | 248 | GCUUGCAUUUCUUUAUUUCU |
| 1819 | 249 | CUUGCAUUUCUUUAUUUCUG |
| 1826 | 250 | UUCUUUAUUUCUGUCUCAUA |
| 1863 | 251 | UGCGAUAGCUUCAGCUUGCA |
| 1865 | 252 | AGGUCAAGUUCAUAGUUUCU |
| 1873 | 253 | UUCAUAGUUUCUGUAAUUGG |
| 1878 | 254 | UUGCACUGUGGAUUUUCUGU |
| 1878 | 255 | AGUUUCUGUAAUUGGCUUUU |
| 1920 | 256 | UCAAGCUUAUGUCUUCUUUU |
| 1937 | 257 | GGAGGCAACCUCCCAUUUUA |
| 1938 | 258 | UUGGAGAUGACAGAAAUAUG |
| 1983 | 259 | UCUGUUAAUGUUAAUUAAAG |
| 2010 | 260 | AUUCCCUGAAUUGUUUGAUA |
| 2023 | 261 | UUUGAUAUUGUCACCUAGCA |
| 2050 | 262 | AUUACUUUUCUGCAAUGUUA |
| 2058 | 263 | UCUGCAAUGUUAUUAUUGGC |
| 2063 | 264 | AAUGUUAUUAUUGGCUUGCA |
| 2073 | 265 | GCAUGUACUUCACGUUUUCU |
| 2079 | 266 | UGCACUUUGUGAGUAUUCUA |
| 2088 | 267 | UUUCUAUAUUUGUAACUUUG |
| 2092 | 268 | UAUAUUUGUAACUUUGCAUG |
| 2099 | 269 | GUAACUUUGCAUGUAUUUUG |
| 2103 | 270 | CUUUGCAUGUAUUUUGUUUU |
| 2104 | 271 | UUUGCAUGUAUUUUGUUUUG |
| 2129 | 272 | AUUGCAUAGGACAGACUUAG |
| 2130 | 273 | UUGCAUAGGACAGACUUAGG |
| 2136 | 274 | AGGACAGACUUAGGAGUUUU |
| 2159 | 275 | UAGAGCAGUUAACAUCUGAA |
| 2168 | 276 | UAACAUCUGAAGUGUCUAAU |
| 2180 | 277 | GCUUGCAUUUCUUUAUUUCU |
| 2185 | 278 | AAUGCAUUAACUUUUGUAAG |
| 2192 | 279 | UAACUUUUGUAAGGUACUGA |
| 2201 | 280 | UAAGGUACUGAAUACUUAAU |
| 2227 | 281 | AGGUCAAGUUCAUAGUUUCU |
| 2295 | 282 | GACACCAUUAACAGGUCUUU |
| 2296 | 283 | ACACCAUUAACAGGUCUUUG |
| 2313 | 284 | UUGAAAUAUGCAUGUACUUU |
| 2322 | 285 | GCAUGUACUUUAUAUUUUCU |
| 2325 | 286 | UGUACUUUAUAUUUUCUAUA |
| 2330 | 287 | UUUAUAUUUCUAUAUUUGU |
| 2344 | 288 | AUUUGUAACUUUGCAUGUUC |
| 2345 | 289 | UCUGUUAAUGUUAAUUAAAG |
| 2347 | 290 | UGUAACUUUGCAUGUUCUUG |
| 2348 | 291 | GUAACUUUGCAUGUUCUUGU |
| 2353 | 292 | UUUGCAUGUUCUUGUUUUGU |
| 2354 | 293 | UUGCAUGUUCUUGUUUUGUU |
| 2384 | 294 | AUUGUAAAUGUUUAAUAUCU |
| 2385 | 295 | UUGUAAAUGUUUAAUAUCUG |
| 2386 | 296 | UGUAAAUGUUUAAUAUCUGA |
| 2387 | 297 | GUAAAUGUUUAAUAUCUGAC |
| 2441 | 298 | UGCACUUUGUGAGUAUUCUA |
| 2491 | 299 | AUUGCAUAGGACAGACUUAG |
| 2675 | 300 | UUGAAAUAUGCAUGUACUUU |
| 2684 | 301 | GCAUGUACUUUAUAUUUUCU |
| 2699 | 302 | UUUCUAUAUUUGUAACUUUG |
| 2702 | 303 | CUAUAUUUGUAACUUUGCAU |
| 2703 | 304 | UAUAUUUGUAACUUUGCAUG |

TABLE 10-continued

PRNP mRNA Targets Sequences (20-nucleotide)

| PRNP ID | SEQ ID NO | Sequence |
|---|---|---|
| 2706 | 305 | AUUUGUAACUUUGCAUGUUC |
| 2709 | 306 | UGUAACUUUGCAUGUUCUUG |

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;
Ausubel et al. (eds.), CURRENT PROTOCOLS IN MOLECULAR BIOLOGY, John Wiley &Sons, N Y (1993);
Ausubel, F. M. et al. eds., SHORT PROTOCOLS IN MOLECULAR BIOLOGY (4th Ed. 1999) John Wiley & Sons, NY. (ISBN 0-471-32938-X);
CONTROLLED DRUG BIOAVAILABILITY, DRUG PRODUCT DESIGN AND PERFORMANCE, Smolen and Ball (eds.), Wiley, New York (1984);
Giege, R. and Ducruix, A. Barrett, CRYSTALLIZATION OF NUCLEIC ACIDS AND PROTEINS, a Practical Approach, 2nd ea., pp. 201-16, Oxford University Press, New York, New York, (1999);
Goodson, in MEDICAL APPLICATIONS OF CONTROLLED RELEASE, vol. 2, pp. 115-138 (1984);
Hammerling, et al., in: MONOCLONAL ANTIBODIES AND T-CELL HYBRIDOMAS 563-681 (Elsevier, N.Y., 1981;
Harlow et al., ANTIBODIES: A LABORATORY MANUAL, (Cold Spring Harbor Laboratory Press, 2nd ed. 1988);
Kabat et al., SEQUENCES OF PROTEINS OF IMMUNOLOGICAL INTEREST (National Institutes of Health, Bethesda, Md. (1987) and (1991);
Kabat, E. A., et al. (1991) SEQUENCES OF PROTEINS OF IMMUNOLOGICAL INTEREST, Fifth Edition, U.S. Department of Health and Human Services, NIH Publication No. 91-3242;
Kontermann and Dubel eds., ANTIBODY ENGINEERING (2001) Springer-Verlag. New York. 790 pp. (ISBN 3-540-41354-5).
Kriegler, Gene Transfer and Expression, A Laboratory Manual, Stockton Press, N Y (1990);
Lu and Weiner eds., CLONING AND EXPRESSION VECTORS FOR GENE FUNCTION ANALYSIS (2001) BioTechniques Press. Westborough, MA 298 pp. (ISBN 1-881299-21-X).
MEDICAL APPLICATIONS OF CONTROLLED RELEASE, Langer and Wise (eds.), CRC Pres., Boca Raton, Fla. (1974);
Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V. 2:409 pp. (ISBN 0-632-01318-4).
Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).
SUSTAINED AND CONTROLLED RELEASE DRUG DELIVERY SYSTEMS, J. R. Robinson, ed., Marcel Dekker, Inc., New York, 1978
Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. An RNA molecule comprising:

about 8 nucleotides to 80 nucleotides in length; and a double stranded RNA (dsRNA) comprising a sense strand and an antisense strand, each strand with a 5' end and a 3' end, wherein a portion of the antisense strand is complementary to a portion of the sense strand, wherein the antisense strand comprises a sequence substantially complementary to a prion protein (PRNP) nucleic acid sequence of any one of SEQ ID Nos: 90, 159, 176, 179, and 181-183 to direct target-specific silencing, and wherein the antisense strand comprises at least 70% 2'-O-methyl modifications.

2. The RNA molecule of claim 1, wherein the dsRNA comprises complementarity to at least 10, 11, 12, or 13 contiguous nucleotides of the PRNP nucleic acid sequence of any one of SEQ ID Nos: 90, 159, 176, 179, and 181-183.

3. The RNA molecule of claim 1, wherein the dsRNA comprises at least 80% chemically modified nucleotides.

4. The RNA molecule of claim 1, wherein:

A:

(1) the nucleotide at position 14 from the 5' end of the antisense strand is not a 2'-methoxy-ribonucleotide;

(2) the nucleotides at positions 1-2 to 1-7 from the 3' end of the antisense strand are connected to each other via phosphorothioate internucleotide linkages;

(3) the sense strand comprises at least 70% 2'-O-methyl modifications; and (4) the nucleotides at positions 1-2 from the 5' end of the sense strand are connected to each other via phosphorothioate internucleotide linkages; or

B:

(1) the antisense strand comprises at least 85% 2'-O-methyl modifications;

(2) the nucleotides at positions 2 and 14 from the 5' end of the antisense strand are not 2'-methoxy-ribonucleotides;

(3) the nucleotides at positions 1-2 to 1-7 from the 3' end of the antisense strand are connected to each other via phosphorothioate internucleotide linkages;
(4) the sense strand comprises 100% 2'-O-methyl modifications; and
(5) the nucleotides at positions 1-2 from the 5' end of the sense strand are connected to each other via phosphorothioate internucleotide linkages; or C:
(1) the antisense strand comprises at least 75% 2'-O-methyl modifications;
(2) the nucleotides at positions 4, 5, 6, and 14 from the 5' end of the antisense strand are not 2'-methoxy-ribonucleotides;
(3) the nucleotides at positions 1-2 to 1-7 from the 3' end of the antisense strand are connected to each other via phosphorothioate internucleotide linkages;
(4) the sense strand comprises 100% 2'-O-methyl modifications; and
(5) the nucleotides at positions 1-2 from the 5' end of the sense strand are connected to each other via phosphorothioate internucleotide linkages; or D:
(1) the antisense strand comprises at least 75% 2'-O-methyl modifications;
(2) the nucleotides at positions 2, 4, 5, 6, and 14 from the 5' end of the antisense strand are not 2'-methoxy-ribonucleotides;
(3) the nucleotides at positions 1-2 to 1-7 from the 3' end of the antisense strand are connected to each other via phosphorothioate internucleotide linkages;
(4) the sense strand comprises 100% 2'-O-methyl modifications; and
(5) the nucleotides at positions 1-2 from the 5' end of the sense strand are connected to each other via phosphorothioate internucleotide linkages; or E:
(1) the antisense strand comprises at least 75% 2'-O-methyl modifications;
(2) the nucleotides at positions 2, 6, 14, and 16 from the 5' end of the antisense strand are not 2'-methoxy-ribonucleotides;
(3) the nucleotides at positions 1-2 to 1-7 from the 3' end of the antisense strand are connected to each other via phosphorothioate internucleotide linkages;
(4) the sense strand comprises at least 65% 2'-O-methyl modifications;
(5) the nucleotides at positions 7, 9, 10, and 11 from the 3' end of the sense strand are not 2'-methoxy-ribonucleotides; and
(6) the nucleotides at positions 1-2 from the 5' end of the sense strand are connected to each other via phosphorothioate internucleotide linkages; or F:
(1) the antisense strand comprises at least 75% 2'-O-methyl modifications;
(2) the nucleotides at positions 2 and 14 from the 5' end of the antisense strand are not 2'-methoxy-ribonucleotides;
(3) the nucleotides at positions 1-2 to 1-7 from the 3' end of the antisense strand are connected to each other via phosphorothioate internucleotide linkages;
(4) the sense strand comprises at least 75% 2'-O-methyl modifications;
(5) the nucleotides at positions 7, 10, and 11 from the 3' end of the sense strand are not 2'-methoxy-ribonucleotides; and
(6) the nucleotides at positions 1-2 from the 5' end of the sense strand are connected to each other via phosphorothioate internucleotide linkages.

5. The RNA molecule of claim 1, wherein a functional moiety is linked to the 5' end and/or the 3' end of the antisense strand.

6. The RNA molecule of claim 5, wherein the functional moiety is linked to the antisense strand and/or the sense strand by a linker.

7. A pharmaceutical composition for inhibiting the expression of a prion protein (PRNP) gene in an organism, comprising the RNA molecule of claim 1 and a pharmaceutically acceptable carrier.

8. A branched RNA compound comprising two or more RNA molecules comprising 15 to 35 nucleotides in length,
wherein each RNA molecule comprises a double stranded (ds) RNA comprising a sense strand and an antisense strand,
wherein each antisense strand independently comprises a sequence substantially complementary to a prion protein (PRNP) nucleic acid sequence of any one of SEQ ID NOs: 90, 159, 176, 179, and 181-183 to direct target-specific silencing,
wherein the antisense strand comprises at least 70% 2'-O-methyl modifications, and
wherein the two or more RNA molecules are connected to one another by one or more moieties independently selected from a linker, a spacer, and a branching point.

9. A compound of formula (I):

$$L\text{-}(N)_n \qquad (I),$$

wherein:
L comprises an ethylene glycol chain, an alkyl chain, a peptide, an RNA, a DNA, a phosphate, a phosphonate, a phosphoramidate, an ester, an amide, a triazole, or combinations thereof, wherein formula (I) optionally further comprises one or more branch point B, and one or more spacer S, wherein:
the one or more branched point B is independently for each occurrence a polyvalent organic species or derivative thereof;
the one or more spacer S comprises independently for each occurrence an ethylene glycol chain, an alkyl chain, a peptide, RNA, DNA, a phosphate, a phosphonate, a phosphoramidate, an ester, an amide, a triazole, or combinations thereof; and
N is a double stranded RNA comprising 15 to 35 bases in length comprising a sense strand and an antisense strand; wherein:
the antisense strand comprises at least 70% 2'-O-methyl modifications;
the antisense strand comprises a sequence substantially complementary to a PRNP nucleic acid sequence of any one of SEQ ID NOs: 90, 159, 176, 179, and 181-183 to direct target-specific silencing; and
the sense strand and antisense strand each independently comprise one or more chemical modifications; and
n is 2, 3, 4, 5, 6, 7, or 8.

10. The compound of claim 9, wherein:
the compound has a structure selected from formulas (I-1)-(I-9):

$$N\text{—}L\text{—}N \qquad (I\text{-}1)$$

219
-continued (I-2) N—S—L—S—N (I-3)

(I-4) N—L—B—L—N
      with N above B via L, N below (I-5) [structure I-5 with two B centers linked by L, each with S-N substituents]

(I-6) [structure I-6]

(I-7) [structure I-7]

(I-8) [structure I-8]

(I-9) [structure I-9]

220

11. The compound of claim 9, wherein:
L is structure L1:

(L1) [structure showing phosphate-glycerol-triethylene glycol methyl ether and amino-phosphate linker]

or

L is structure L2:

(L2) [structure showing phosphate-glycerol-triethylene glycol methyl ether and phosphate linker]

12. A pharmaceutical composition for inhibiting the expression of a PRNP gene in an organism, comprising the branched RNA compound of claim 8, and a pharmaceutically acceptable carrier.

13. The RNA molecule of claim 1, wherein the RNA molecule comprises about 15 nucleotides to 25 nucleotides in length.

14. The RNA molecule of claim 1, wherein the dsRNA comprises no more than 3 mismatches with the PRNP nucleic acid sequence of any one of SEQ ID NOs: 90, 159, 176, 179, and 181-183.

15. The RNA molecule of claim 1, wherein:
the antisense strand comprises no more than 3 mismatches with the PRNP nucleic acid sequence of any one of SEQ ID NOs: 90, 159, 176, 179, and 181-183;
the antisense strand comprises full complementarity to the PRNP nucleic acid sequence of any one of SEQ ID NOs: 90, 159, 176, 179, 181-183;
the antisense strand comprises about 15 nucleotides to 25 nucleotides in length, optionally 20, 21, or 22 nucleotides in length;
the sense strand comprises about 15 nucleotides to 25 nucleotides in length, optionally 15, 16, 18, or 20 nucleotides in length;
the dsRNA comprises a double-stranded region of 15 base pairs to 20 base pairs, optionally 15, 16, 18, or 20 base pairs;
the dsRNA comprises a blunt-end;
the dsRNA comprises at least one single stranded nucleotide overhang, optionally about a 2-nucleotide to 5-nucleotide single stranded nucleotide overhang;
the sense strand comprises at least one of a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a mixture thereof;

the dsRNA comprises at least one modified internucleotide linkage, optionally wherein the at least one modified internucleotide linkage comprises a phosphorothioate internucleotide linkage;

the dsRNA comprises 4-16 phosphorothioate internucleotide linkages or 8-13 phosphorothioate internucleotide linkages;

the nucleotides at positions 1 and 2 from the 3' end of the sense strand, and the nucleotides at positions 1 and 2 from the 5' end of the antisense strand are connected to adjacent ribonucleotides via phosphorothioate linkages; and/or the dsRNA comprises at least one modified internucleotide linkage of Formula I:

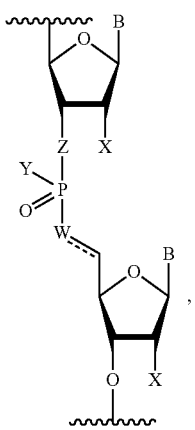
(I)

wherein:
B is a base pairing moiety;
W is selected from the group consisting of O, $OCH_2$, OCH, $CH_2$, and CH;
X is selected from the group consisting of halo, hydroxy, and $C_{1-6}$ alkoxy;
Y is selected from the group consisting of $O^-$, OH, OR, $NH^-$, $NH_2$, $S^-$, and SH;
Z is selected from the group consisting of O and $CH_2$;
R is a protecting group; and
═ is an optional double bond.

16. The RNA molecule of claim 1, wherein the dsRNA is fully chemically modified.

17. The RNA molecule of claim 1, wherein the dsRNA comprises at least 70% 2'-O-methyl nucleotide modifications.

18. The RNA molecule of claim 1, wherein the antisense strand comprises 70% to 90% 2'-O-methyl nucleotide modifications.

19. The RNA molecule of claim 1, wherein the sense strand comprises at least 65% 2'-O-methyl nucleotide modifications or 100% 2'-O-methyl nucleotide modifications.

20. The RNA molecule of claim 1, wherein the sense strand comprises one or more nucleotide mismatches between the antisense strand and the sense strand.

21. The RNA molecule of claim 20, wherein the one or more nucleotide mismatches are present at positions 2, 6, and 12 from the 5' end of the sense strand.

22. The RNA molecule of claim 1, wherein the antisense strand comprises a 5' phosphate, a 5'-alkyl phosphonate, a 5' alkylene phosphonate, or a 5' alkenyl phosphonate.

23. The RNA molecule of claim 22, wherein the antisense strand comprises a 5' vinyl phosphonate.

24. The RNA molecule of claim 5, wherein the functional moiety comprises a hydrophobic moiety.

25. The RNA molecule of claim 24, wherein the hydrophobic moiety is selected from the group consisting of fatty acids, steroids, secosteroids, lipids, gangliosides, nucleoside analogs, endocannabinoids, vitamins, and a mixture thereof.

26. The RNA molecule of claim 25, wherein the steroid selected from the group consisting of cholesterol and lithocholic acid (LCA).

27. The RNA molecule of claim 25, wherein the fatty acid selected from the group consisting of eicosapentaenoic acid (EPA), docosahexaenoic acid (DHA) and docosanoic acid (DCA).

28. The RNA molecule of claim 25, wherein the vitamin is selected from the group consisting of choline, vitamin A, vitamin E, retinoic acid, alpha-tocopheryl succinate, and derivatives or metabolites thereof.

29. The RNA molecule of claim 6, wherein the linker comprises a divalent linker or a trivalent linker.

30. The RNA molecule of claim 29, wherein the divalent linker or the trivalent linker is selected from the group consisting of:

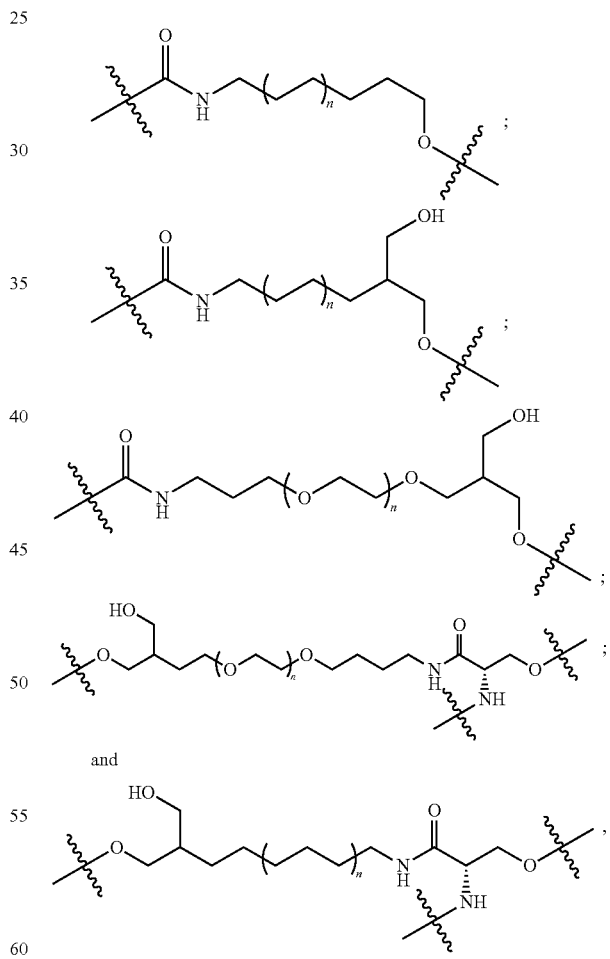

wherein n is 1, 2, 3, 4, or 5.

31. The RNA molecule of claim 6, wherein the linker comprises an ethylene glycol chain, an alkyl chain, a peptide, an RNA, a DNA, a phosphodiester, a phosphorothioate, a phosphoramidate, an amide, a carbamate, or a combination thereof.

32. The RNA molecule of claim 6, wherein when the linker is a trivalent linker, the linker further links a phosphodiester or a phosphodiester derivative.

33. The RNA molecule of claim 32, wherein the phosphodiester or the phosphodiester derivative is selected from the group consisting of:

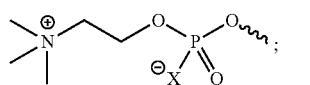  (Zc1)

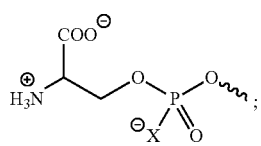  (Zc2)

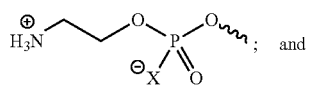  (Zc3) and

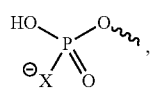  (Zc4)

wherein X is O, S, or $BH_3$.

34. The pharmaceutical composition of claim 7, wherein the RNA molecule inhibits the expression of the PRNP gene by at least 50% or by at least 80%.

35. The branched RNA compound of claim 8, wherein each RNA molecule comprises 15 to 25 nucleotides in length.

36. The compound of claim 9, wherein the antisense strand comprises a 5' terminal group R selected from the group consisting of:

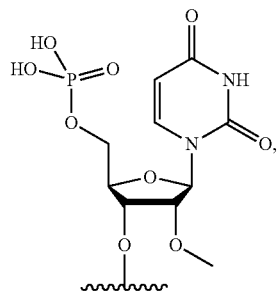  $R^1$

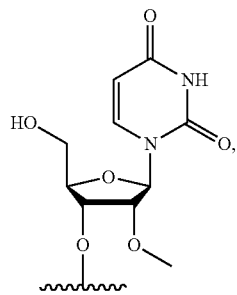  $R^2$

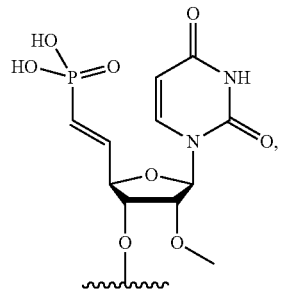  $R^3$

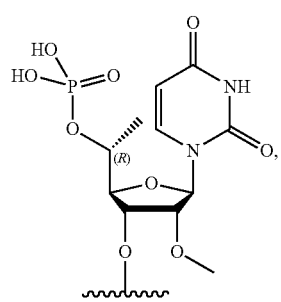  $R^4$

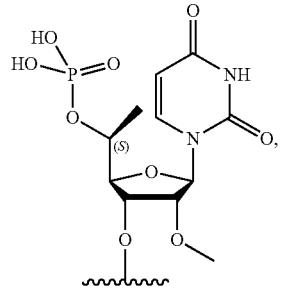  $R^5$

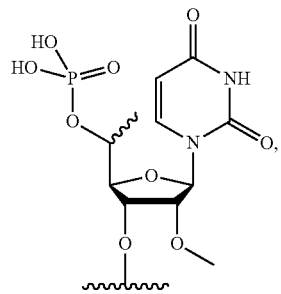  $R^6$

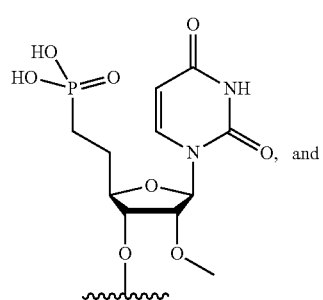  $R^7$

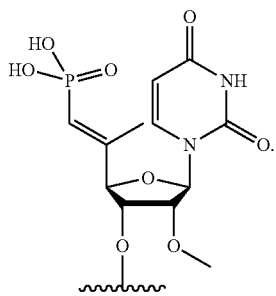

37. The compound of claim 9, wherein the compound has the structure of formula (II):

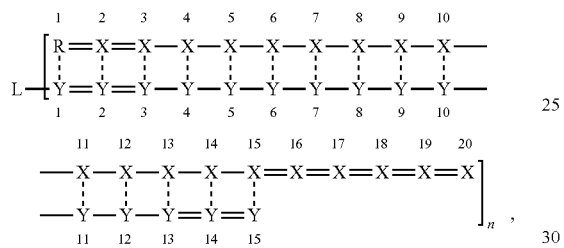

wherein:

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester internucleoside linkage;

= represents a phosphorothioate internucleoside linkage; and

--- represents, individually for each occurrence, a base-pairing interaction or a mismatch.

38. The compound of claim 9, wherein the compound has the structure of formula (IV):

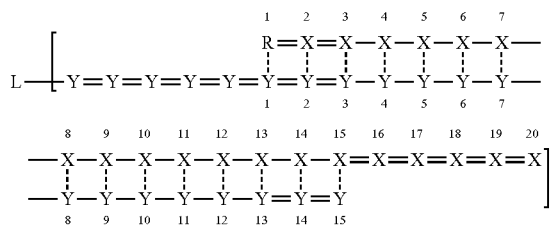

wherein:

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester internucleoside linkage;

= represents a phosphorothioate internucleoside linkage; and

--- represents, individually for each occurrence, a base-pairing interaction or a mismatch.

39. The compound of claim 36, wherein R is $R^3$ and n is 2.

40. The compound of claim 36, wherein L is structure L2:

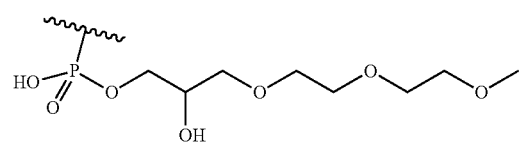

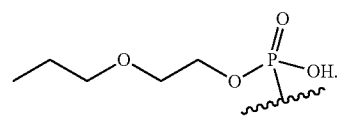

41. The compound of claim 40, wherein R is $R^3$ and n is 2.

42. The pharmaceutical composition of claim 12, wherein the branched RNA compound inhibits the expression of the PRNP gene by at least 50% or at least 80%.

43. The RNA molecule of claim 1, wherein the antisense strand comprises no more than 3 mismatches with the PRNP nucleic acid sequence of any one of SEQ ID NOs: 90, 159, 176, 179, and 181-183.

44. The RNA molecule of claim 1, wherein the antisense strand comprises full complementarity to the PRNP nucleic acid sequence of any one of SEQ ID NOs: 90, 159, 176, 179, and 181-183.

45. The RNA molecule of claim 1, wherein the antisense strand comprises about 15 nucleotides to 25 nucleotides in length, optionally 20, 21, or 22 nucleotides in length.

46. The RNA molecule of claim 1, wherein the sense strand comprises about 15 nucleotides to 25 nucleotides in length, optionally 15, 16, 18, or 20 nucleotides in length.

47. The RNA molecule of claim 1, wherein the dsRNA comprises a double-stranded region of 15 base pairs to 20 base pairs, optionally 15, 16, 18, or 20 base pairs.

48. The RNA molecule of claim 1, wherein the dsRNA comprises a blunt-end.

49. The RNA molecule of claim 1, wherein the dsRNA comprises at least one single stranded nucleotide overhang, optionally about a 2-nucleotide to 5-nucleotide single stranded nucleotide overhang.

50. The RNA molecule of claim 1, wherein:

the sense strand comprises at least one modified nucleotide, wherein the sense strand comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a mixture thereof;

the dsRNA comprises at least one modified internucleotide linkage, optionally wherein the at least one modified internucleotide linkage comprises a phosphorothioate internucleotide linkage;

the dsRNA comprises 4-16 phosphorothioate internucleotide linkages or 8-13 phosphorothioate internucleotide linkages;

the nucleotides at positions 1 and 2 from the 3' end of sense strand, and the nucleotides at positions 1 and 2 from the 5' end of antisense strand are connected to adjacent ribonucleotides via phosphorothioate linkages; and/or the dsRNA comprises at least one modified internucleotide linkage of Formula I:

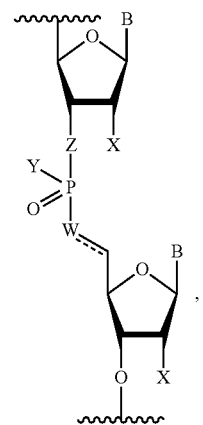

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and

=== is an optional double bond.

\* \* \* \* \*

UNITED STATES PATENT AND TRADEMARK OFFICE
CERTIFICATE OF CORRECTION

PATENT NO. : 12,258,566 B2
APPLICATION NO. : 17/187129
DATED : March 25, 2025
INVENTOR(S) : Khvorova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Third Day of February, 2026

John A. Squires
*Director of the United States Patent and Trademark Office*

SEQUENCE LISTING

```
<160> NUMBER OF SEQ ID NOS: 306

<210> SEQ ID NO 1
<211> LENGTH: 45
<212> TYPE: RNA
<213> ORGANISM: Homo sapiens

<400> SEQUENCE: 1
ggaagugcca ugagcaggcc caucauacau uucggcagug acuau         45

<210> SEQ ID NO 2
<211> LENGTH: 45
<212> TYPE: RNA
<213> ORGANISM: Homo sapiens

<400> SEQUENCE: 2
ucaaaaacca gaauuagguc aaguucauag uuucuguaau uggcu         45

<210> SEQ ID NO 3
```

```
<211> LENGTH: 45
<212> TYPE: RNA
<213> ORGANISM: Homo sapiens

<400> SEQUENCE: 3
auguuauuau uggcuugcac uuugugagua uucuauguaa aaaua          45

<210> SEQ ID NO 4
<211> LENGTH: 45
<212> TYPE: RNA
<213> ORGANISM: Homo sapiens

<400> SEQUENCE: 4
aggucuuuga aauaugcaug uacuuuauau uuucuauauu uguaa          45

<210> SEQ ID NO 5
<211> LENGTH: 45
<212> TYPE: RNA
<213> ORGANISM: Homo sapiens

<400> SEQUENCE: 5
cuuuauauuu ucuauauuug uaacuuugca uguucuuguu uuguu          45

<210> SEQ ID NO 6
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 6
ggcuacaugc ugggaagugc caugagcagg cccaucauac auuc           45

<210> SEQ ID NO 7
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 7
accagaacaa cuuugugcac gacugcguca auaucacaau caagc          45

<210> SEQ ID NO 8
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 8
cacggucacc acaaccacca agggggagaa cuucaccgag accga          45

<210> SEQ ID NO 9
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 9
uucaccgaga ccgacguuaa gaugauggag cgcgugguug agcag          45
```

<210> SEQ ID NO 10
<211> LENGTH: 45
<212> TYPE: RNA
<213> ORGANISM: Unknown
<220> FEATURE:
<223> OTHER INFORMATION: Description of Unknown:
    PRNP target sequence

<400> SEQUENCE: 10
gcuagaauua gcuucugccc uauguuucug uacuucuauu ugaac                45

<210> SEQ ID NO 11
<211> LENGTH: 45
<212> TYPE: RNA
<213> ORGANISM: Unknown
<220> FEATURE:
<223> OTHER INFORMATION: Description of Unknown:
    PRNP target sequence

<400> SEQUENCE: 11
ccagcagaca uaaacugcga uagcuucagc uugcacugug gauuu                45

<210> SEQ ID NO 12
<211> LENGTH: 45
<212> TYPE: RNA
<213> ORGANISM: Unknown
<220> FEATURE:
<223> OTHER INFORMATION: Description of Unknown:
    PRNP target sequence

<400> SEQUENCE: 12
auauaaaaca uaacuucaag cuuaugucuu cuuuuaaaa caucu                 45

<210> SEQ ID NO 13
<211> LENGTH: 20
<212> TYPE: RNA
<213> ORGANISM: Homo sapiens

<400> SEQUENCE: 13
aggcccauca uacauuucgg                                            20

<210> SEQ ID NO 14
<211> LENGTH: 20
<212> TYPE: RNA
<213> ORGANISM: Homo sapiens

<400> SEQUENCE: 14
aggucaaguu cauaguuucu                                            20

<210> SEQ ID NO 15
<211> LENGTH: 20
<212> TYPE: RNA
<213> ORGANISM: Homo sapiens

<400> SEQUENCE: 15
ugcacuuugu gaguauucua                                            20

<210> SEQ ID NO 16
<211> LENGTH: 20
<212> TYPE: RNA
<213> ORGANISM: Homo sapiens

<400> SEQUENCE: 16
gcauguacuu uauauuuucu                                            20

```
<210> SEQ ID NO 17
<211> LENGTH: 20
<212> TYPE: RNA
<213> ORGANISM: Homo sapiens

<400> SEQUENCE: 17
auuuguaacu uugcauguuc                                              20

<210> SEQ ID NO 18
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccaucauaca uuucga                                                  16

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
caaguucaua guuuca                                                  16

<210> SEQ ID NO 20
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cuuugugagu auucua                                                  16

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
guacuuuaua uuuuca                                                  16

<210> SEQ ID NO 22
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
guaacuuugc auguua                                                  16

<210> SEQ ID NO 23
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccaugagcag gcccaa                                                        16

<210> SEQ ID NO 24
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cgacugcguc aauaua                                                        16

<210> SEQ ID NO 25
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25 aaggggaga acuuca                                                         16

<210> SEQ ID NO 26
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
agaugaugga gcgcga                                                        16

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cuauguuucu guacua                                                        16

<210> SEQ ID NO 28
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
auagcuucag cuugca                                                        16

<210> SEQ ID NO 29
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 29
gcuuaugucu ucuuua                                                    16

<210> SEQ ID NO 30
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ccaucauaca uuucgg                                                    16

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
caaguucaua guuucu                                                    16

<210> SEQ ID NO 32
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
guacuuuaua uuuucu                                                    16

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
guaacuuugc auguuc                                                    16

<210> SEQ ID NO 34
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaugagcag gcccau                                                    16

<210> SEQ ID NO 35
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 35
cgacugcguc aauauc                                                          16

<210> SEQ ID NO 36
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
agaugaugga gcgcgu                                                          16

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cuauguuucu guacuu                                                          16

<210> SEQ ID NO 38
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcuuaugucu ucuuuu                                                          16

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucgaaaugua ugaugggccu c                                                    21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ugaaacuaug aacuugaccu u                                                    21

<210> SEQ ID NO 41
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 41
uagaauacuc acaaagugca u                                             21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ugaaaauaua aaguacaugc u                                             21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uaacaugcaa aguuacaaau u                                             21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uugggccugc ucauggcacu a                                             21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uauauugacg cagucgugca g                                             21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ugaaguucuc ccccuuggug c                                             21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 47
ucgcgcucca ucaucuuaac c                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uaguacagaa acauagggca c                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugcaagcuga agcuaucgca c                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uaaagaagac auaagcuuga u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ccgaaaugua ugaugggccu g                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
agaaacuaug aacuugaccu a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uagaauacuc acaaagugca a    21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
agaaaauaua aaguacaugc a    21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gaacaugcaa aguuacaaau a    21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
augggccugc ucauggcacu u    21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gauauugacg cagucgugca c    21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ugaaguucuc ccccuuggug g    21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 59
acgcgcucca ucaucuuaac g                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aaguacagaa acauagggca g                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ugcaagcuga agcuaucgca g                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aaaagaagac auaagcuuga a                                              21

<210> SEQ ID NO 63
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 63
ggcuacaugc ugggaagugc caugagcagg cccaucauac auuuc                    45

<210> SEQ ID NO 64
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 64
ggaagugcca ugagcaggcc caucauacau uucggcagug acuau                    45

<210> SEQ ID NO 65
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 65
```
aggcccauca uacauuucgg cagugacuau gaggaccguu acuau    45

<210> SEQ ID NO 66
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 66
aucauacauu ucggcaguga cuaugaggac cguuacuauc gugaa    45

<210> SEQ ID NO 67
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 67
ugcauguacu uuauauuuuc uauauuugua acuuugcaug uucuu    45

<210> SEQ ID NO 68
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 68
uguacuuuau auuuucuaua uuuguaacuu ugcauguucu uguuu    45

<210> SEQ ID NO 69
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 69
ggcccaugga ugaguacagc aaccagaaca acuuugugca cgacu    45

<210> SEQ ID NO 70
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 70
acaaccacca aggggagaa cuucaccgag accgacguua agaug    45

<210> SEQ ID NO 71
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 71

```
uucaccgaga ccgacguuaa gaugauggag cgcgugguug agcag        45
```

<210> SEQ ID NO 72
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 72

```
uacaggccca uggaugagua cagcaaccag aacaacuuug ugcac        45
```

<210> SEQ ID NO 73
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 73

```
cacggucacc acaaccacca aggggagaa cuucaccgag accga         45
```

<210> SEQ ID NO 74
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 74

```
auguacuuua uauuuucuau auuuguaacu uugcauguuc uuguu        45
```

<210> SEQ ID NO 75
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 75

```
accgagaccg acguuaagau gauggagcgc gugguugagc agaug        45
```

<210> SEQ ID NO 76
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 76

```
gcaaccagaa caacuuugug cacgacugcg ucaauaucac aauca        45
```

<210> SEQ ID NO 77
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 77

```
accagaacaa cuuugugcac gacugcguca auaucacaau caagc        45
```

```
<210> SEQ ID NO 78
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 78
gcgucaauau caccaucaag cagcacacgg ucaccaccac cacca              45

<210> SEQ ID NO 79
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 79
uauuaccaga gaggaucgag caugguccuc uucuccucuc caccu              45

<210> SEQ ID NO 80
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 80
ucaucuuccu gauaguggga ugaggaaggu cuuccuguuu ucacc              45

<210> SEQ ID NO 81
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 81
ggcuacaugc ugggaagugc caugagcagg cccaucauac auuuc              45

<210> SEQ ID NO 82
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 82
ggaagugcca ugagcaggcc caucauacau uucggcagug acuau              45

<210> SEQ ID NO 83
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 83
gaaggucuuc cuguuucac caucuuucua aucuuuucc agcuu              45
```

```
<210> SEQ ID NO 84
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 84
ggcccaugga ugaguacagc aaccagaaca acuuugugca cgacu            45

<210> SEQ ID NO 85
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 85
gcaaccagaa caacuuugug cacgacugcg ucaauaucac aauca            45

<210> SEQ ID NO 86
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 86
accagaacaa cuuugugcac gacugcguca auaucacaau caagc            45

<210> SEQ ID NO 87
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 87
gcgucaauau cacaaucaag cagcacacgg ucaccacaac cacca            45

<210> SEQ ID NO 88
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 88
cacggucacc acaaccacca aggggagaa cuucaccgag accga             45

<210> SEQ ID NO 89
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 89
acaaccacca aggggagaa cuucaccgag accgacguua agaug             45
```

-continued

```
<210> SEQ ID NO 90
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 90
uucaccgaga ccgacguuaa gaugauggag cgcgugguug agcag          45

<210> SEQ ID NO 91
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 91
uaaugccagg ccaguaaaag uauaacagca aauaaccauu gguua          45

<210> SEQ ID NO 92
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 92
gccaguaaaa guauaacagc aaauaaccau ugguuaaucu ggacu          45

<210> SEQ ID NO 93
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 93
aacagcaaau aaccauuggu uaaucuggac uuauuuuugg acuua          45

<210> SEQ ID NO 94
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 94
cuuagugcaa cagguugagg cuaaaacaaa ucucagaaca gucug          45

<210> SEQ ID NO 95
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 95
gccagugcua acaccgggcc aauaagaaua uaacaccaaa uaacu          45

<210> SEQ ID NO 96
```

-continued

```
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 96
gcagcuagag cucaguauac uaaugcccua ucuuaguaga gauuu            45

<210> SEQ ID NO 97
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 97
uaaugcccua ucuuaguaga gauuucauag cuauuuagag auauu            45

<210> SEQ ID NO 98
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 98
augcccuauc uuaguagaga uuucauagcu auuuagagau auuuu            45

<210> SEQ ID NO 99
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 99
cuuaguagag auuucauagc uauuuagaga uauuuccau uuuaa             45

<210> SEQ ID NO 100
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 100
uaguagagau uucauagcua uuuagagaua uuuccauuu uaaga             45

<210> SEQ ID NO 101
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 101
auuucauagc uauuuagaga uauuuccau uuuaagaaaa cccga             45

<210> SEQ ID NO 102
<211> LENGTH: 45
```

```
<212> TYPE: RNA
<213> ORGANISM: Unknown
<220> FEATURE:
<223> OTHER INFORMATION: Description of Unknown:
      PRNP target sequence

<400> SEQUENCE: 102
gcuacacagc agcuguucaa caagaguaaa uauugucaca acacu              45

<210> SEQ ID NO 103
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 103
ucacaacacu gaaccucugg cuagaggaca uauucacagu gaaca              45

<210> SEQ ID NO 104
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 104
cacaacacug aaccucuggc uagaggacau auucacagug aacau              45

<210> SEQ ID NO 105
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 105
cuggcuagag gacauauuca cagugaacau aacuguaaca uauau              45

<210> SEQ ID NO 106
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 106
ggcuagagga cauauucaca gugaacauaa cuguaacaua auga              45

<210> SEQ ID NO 107
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 107
gugaacauaa cuguaacaua uaugaaaggc uucugggacu ugaaa              45

<210> SEQ ID NO 108
<211>

<213> ORGANISM: Unknown
<220> FEATURE:
<223> OTHER INFORMATION: Description of Unknown:
PRNP target sequence

<400> SEQUENCE: 108
auauaugaaa ggcuucuggg acuugaaauc aaauguuugg gaaug 45

<210> SEQ ID NO 109
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 109
gcagcuagag cucaguauac uaaugcccua ucuuaguaga gauuu 45

<210> SEQ ID NO 110
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 110
gggaauggug cccuuggagg caaccuccca uuuuagaugu uuaaa 45

<210> SEQ ID NO 111
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 111
ugcccuugga ggcaaccucc cauuuuagau guuuaaagga cccua 45

<210> SEQ ID NO 112
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 112
gcuagaaacu ugaguuucuu cauuucuguc ucacaauuau caaaa 45

<210> SEQ ID NO 113
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 113
uaaacuauag guaauuaagg cagcugaaaa guaaauugcc uucua 45

<210> SEQ ID NO 114
<211> LENGTH: 45
<212> TYPE: RNA
<213> ORGANISM: Unknown

```
<220> FEATURE:
<223> OTHER INFORMATION: Description of Unknown:
      PRNP target sequence

<400> SEQUENCE: 114 uuucu

```
<223> OTHER INFORMATION: Description of Unknown:
      PRNP target sequence

<400> SEQUENCE: 120
agcugcaguu gugaaagcac caucaucaua gaggaugaug uaauu              45

<210> SEQ ID NO 121
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 121
ugcaguugug aaagcaccau caucauagag gaugauguaa uuaaa              45

<210> SEQ ID NO 122
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 122
aguugugaaa gcaccaucau cauagaggau gauguaauua aaaaa              45

<210> SEQ ID NO 123
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 123
uugugaaagc accaucauca uagaggauga uguaauuaaa aaaug              45

<210> SEQ ID NO 124
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 124
aggcuccauu ccaaagiuggg aaagaaauuc ugcuagcauu guuua             45

<210> SEQ ID NO 125
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 125
aaaaaauggu cagugugcaa agaaaagaac ugcuugcauu ucuuu              45

<210> SEQ ID NO 126
<211> LENGTH: 45
<212> TYPE: RNA
<213> ORGANISM: Unknown
<220> FEATURE:
<223> OTHER INFORMATION: Description of Unknown:
```

PRNP target sequence

<400> SEQUENCE: 126
gcaaagaaaa gaacugcuug cauuucuuua uuucugcuc auaau          45

<210> SEQ ID NO 127
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 127
caaagaaaag aacugcuugc auuucuuuau ucugcucca uaauu          45

<210> SEQ ID NO 128
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 128
aagaacugcu ugcauuucuu uauuucuguc ucauaauugu caaaa          45

<210> SEQ ID NO 129
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 129
ccagcagaca uaaacugcga uagcuucagc uugcacugug gauuu          45

<210> SEQ ID NO 130
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 130
ucaaaaacca gaauugguc aaguucauag uuucuguaau uggcu          45

<210> SEQ ID NO 131
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 131
cagaauuagg ucaaguucau aguuucugua auuggcuuuu gaauc          45

<210> SEQ ID NO 132
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 132
ugcgauagcu ucagcuugca cuguggauuu ucuguauaga auaua            45

<210> SEQ ID NO 133
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 133
uuaggucaag uucauaguuu cuguaauugg cuuuugaauc aaaga            45

<210> SEQ ID NO 134
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 134
auauaaaaca uaacuucaag cuuaugucuu cuuuuaaaa caucu             45

<210> SEQ ID NO 135
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 135
gggaauggug cccuuggagg caaccuccca uuuuagaugu uuaaa            45

<210> SEQ ID NO 136
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 136
aaaaaauauc uuagguugga gaugacagaa auaugauuga uuuga            45

<210> SEQ ID NO 137
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 137
aguggaaaaa gaaauucugu uaauguuaau uaaaguaaaa uuauu            45

<210> SEQ ID NO 138
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 138
aauuaaagua aaauuauucc cugaauuguu ugauauuguc accua 45

<210> SEQ ID NO 139
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 139
uuauucccug aauuguuuga uauugucacc uagcagauau guauu 45

<210> SEQ ID NO 140
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 140
accuagcaga uauguauuac uuuucugcaa uguuauuauu ggcuu 45

<210> SEQ ID NO 141
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 141
gauauguauu acuuuucugc aauguuauua uuggcuugca cuuug 45

<210> SEQ ID NO 142
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 142
guauuacuuu ucugcaaugu uauuauuggc uugcacuuug ugagu 45

<210> SEQ ID NO 143
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 143
cuggucuuug aaucugcaug uacuucacgu uuucuauauu uguaa 45

<210> SEQ ID NO 144
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 144

```
auguuauuau uggcuugcac uuugugagua uucuauguaa aaaua            45

<210> SEQ ID NO 145
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 145
gcauguacuu cacguuuucu auauuuguaa cuuugcaugu auuuu            45

<210> SEQ ID NO 146
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 146
guacuucacg uuuucuauau uuguaacuuu gcauguauuu uguuu            45

<210> SEQ ID NO 147
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 147
acguuuucua uauuuguaac uuugcaugua uuuuguuuug ucaua            45

<210> SEQ ID NO 148
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 148
uuucuauauu uguaacuuug cauguauuuu guuuugucau auaaa            45

<210> SEQ ID NO 149
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 149
uucuauauuu guaacuuugc auguauuuug uuuugucaua uaaaa            45

<210> SEQ ID NO 150
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 150
```
guauauaaaa uauauauugc auaggacaga cuuaggaguu uuguu                    45

<210> SEQ ID NO 151
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 151
uauauaaaau auauauugca uaggacagac uuaggaguuu uguuu                    45

<210> SEQ ID NO 152
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 152
aaauauauau ugcauaggac agacuuagga guuuguuua gagca                     45

<210> SEQ ID NO 153
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 153
cuuaggaguu uuguuuagag caguuaacau cugaaguguc uaaug                    45

<210> SEQ ID NO 154
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 154
uuuguuuaga gcaguuaaca ucugaagugu cuaaugcauu aacuu                    45

<210> SEQ ID NO 155
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 155
gcaaagaaaa gaacugcuug cauuucuuua uuucugucuc auaau 45

<210> SEQ ID NO 156
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 156
acaucugaag ugucuaaugc auuaacuuuu guaagguacu gaaua 45

```
<210> SEQ ID NO 157
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 157
aagugucuaa ugcauuaacu uuuguaaggu acugaauacu uaaua              45

<210> SEQ ID NO 158
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 158
augcauuaac uuuguaagg uacugaauac uuaauaugug ggaaa              45

<210> SEQ ID NO 159
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 159
ucaaaaacca gaauuagguc aaguucauag uuucuguaau uggcu              45

<210> SEQ ID NO 160
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 160
uaagaaucca aguggacac cauuaacagg ucuuugaaau augca              45

<210> SEQ ID NO 161
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 161
aagaauccaa aguggacacc auuaacaggu cuuugaaaua ugcau              45

<210> SEQ ID NO 162
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 162
accauuaaca ggucuuugaa auaugcaugu acuuuauauu uucua              45
```

<210> SEQ ID NO 163
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 163
aggucuuuga aauaugcaug uacuuuauau uuucuauauu uguaa 45

<210> SEQ ID NO 164
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 164
ucuuugaaau augcauguac uuuauauuuu cuauauuugu aacuu 45

<210> SEQ ID NO 165
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 165
gaaauaugca uguacuuuau auuuucuaua uuuguaacuu ugcau 45

<210> SEQ ID NO 166
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 166
cuuuauauuu ucuauauuug uaacuuugca uguucuuguu uuguu 45

<210> SEQ ID NO 167
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 167
aguggaaaaa gaaauucugu uaauguuaau uaaaguaaaa uuauu 45

<210> SEQ ID NO 168
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 168
uauauuuucu auauuuguaa cuuugcaugu ucuuguuuug uuaua 45

```
<210> SEQ ID NO 169
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 169
auauuuucua uauuuguaac uuugcauguu cuuguuuugu auau              45

<210> SEQ ID NO 170
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 170
uucuauauuu guaacuuugc auguucuugu uuuguuauau aaaaa             45

<210> SEQ ID NO 171
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 171
ucuauauuug uaacuuugca uguucuuguu uuguuauaua aaaaa             45

<210> SEQ ID NO 172
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 172
uuguuauaua aaaaauugu aaauguuuaa uaucugacug aaauu              45

<210> SEQ ID NO 173
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 173
uguuauauaa aaaauugua aauguuuaau aucgacuga aauua               45

<210> SEQ ID NO 174
<211> LENGTH: 45
<212> TYPE: RNA
<213> ORGANISM: Unknown
<220> FEATURE:
<223> OTHER INFORMATION: Description of Unknown:
      PRNP target sequence

<400> SEQUENCE: 174
guuauauaaa aaaauguaa auguuuaaua ucgacugaa auuaa                45

<210> SEQ ID NO 175
```

<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 175
uuauauaaaa aaauuguaaa uguuuaauau cugacugaaa uuaaa 45

<210> SEQ ID NO 176
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 176
auguuauuau uggcuugcac uuugugagua uucuauguaa aaaua 45

<210> SEQ ID NO 177
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 177
guauauaaaa uauauauugc auaggacaga cuuaggaguu uuguu 45

<210> SEQ ID NO 178
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 178
accauuaaca ggucuuugaa auaugcaugu acuuuauauu uucua 45

<210> SEQ ID NO 179
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 179
aggucuuuga aauaugcaug uacuuuauau uuucuauauu uguaa 45

<210> SEQ ID NO 180
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 180
gcauguacuu uauauuuucu auauuuguaa cuuugcaugu ucuug 45

<210> SEQ ID NO 181
<211> LENGTH: 45

-continued

<212> TYPE: RNA
<213> ORGANISM: Unknown
<220> FEATURE:
<223> OTHER INFORMATION: Description of Unknown:
PRNP target sequence

<400> SEQUENCE: 181
uguacuuuau auuuucuaua uuuguaacuu ugcauguucu uguuu 45

<210> SEQ ID NO 182
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 182
guacuuuaua uuuucuauau uuguaacuuu gcauguucuu guuuu 45

<210> SEQ ID NO 183
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 183
cuuuauauuu ucuauauuug uaacuuugca uguucuuguu uuguu 45

<210> SEQ ID NO 184
<211> LENGTH: 45
<212> TYPE: RNA
<213> ORGANISM: Unknown
<220> FEATURE:
<223> OTHER INFORMATION: Description of Unknown:
PRNP target sequence

<400> SEQUENCE: 184
uauauuuucu auauuuguaa cuuugcaugu ucuuguuuug uuaua 45

<210> SEQ ID NO 185
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 185
agugccauga gcaggcccau 20

<210> SEQ ID NO 186
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 186
aggcccauca uacauuucgg 20

<210> SEQ ID NO 187
<211> LENGTH: 20
<212> TYPE: RNA

```
<213> ORGANISM: Unknown
<220> FEATURE:
<223> OTHER INFORMATION: Description of Unknown:
      PRNP target sequence

<400> SEQUENCE: 187
uucggcagug acuaugagga                                              20

<210> SEQ ID NO 188
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 188
agugacuaug aggaccguua                                              20

<210> SEQ ID NO 189
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 189
uuuucuauau uuguaacuuu                                              20

<210> SEQ ID NO 190
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 190
cuauauuugu aacuuugcau                                              20

<210> SEQ ID NO 191
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 191
acagcaacca gaacaacuuu                                              20

<210> SEQ ID NO 192
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 192
gagaacuuca ccgagaccga                                              20

<210> SEQ ID NO 193
<211> LENGTH: 20
<212> TYPE: RNA
<213> ORGANISM: Unknown
```

```
<220> FEATURE:
<223> OTHER INFORMATION: Description of Unknown:
      PRNP target sequence

<400> SEQUENCE: 193
guuaagauga uggagcgcgu                                           20

<210> SEQ ID NO 194
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 194
gaguacagca accagaacaa                                           20

<210> SEQ ID NO 195
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 195
caccaagggg gagaacuuca                                           20

<210> SEQ ID NO 196
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 196
ucuauauuug uaacuuugca                                           20

<210> SEQ ID NO 197
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 197
aagaugaugg agcgcguggu                                           20

<210> SEQ ID NO 198
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 198
uugugcacga cugcgucaau                                           20

<210> SEQ ID NO 199
<211> LENGTH: 20
<212> TYPE: RNA
<213> ORGANISM: Unknown
<220> FEATURE:
```

<223> OTHER INFORMATION: Description of Unknown:
      PRNP target sequence

<400> SEQUENCE: 199
ugcacgacug cgucaauauc                                               20

<210> SEQ ID NO 200
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 200
ucaagcagca cacggucacc                                               20

<210> SEQ ID NO 201
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 201
ucgagcaugg uccucuucuc                                               20

<210> SEQ ID NO 202
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 202
ugggaugagg aaggucuucc                                               20

<210> SEQ ID NO 203
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 203
agugccauga gcaggcccau                                               20

<210> SEQ ID NO 204
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 204
aggcccauca uacauuucgg                                               20

<210> SEQ ID NO 205
<211> LENGTH: 20
<212> TYPE: RNA
<213> ORGANISM: Unknown
<220> FEATURE:
<223> OTHER INFORMATION: Description of Unknown:

PRNP target sequence

<400> SEQUENCE: 205
uucaccaucu uucuaaucuu                                                    20

<210> SEQ ID NO 206
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 206
acagcaacca gaacaacuuu                                                    20

<210> SEQ ID NO 207
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 207
uugugcacga cugcgucaau                                                    20

<210> SEQ ID NO 208
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 208
ugcacgacug cgucaauauc                                                    20

<210> SEQ ID NO 209
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 209
ucaagcagca cacggucacc                                                    20

<210> SEQ ID NO 210
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 210
caccaagggg gagaacuuca                                                    20

<210> SEQ ID NO 211
<211> LENGTH: 20
<212> TYPE: RNA
<213> ORGANISM: Unknown
<220> FEATURE:
<223> OTHER INFORMATION: Description of Unknown:
      PRNP target sequence

```
<400> SEQUENCE: 211
gagaacuuca ccgagaccga                                               20

<210> SEQ ID NO 212
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 212
guuaagauga uggagcgcgu                                               20

<210> SEQ ID NO 213
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 213
aaaaguauaa cagcaaauaa                                               20

<210> SEQ ID NO 214
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 214
acagcaaaua accauugguu                                               20

<210> SEQ ID NO 215
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 215
uugguuaauc uggacuuauu                                               20

<210> SEQ ID NO 216
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 216
ugaggcuaaa acaaaucuca                                               20

<210> SEQ ID NO 217
<211> LENGTH: 20
<212> TYPE: RNA
<213> ORGANISM: Unknown
<220> FEATURE:
<223> OTHER INFORMATION: Description of Unknown:
      PRNP target sequence
```

```
<400> SEQUENCE: 217
gggccaauaa gaauauaaca                                               20

<210> SEQ ID NO 218
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 218
uauacuaaug cccuaucuua                                               20

<210> SEQ ID NO 219
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 219
guagagauuu cauagcuauu                                               20

<210> SEQ ID NO 220
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 220
agagauuuca uagcuauuua                                               20

<210> SEQ ID NO 221
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 221
auagcuauuu agagauauuu                                               20

<210> SEQ ID NO 222
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 222
agcuauuuag agauauuuuc                                               20

<210> SEQ ID NO 223
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 223
```
agagauauuu uccauuuuaa                                              20

<210> SEQ ID NO 224
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 224
uucaacaaga guaaauauug                                              20

<210> SEQ ID NO 225
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 225
ucuggcuaga ggacauauuc                                              20

<210> SEQ ID NO 226
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 226
cuggcuagag gacauauuca                                              20

<210> SEQ ID NO 227
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 227
auucacagug aacauaacug                                              20

<210> SEQ ID NO 228
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 228
ucacagugaa cauaacugua                                              20

<210> SEQ ID NO 229
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 229
acauauauga aaggcuucug                                              20

<210> SEQ ID NO 230
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 230
cugggacuug aaaucaaaug                                              20

<210> SEQ ID NO 231
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 231
uauacuaaug cccuaucuua                                              20

<210> SEQ ID NO 232
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 232
ggaggcaacc ucccauuuua                                              20

<210> SEQ ID NO 233
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 233
ccucccauuu uagauguuua                                              20

<210> SEQ ID NO 234
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 234
uucuucauuu cugucucaca                                              20

<210> SEQ ID NO 235
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 235
uaaggcagcu gaaaaguaaa                                              20

```
<210> SEQ ID NO 236
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 236
cucacaauua ucaaaagcua                                        20

<210> SEQ ID NO 237
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 237
agcugaaaag uaaauugccu                                        20

<210> SEQ ID NO 238
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 238
ugcccuaugu uucuguacuu                                        20

<210> SEQ ID NO 239
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 239
gaaggcaaau cuccuuuguc                                        20

<210> SEQ ID NO 240
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 240
uuguccauuu accuggaaac                                        20

<210> SEQ ID NO 241
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 241
uuugacauac aggagagcug                                        20
```

```
<210> SEQ ID NO 242
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 242
agcaccauca ucauagagga                                              20

<210> SEQ ID NO 243
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 243
accaucauca uagaggauga                                              20

<210> SEQ ID NO 244
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 244
aucaucauag aggaugaugu                                              20

<210> SEQ ID NO 245
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 245
caucauagag gaugauguaa                                              20

<210> SEQ ID NO 246
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 246
gugggaaaga aauucugcua                                              20

<210> SEQ ID NO 247
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 247
ugcaaagaaa agaacugcuu                                              20
```

```
<210> SEQ ID NO 248
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 248
gcuugcauuu cuuuauuucu                                              20

<210> SEQ ID NO 249
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 249
cuugcauuuc uuuauuucug                                              20

<210> SEQ ID NO 250
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 250
uucuuuauuu cugucucaua                                              20

<210> SEQ ID NO 251
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 251
ugcgauagcu ucagcuugca                                              20

<210> SEQ ID NO 252
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 252
aggucaaguu cauaguuucu                                              20

<210> SEQ ID NO 253
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 253
uucauaguuu cuguaauugg                                              20

<210> SEQ ID NO 254
```

```
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 254
uugcacugug gauuuucugu                                               20

<210> SEQ ID NO 255
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 255
aguuucugua auuggcuuuu                                               20

<210> SEQ ID NO 256
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 256
ucaagcuuau gucuucuuuu                                               20

<210> SEQ ID NO 257
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 257
ggaggcaacc ucccauuuua                                               20

<210> SEQ ID NO 258
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 258
uuggagauga cagaaauaug                                               20

<210> SEQ ID NO 259
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 259
ucuguuaaug uuaauuaaag                                               20

<210> SEQ ID NO 260
<211> LENGTH: 20
```

<212> TYPE: RNA
<213> ORGANISM: Unknown
<220> FEATURE:
<223> OTHER INFORMATION: Description of Unknown:
PRNP target sequence

<400> SEQUENCE: 260
auucccugaa uuguuugaua 20

<210> SEQ ID NO 261
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 261
uuugauauug ucaccuagca 20

<210> SEQ ID NO 262
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 262
auuacuuuuc ugcaauguua 20

<210> SEQ ID NO 263
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 263
ucugcaaugu uauuauuggc 20

<210> SEQ ID NO 264
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 264
aauguuauua uuggcuugca 20

<210> SEQ ID NO 265
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 265
gcauguacuu cacguuuucu 20

<210> SEQ ID NO 266
<211> LENGTH: 20
<212> TYPE: RNA

<213> ORGANISM: Unknown
<220> FEATURE:
<223> OTHER INFORMATION: Description of Unknown:
PRNP target sequence

<400> SEQUENCE: 266
ugcacuuugu gaguauucua 20

<210> SEQ ID NO 267
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 267
uuucuauauu uguaacuuug 20

<210> SEQ ID NO 268
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 268
uauauuugua acuuugcaug 20

<210> SEQ ID NO 269
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 269
guaacuuugc auguauuuug 20

<210> SEQ ID NO 270
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 270
cuuugcaugu auuuuguuuu 20

<210> SEQ ID NO 271
<211> LENGTH: 20
<212> TYPE: RNA
<213> ORGANISM: Unknown
<220> FEATURE:
<223> OTHER INFORMATION: Description of Unknown:
PRNP target sequence

<400> SEQUENCE: 271
uuugcaugua uuuuguuuug 20

<210> SEQ ID NO 272
<211> LENGTH: 20
<212> TYPE: RNA
<213> ORGANISM: Unknown

```
<220> FEATURE:
<223> OTHER INFORMATION: Description of Unknown:
      PRNP target sequence

<400> SEQUENCE: 272
auugcauagg acagacuuag                                               20

<210> SEQ ID NO 273
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 273
uugcauagga cagacuuagg                                               20

<210> SEQ ID NO 274
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 274
aggacagacu uaggaguuuu                                               20

<210> SEQ ID NO 275
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 275
uagagcaguu aacaucugaa                                               20

<210> SEQ ID NO 276
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 276
uaacaucuga agugucuaau                                               20

<210> SEQ ID NO 277
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 277
gcuugcauuu cuuuauuucu                                               20

<210> SEQ ID NO 278
<211> LENGTH: 20
<212> TYPE: RNA
<213> ORGANISM: Unknown
<220> FEATURE:
```

```
<223> OTHER INFORMATION: Description of Unknown:
      PRNP target sequence

<400> SEQUENCE: 278
aaugcauuaa cuuuuguaag                                          20

<210> SEQ ID NO 279
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 279
uaacuuuugu aagguacuga                                          20

<210> SEQ ID NO 280
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 280
uaagguacug aauacuuaau                                          20

<210> SEQ ID NO 281
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 281
aggucaaguu cauaguuucu                                          20

<210> SEQ ID NO 282
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 282
gacaccauua acaggucuuu                                          20

<210> SEQ ID NO 283
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 283
acaccauuaa caggucuuug                                          20

<210> SEQ ID NO 284
<211> LENGTH: 20
<212> TYPE: RNA
<213> ORGANISM: Unknown
<220> FEATURE:
<223> OTHER INFORMATION: Description of Unknown:
```

```
                    PRNP target sequence

<400> SEQUENCE: 284
uugaaauaug cauguacuuu                                                   20

<210> SEQ ID NO 285
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 285
gcauguacuu uauauuuucu                                                   20

<210> SEQ ID NO 286
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 286
uguacuuuau auuuucuaua                                                   20

<210> SEQ ID NO 287
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 287
uuuauauuuu cuauauuugu                                                   20

<210> SEQ ID NO 288
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 288
auuuguaacu uugcauguuc                                                   20

<210> SEQ ID NO 289
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 289
ucuguuaaug uuaauuaaag                                                   20

<210> SEQ ID NO 290
<211> LENGTH: 20
<212> TYPE: RNA
<213> ORGANISM: Unknown
<220> FEATURE:
<223> OTHER INFORMATION: Description of Unknown:
      PRNP target sequence
```

-continued

```
<400> SEQUENCE: 290
uguaacuuug cauguucuug                                             20

<210> SEQ ID NO 291
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 291
guaacuuugc auguucuugu                                             20

<210> SEQ ID NO 292
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 292
uuugcauguu cuuguuuugu                                             20

<210> SEQ ID NO 293
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 293
uugcauguuc uuguuuuguu                                             20

<210> SEQ ID NO 294
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 294
auuguaaaug uuuaauaucu                                             20

<210> SEQ ID NO 295
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 295
uuguaaaugu uuaauaucug                                             20

<210> SEQ ID NO 296
<211> LENGTH: 20
<212> TYPE: RNA
<213> ORGANISM: Unknown
<220> FEATURE:
<223> OTHER INFORMATION: Description of Unknown:
      PRNP target sequence
```

```
<400> SEQUENCE: 296
uguaaauguu uaauaucuga                                               20

<210> SEQ ID NO 297
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 297
guaaauguuu aauaucugac                                               20

<210> SEQ ID NO 298
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 298
ugcacuuugu gaguauucua                                               20

<210> SEQ ID NO 299
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 299
auugcauagg acagacuuag                                               20

<210> SEQ ID NO 300
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 300
uugaaauaug cauguacuuu                                               20

<210> SEQ ID NO 301
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 301
gcauguacuu uauauuuucu                                               20

<210> SEQ ID NO 302
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 302
```

-continued

```
uuucuauauu uguaacuuug                                                20

<210> SEQ ID NO 303
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 303
cuauauuugu aacuuugcau                                                20

<210> SEQ ID NO 304
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 304
uauauuugua acuuugcaug                                                20

<210> SEQ ID NO 305
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 305
auuuguaacu uugcauguuc                                                20

<210> SEQ ID NO 306
<211> LENGTH: 20
<212> TYPE: RNA
<213> ORGANISM: Unknown
<220> FEATURE:
<223> OTHER INFORMATION: Description of Unknown:
      PRNP target sequence

<400> SEQUENCE: 306
uguaacuuug cauguucuug                                                20
```